(12) United States Patent
Liu et al.

(10) Patent No.: US 10,973,915 B2
(45) Date of Patent: Apr. 13, 2021

(54) ANTI-PD-1 ANTIBODIES AND USES THEREOF

(71) Applicant: PharmaExplorer Limited, Tortola (GB)

(72) Inventors: Lile Liu, Shanghai (CN); Xinxiu Yang, Shanghai (CN); Haishan Luo, Shanghai (CN); Hu Liu, Shanghai (CN); Zhengrong Shuai, Shanghai (CN); Jian Wang, Shanghai (CN); Qin Zhong, Shanghai (CN); Qing Duan, Shanghai (CN); Hongzhuan Gu, Shanghai (CN); Tatchi Teddy Yang, Shanghai (CN)

(73) Assignee: SHANGHAI YUNYI HEALTHCARE AND TECHNOLOGY CO., LTD., Shanghai (CN)

( * ) Notice: Subject to any disclaimer, the term of this patent is extended or adjusted under 35 U.S.C. 154(b) by 328 days.

(21) Appl. No.: 15/747,504

(22) PCT Filed: Jul. 27, 2016

(86) PCT No.: PCT/CN2016/091962
§ 371 (c)(1),
(2) Date: Jan. 25, 2018

(87) PCT Pub. No.: WO2017/016497
PCT Pub. Date: Feb. 2, 2017

(65) Prior Publication Data
US 2018/0214548 A1    Aug. 2, 2018

(30) Foreign Application Priority Data

Jul. 28, 2015    (CN) .......................... 201510451773.6

(51) Int. Cl.
*A61K 39/395*    (2006.01)
*C07K 16/28*    (2006.01)
*A61P 35/00*    (2006.01)

(52) U.S. Cl.
CPC .. *A61K 39/39558* (2013.01); *A61K 39/39591* (2013.01); *A61P 35/00* (2018.01); *C07K 16/2803* (2013.01); *C07K 16/2818* (2013.01); *C07K 2317/21* (2013.01); *C07K 2317/24* (2013.01); *C07K 2317/33* (2013.01); *C07K 2317/732* (2013.01); *C07K 2317/734* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

2012/0282263 A1    11/2012    Dudler et al.

FOREIGN PATENT DOCUMENTS

| JP | 2006521783 A | 9/2006 |
|---|---|---|
| JP | 2006340714 A | 12/2006 |
| JP | 2013521769 A | 6/2013 |
| JP | 2014012003 A | 1/2014 |
| JP | 2014515017 A | 6/2014 |
| JP | 2014515922 A | 7/2014 |
| WO | 2004056875 A1 | 7/2004 |
| WO | 2006121168 A1 | 11/2006 |
| WO | 2010070263 A1 | 6/2010 |
| WO | 2011110621 A1 | 9/2011 |
| WO | 2012135408 A1 | 10/2012 |

OTHER PUBLICATIONS

Santini et al, Cancer J. 24(1):15-19, 2018.*
Kussie et al (Journal of Immunology, 152:146-152, 1994.*
Chen et al, (The EMBO Journal, 14(12):2784-2794, 1995).*
Bendig (Methods: A Companion to Methods in Enzymology 1995; 8:83-93).*
Wakabayashi et al., "Development and clinical applications of cancer immunotherapy against PD-1 signaling pathway," Journal of Biomedical Science, vol. 26, No. 96, pp. 1-13 (2019).
Chamoto et al., "Current issues and perspectives in PD-1 blockade cancer immunotherapy," International Journal of Clinical Oncology, 11 pages, 2020.
Blank et al., "Interaction of PD-L1 on tumor cells with PD-1 on tumor-specific T cells as a mechanism of immune evasion: implications for tumor immunotherapy," Cancer Immunol Immunother, vol. 54, pp. 307-314 (2005).
Brahmer et al., "Phase 1 Study of Single-Agent Anti-Programmed Death-1 (MDX-1106) in Refractory solid Tumors: Safety, Clinical Activity, Pharmacodynamics, and Immuniologic Correlates," Journal of Clinical Oncology, vol. 28, No. 19 (Jul. 1, 2010).
Freeman et al., "Engagement of the PD-1 Immunoinhibitory Receptor by a Novel B7 Family Member Leads to Negative Regulation of Lymphocyte Activation," J. Exp. Med., vol. 192, No. 7, pp. 1027-1034 (Oct. 2, 2000).
Greenwald et al., "The B7 Family Revisited," Annu. Rev. Immunol., vol. 23, pp. 515-548, (2005).
Harding et al., "Class Switching in Human Immunoglobulin Transgenic Mice," Annals New York Academy of Sciences, vol. 764, pp. 536-546 (1995).
Hirano et al., "Blockade of B7-H1 and PD-1 by Monoclonal Antibodies Potentiates Cancer Therapeutic Immunity," vol. 65, Cancer Research, pp. 1089-1096 (Feb. 1, 2005).

(Continued)

*Primary Examiner* — Patricia Duffy
(74) *Attorney, Agent, or Firm* — Panitch Schwarze Belisario & Nadel LLP; Stephany G. Small; Lars H. Genieser

(57) ABSTRACT

Anti-PD-1 antibodies and antigen-binding fragments thereof are described. Also described are nucleic acids encoding the antibodies, compositions comprising the antibodies, and methods of producing the antibodies and using the antibodies for treating or preventing diseases such as cancers and autoimmune diseases.

15 Claims, 33 Drawing Sheets

Specification includes a Sequence Listing.

(56) References Cited

OTHER PUBLICATIONS

Int'l Preliminary Report on Patentability dated Jan. 30, 2018 in Int'l Application No. PCT/CN2016/091962.
Int'l Search Report dated Nov. 2, 2016 in Int'l Application No. PCT/CN2016/091962.
Kipriyanov et al., "Two amino acid mutations in an anti-human CD3 single chain Fv antibody fragment that affect the yield on bacterial secretion but not the affinity," Protein Engineering, vol. 10, No. 4, pp. 445-453 (1997).
Lonberg et al., "Antigen-specific human antibodies from mice comprising four distinct genetic modifications," Nature, vol. 368, pp. 856-859 (1994).
Lonberg et al., "Human Antibodies from Transgenic Mice," Intern. Rev. Immunol., vol. 13, pp. 65-93 (1995).
Sharpe et al., "The function of programmed cell death 1 and its ligands in regulating autoimmunity and infection," Nature Immunology, vol. 8, No. 3, pp. 239-245 (2007).
Topalian et al., "Survival, durable Tumor Remission, and Lont-Term Safety in Patients with Advanced Melanoma Receiving Nivolumab," Journal of Clinical Oncology, vol. 32, No. 10, pp. 1020-1031 (Apr. 1, 2014).
Weinstock et al., "Targeting PD-1/PD-L1 in the treatment of metastatic renal cell carcinoma," Therapeutic Advances in Urology, vol. 7, No. 6, pp. 365-377 (2015).
Wherry, E. John, "T cell exhaustion," Nature Immunology, vol. 12, No. 6, pp. 492-499 (2011).
Zippelius et al., "Induced PD-L1 Expression Mediates Acquired Resistance to Agonistic Anti-CD40 Treatment," Cancer Immunology Research, vol. 3, No. 3, pp. 236-244 (2015).
Zou et al., "Inhibitory B7-family molecules in the tumour microenvironment," Nature Reviews Immunology, vol. 8, pp. 167-477 (Jun. 2008).
Office Action dated Feb. 5, 2019 in JP Application No. 2018524522.
Ohaegbulam et al., "Human cancer immunotherapy with antibodies to the PD-1 and PD-L1 pathway," Trends in Molecular Medicine, vol. 21, No. 1, pp. 24-33 (Jan. 1, 2015).
Partial Supplementary European Search Report dated Mar. 13, 2019 in EP Application No. 16829862.8.
Silva et al., "The S228P Mutation Prevents in Vivo and in Vitro IgG4 Fab-arm Exchange as Demonstrated using a Combination of Novel Quantitative Immunoassays and Physiological Matrix Preparation," The Journal of Biological Chemistry, vol. 290, No. 9, pp. 5462-5469 (Feb. 27, 2015).
Wang et al., "In Vitro Characterization of the Anti-PD-1 Antibody Nivolumab, BMS-936558, and In Vivo Toxicology in Non-Human Primates," Cancer Immunology Research, vol. 2, No. pp. 846-856 (May 28, 2014).

* cited by examiner

Before concentration

9B2C6C9, 6.55 mg/ml

76G5B3, 2.7 mg/ml

223G6B5, 11.9 mg/ml

After concentration

9B2C6C9, 171 mg/ml

76G5B3, 114 mg/ml

223G6B5, 100.1 mg/ml

SEQUENCE LISTING

```
<160> NUMBER OF SEQ ID NOS: 77

<210> SEQ ID NO 1
<211> LENGTH: 123
<212> TYPE: PRT
<213> ORGANISM: Homo sapiens

<400> SEQUENCE: 1

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Thr Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Ile Asn Tyr Asn Pro Ser Leu
    50                  55                  60

Lys Ser Arg Val Thr Ile Ser Val Asp Arg Ser Lys Asn Gln Phe Ser
65                  70                  75                  80
```

```
Leu Lys Leu Ser Ser Val Thr Ala Ala Asp Thr Ala Val Tyr Tyr Cys
                85                  90                  95

Ala Arg Asp His Tyr Gly Ser Gly Ser Tyr Tyr Asn Gly Met Asp Val
            100                 105                 110

Trp Gly Gln Gly Thr Thr Val Thr Val Ser Ser
        115                 120

<210> SEQ ID NO 2
<211> LENGTH: 11
<212> TYPE: PRT
<213> ORGANISM: Homo sapiens

<400> SEQUENCE: 2

Gly Gly Ser Ile Ser Thr Ser Asn Trp Trp Ser
1               5                   10

<210> SEQ ID NO 3
<211> LENGTH: 16
<212> TYPE: PRT
<213> ORGANISM: Homo sapiens

<400> SEQUENCE: 3

Glu Ile Tyr His Ser Gly Ser Ile Asn Tyr Asn Pro Ser Leu Lys Ser
1               5                   10                  15

<210> SEQ ID NO 4
<211> LENGTH: 14
<212> TYPE: PRT
<213> ORGANISM: Homo sapiens

<400> SEQUENCE: 4

Asp His Tyr Gly Ser Gly Ser Tyr Tyr Asn Gly Met Asp Val
1               5                   10

<210> SEQ ID NO 5
<211> LENGTH: 112
<212> TYPE: PRT
<213> ORGANISM: Homo sapiens

<400> SEQUENCE: 5

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Arg His Ser Pro Trp Thr Phe Gly Gln Gly Thr Lys Val Glu Ile Lys
            100                 105                 110

<210> SEQ ID NO 6
<211> LENGTH: 16
<212> TYPE: PRT
<213> ORGANISM: Homo sapiens

<400> SEQUENCE: 6
```

```
Arg Ser Ser Gln Ser Leu Leu Tyr Ser Asp Gly Tyr Asn Tyr Leu Asp
1               5                   10                  15

<210> SEQ ID NO 7
<211> LENGTH: 7
<212> TYPE: PRT
<213> ORGANISM: Homo sapiens

<400> SEQUENCE: 7

Leu Gly Ser Asn Arg Ala Ser
1               5

<210> SEQ ID NO 8
<211> LENGTH: 9
<212> TYPE: PRT
<213> ORGANISM: Homo sapiens

<400> SEQUENCE: 8

Met Gln Ala Arg Gln Thr Pro Trp Thr
1               5

<210> SEQ ID NO 9
<211> LENGTH: 114
<212> TYPE: PRT
<213> ORGANISM: Homo sapiens

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Gly Phe His Trp Val Arg Gln Ala Pro Gly Lys Gly Leu Glu Trp Val
        35                  40                  45

Ala Val Ile Trp Tyr Asp Gly Ser Asn Glu Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Phe Cys
                85                  90                  95

Val Val Asn Pro Phe Asp Tyr Trp Gly Gln Gly Thr Leu Val Thr Val
            100                 105                 110

Ser Ser

<210> SEQ ID NO 10
<211> LENGTH: 10
<212> TYPE: PRT
<213> ORGANISM: Homo sapiens

<400> SEQUENCE: 10

Gly Phe Thr Phe Ser Asp Tyr Gly Phe His
1               5                   10

<210> SEQ ID NO 11
<211> LENGTH: 17
<212> TYPE: PRT
<213> ORGANISM: Homo sapiens

<400> SEQUENCE: 11

Val Ile Trp Tyr Asp Gly Ser Asn Glu Tyr Tyr Thr Asp Ser Val Lys
1               5                   10                  15
```

Gly

<210> SEQ ID NO 12
<211> LENGTH: 5
<212> TYPE: PRT
<213> ORGANISM: Homo sapiens

<400> SEQUENCE: 12

Asn Pro Phe Asp Tyr
1               5

<210> SEQ ID NO 13
<211> LENGTH: 107
<212> TYPE: PRT
<213> ORGANISM: Homo sapiens

<400> SEQUENCE: 13

Asp Ile Gln Met Thr Gln Ser Pro Ser Ser Leu Ser Ala Phe Val Gly
1               5                   10                  15

Asp Arg Val Thr Ile Thr Cys Arg Ala Ser Gln Gly Ile Asn His Tyr
            20                  25                  30

Leu Ala Trp Tyr Gln Gln Lys Pro Gly Lys Ala Pro Asn Leu Leu Ile
        35                  40                  45

Leu Ala Ala Ser Thr Leu Leu Ser Gly Val Pro Ser Arg Phe Gly Gly
    50                  55                  60

Arg Gly Ser Gly Thr Asp Phe Thr Leu Ile Ile Ser Ser Leu Gln Pro
65                  70                  75                  80

Glu Asp Val Ala Thr Tyr Tyr Cys Gln Lys Tyr Asp Ser Ala Pro Tyr
                85                  90                  95

Thr Phe Gly Gln Gly Thr Lys Leu Glu Ile Lys
            100                 105

<210> SEQ ID NO 14
<211> LENGTH: 11
<212> TYPE: PRT
<213> ORGANISM: Homo sapiens

<400> SEQUENCE: 14

Arg Ala Ser Gln Gly Ile Asn His Tyr Leu Ala
1               5                   10

<210> SEQ ID NO 15
<211> LENGTH: 7
<212> TYPE: PRT
<213> ORGANISM: Homo sapiens

<400> SEQUENCE: 15

Ala Ala Ser Thr Leu Leu Ser
1               5

<210> SEQ ID NO 16
<211> LENGTH: 9
<212> TYPE: PRT
<213> ORGANISM: Homo sapiens

<400> SEQUENCE: 16

Gln Lys Tyr Asp Ser Ala Pro Tyr Thr
1               5

<210> SEQ ID NO 17
<211> LENGTH: 115
<212> TYPE: PRT

-continued

<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Leu Thr Gly Asp Pro Asp Tyr Trp Gly Gln Gly Thr Leu Val Thr
            100                 105                 110

Val Ser Ser
        115

<210> SEQ ID NO 18
<211> LENGTH: 10
<212> TYPE: PRT
<213> ORGANISM: Homo sapiens

<400> SEQUENCE: 18

Gly Phe Thr Phe Ser Ser Tyr Ala Met Ser
1               5                   10

<210> SEQ ID NO 19
<211> LENGTH: 17
<212> TYPE: PRT
<213> ORGANISM: Homo sapiens

<400> SEQUENCE: 19

Thr Ile Ser Gly Ser Gly Gly Thr Thr Tyr Tyr Ala Asp Ser Val Lys
1               5                   10                  15

Gly

<210> SEQ ID NO 20
<211> LENGTH: 6
<212> TYPE: PRT
<213> ORGANISM: Homo sapiens

<400> SEQUENCE: 20

Thr Gly Asp Pro Asp Tyr
1               5

<210> SEQ ID NO 21
<211> LENGTH: 107
<212> TYPE: PRT
<213> ORGANISM: Homo sapiens

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

```
Tyr Asp Ala Ser Lys Arg Ala Thr Gly Ile Pro Ala Arg Phe Ser Gly
            50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Asn Asn Trp Pro Leu
                 85                  90                  95
Thr Phe Gly Gly Gly Thr Lys Val Glu Ile Lys
             100                 105
```

<210> SEQ ID NO 22
<211> LENGTH: 11
<212> TYPE: PRT
<213> ORGANISM: Homo sapiens

<400> SEQUENCE: 22

```
Arg Ala Ser Gln Ser Val Ser Ser Tyr Leu Ala
 1               5                   10
```

<210> SEQ ID NO 23
<211> LENGTH: 7
<212> TYPE: PRT
<213> ORGANISM: Homo sapiens

<400> SEQUENCE: 23

```
Asp Ala Ser Lys Arg Ala Thr
 1               5
```

<210> SEQ ID NO 24
<211> LENGTH: 9
<212> TYPE: PRT
<213> ORGANISM: Homo sapiens

<400> SEQUENCE: 24

```
Gln Gln Arg Asn Asn Trp Pro Leu Thr
 1               5
```

<210> SEQ ID NO 25
<211> LENGTH: 119
<212> TYPE: PRT
<213> ORGANISM: Homo sapiens

<400> SEQUENCE: 25

```
Gln Val Gln Leu Gln Glu Ser Gly Pro Gly Leu Val Lys Pro Ser Glu
 1               5                   10                  15
Thr Leu Ser Leu Thr Cys Ala Val Ser Gly His Ser Ile Arg Gly Ser
                 20                  25                  30
Tyr Phe Trp Gly Trp Ile Arg Gln Pro Pro Gly Arg Gly Leu Glu Trp
             35                  40                  45
Ile Gly Ser Ile Tyr His Ser Gly Ser Thr Tyr Thr Asn Pro Ser Leu
         50                  55                  60
Lys Ser Arg Ala Thr Ile Ser Val Asp Thr Ser Lys Asn Gln Phe Ser
 65                  70                  75                  80
Leu Lys Leu Asn Ser Val Thr Ala Ala Asp Thr Ala Val Tyr Tyr Cys
                 85                  90                  95
Ala Arg Asp Leu Asp Ile Ala Thr Thr Arg Asp Tyr Trp Gly Gln Gly
                100                 105                 110
Thr Leu Val Thr Val Ser Ser
            115
```

```
<210> SEQ ID NO 26
<211> LENGTH: 6
<212> TYPE: PRT
<213> ORGANISM: Homo sapiens

<400> SEQUENCE: 26

Gly Ser Tyr Phe Trp Gly
1               5

<210> SEQ ID NO 27
<211> LENGTH: 16
<212> TYPE: PRT
<213> ORGANISM: Homo sapiens

<400> SEQUENCE: 27

Ser Ile Tyr His Ser Gly Ser Thr Tyr Thr Asn Pro Ser Leu Lys Ser
1               5                   10                  15

<210> SEQ ID NO 28
<211> LENGTH: 10
<212> TYPE: PRT
<213> ORGANISM: Homo sapiens

<400> SEQUENCE: 28

Asp Leu Asp Ile Ala Thr Thr Arg Asp Tyr
1               5                   10

<210> SEQ ID NO 29
<211> LENGTH: 110
<212> TYPE: PRT
<213> ORGANISM: Homo sapiens

<400> SEQUENCE: 29

Asp Ile Gln Leu Thr Gln Ser Pro Ser Phe Leu Ser Ala Ser Val Gly
1               5                   10                  15

Asp Arg Val Thr Ile Ile Cys Arg Ala Ser Gln Gly Ile Asn Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asp Ser Tyr Pro Arg
                85                  90                  95

Thr Phe Gly Gln Gly Thr Lys Val Glu Ile Lys Arg Thr Val
            100                 105                 110

<210> SEQ ID NO 30
<211> LENGTH: 11
<212> TYPE: PRT
<213> ORGANISM: Homo sapiens

<400> SEQUENCE: 30

Arg Ala Ser Gln Gly Ile Asn Asn Tyr Leu Ala
1               5                   10

<210> SEQ ID NO 31
<211> LENGTH: 7
<212> TYPE: PRT
<213> ORGANISM: Homo sapiens

<400> SEQUENCE: 31
```

```
Ala Ala Ser Thr Leu Gln Ser
1               5

<210> SEQ ID NO 32
<211> LENGTH: 9
<212> TYPE: PRT
<213> ORGANISM: Homo sapiens

<400> SEQUENCE: 32

Gln Gln Leu Asp Ser Tyr Pro Arg Thr
1               5

<210> SEQ ID NO 33
<211> LENGTH: 120
<212> TYPE: PRT
<213> ORGANISM: Homo sapiens

<400> SEQUENCE: 33

Glu Val Gln Leu Leu Glu Ser Gly Gly Gly Leu Ala Gln Pro Gly Gly
1               5                   10                  15

Ser Leu Arg Leu Ser Cys Ala Ala Ser Gly Phe Ser Phe Asn Thr Tyr
            20                  25                  30

Leu Met His Trp Val Arg Gln Ala Pro Gly Lys Gly Leu Glu Trp Val
        35                  40                  45

Ser Ala Ile Ser Gly Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Arg Ile Pro Val Ala Pro Phe Asp Tyr Trp Gly Gln
            100                 105                 110

Gly Thr Leu Val Thr Val Ser Ser
        115                 120

<210> SEQ ID NO 34
<211> LENGTH: 5
<212> TYPE: PRT
<213> ORGANISM: Homo sapiens

<400> SEQUENCE: 34

Thr Tyr Leu Met His
1               5

<210> SEQ ID NO 35
<211> LENGTH: 17
<212> TYPE: PRT
<213> ORGANISM: Homo sapiens

<400> SEQUENCE: 35

Ala Ile Ser Gly Gly Gly Gly Asn Thr Tyr Tyr Ala Asp Ser Val Lys
1               5                   10                  15

Gly

<210> SEQ ID NO 36
<211> LENGTH: 11
<212> TYPE: PRT
<213> ORGANISM: Homo sapiens

<400> SEQUENCE: 36
```

```
Glu Asn Arg Ile Pro Val Ala Pro Phe Asp Tyr
1               5                   10
```

<210> SEQ ID NO 37
<211> LENGTH: 107
<212> TYPE: PRT
<213> ORGANISM: Homo sapiens

<400> SEQUENCE: 37

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Leu Ala Thr Tyr Tyr Cys Gln Gln Tyr Asn Ser Phe Ser Trp
                85                  90                  95

Thr Phe Gly Gln Gly Thr Lys Val Glu Ile Lys
            100                 105
```

<210> SEQ ID NO 38
<211> LENGTH: 11
<212> TYPE: PRT
<213> ORGANISM: Homo sapiens

<400> SEQUENCE: 38

```
Arg Ala Ser Gln Ser Ile Ser Thr Trp Leu Ala
1               5                   10
```

<210> SEQ ID NO 39
<211> LENGTH: 7
<212> TYPE: PRT
<213> ORGANISM: Homo sapiens

<400> SEQUENCE: 39

```
Lys Ala Ser Ser Leu Glu Ser
1               5
```

<210> SEQ ID NO 40
<211> LENGTH: 9
<212> TYPE: PRT
<213> ORGANISM: Homo sapiens

<400> SEQUENCE: 40

```
Gln Gln Tyr Asn Ser Phe Ser Trp Thr
1               5
```

<210> SEQ ID NO 41
<211> LENGTH: 125
<212> TYPE: PRT
<213> ORGANISM: Homo sapiens

<400> SEQUENCE: 41

```
Gln Val Gln Leu Gln Gln Ser Gly Pro Gly Leu Val Asn Pro Ser Gln
1               5                   10                  15

Thr Leu Ser Leu Thr Cys Ala Ile Ser Gly Asp Ser Val Ser Ser Asn
            20                  25                  30
```

Ser Gly Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Gly
 50                  55                  60

Ile Ser Val Gln Ser Arg Ile Thr Ile Asn Pro Asp Thr Ser Lys Asn
 65                  70                  75                  80

His Phe Ser Leu Gln Leu Asn Ser Val Thr Pro Glu Asp Thr Ala Val
                 85                  90                  95

Tyr Tyr Cys Ala Arg Asp Pro Tyr Tyr Gly Ser Gly Ser Tyr Phe
                100                 105                 110

Asp Tyr Trp Gly Gln Gly Thr Leu Val Thr Val Ser Ser
        115                 120                 125

<210> SEQ ID NO 42
<211> LENGTH: 7
<212> TYPE: PRT
<213> ORGANISM: Homo sapiens

<400> SEQUENCE: 42

Ser Asn Ser Gly Ala Trp Asn
1               5

<210> SEQ ID NO 43
<211> LENGTH: 18
<212> TYPE: PRT
<213> ORGANISM: Homo sapiens

<400> SEQUENCE: 43

Arg Thr Tyr Tyr Arg Ser Lys Trp Tyr Asn Asp Tyr Gly Ile Ser Val
1               5                   10                  15

Gln Ser

<210> SEQ ID NO 44
<211> LENGTH: 13
<212> TYPE: PRT
<213> ORGANISM: Homo sapiens

<400> SEQUENCE: 44

Asp Pro Tyr Tyr Tyr Gly Ser Gly Ser Tyr Phe Asp Tyr
1               5                   10

<210> SEQ ID NO 45
<211> LENGTH: 107
<212> TYPE: PRT
<213> ORGANISM: Homo sapiens

<400> SEQUENCE: 45

Glu Ile Val Met Thr Gln Ser Pro Ala Thr Leu Ser Val Ser Pro Gly
1               5                   10                  15

Glu Arg Val Thr Leu Ser Cys Arg Ala Ser Leu Ser Val Asn Ser Asn
                20                  25                  30

Leu Ala Trp Tyr Gln Gln Lys Pro Gly Gln Ala Pro Arg Leu Leu Ile
         35                  40                  45

Tyr Asp Thr Ser Thr Arg Ala Thr Gly Val Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr His Tyr Trp Pro Leu
                 85                  90                  95

```
Thr Phe Gly Gly Gly Thr Lys Val Glu Ile Lys
                100                 105
```

```
<210> SEQ ID NO 46
<211> LENGTH: 11
<212> TYPE: PRT
<213> ORGANISM: Homo sapiens

<400> SEQUENCE: 46

Arg Ala Ser Leu Ser Val Asn Ser Asn Leu Ala
1               5                   10
```

```
<210> SEQ ID NO 47
<211> LENGTH: 8
<212> TYPE: PRT
<213> ORGANISM: Homo sapiens

<400> SEQUENCE: 47

Tyr Asp Thr Ser Thr Arg Ala Thr
1               5
```

```
<210> SEQ ID NO 48
<211> LENGTH: 9
<212> TYPE: PRT
<213> ORGANISM: Homo sapiens

<400> SEQUENCE: 48

Gln Gln Tyr His Tyr Trp Pro Leu Thr
1               5
```

```
<210> SEQ ID NO 49
<211> LENGTH: 127
<212> TYPE: PRT
<213> ORGANISM: Homo sapiens

<400> SEQUENCE: 49

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Tyr Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Ile Thr Leu Val Arg Gly Ala Asp Tyr Tyr Tyr Asn Tyr
            100                 105                 110

Asp Met Asp Val Trp Gly Gln Gly Thr Thr Val Thr Val Ser Ser
        115                 120                 125
```

```
<210> SEQ ID NO 50
<211> LENGTH: 5
<212> TYPE: PRT
<213> ORGANISM: Homo sapiens

<400> SEQUENCE: 50

Tyr Tyr Gly Met His
1               5
```

<210> SEQ ID NO 51
<211> LENGTH: 17
<212> TYPE: PRT
<213> ORGANISM: Homo sapiens

<400> SEQUENCE: 51

Val Ile Trp Tyr Asp Gly Ser Asn Lys Tyr Tyr Ala Asp Ser Val Lys
1               5                   10                  15

Gly

<210> SEQ ID NO 52
<211> LENGTH: 18
<212> TYPE: PRT
<213> ORGANISM: Homo sapiens

<400> SEQUENCE: 52

Gly Ile Thr Leu Val Arg Gly Ala Asp Tyr Tyr Tyr Asn Tyr Asp Met
1               5                   10                  15

Asp Val

<210> SEQ ID NO 53
<211> LENGTH: 112
<212> TYPE: PRT
<213> ORGANISM: Homo sapiens

<400> SEQUENCE: 53

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 54
<211> LENGTH: 16
<212> TYPE: PRT
<213> ORGANISM: Homo sapiens

<400> SEQUENCE: 54

Arg Ser Ser Gln Ser Leu Leu His Ser Asn Gly Tyr Asn Tyr Leu Asp
1               5                   10                  15

<210> SEQ ID NO 55
<211> LENGTH: 8
<212> TYPE: PRT
<213> ORGANISM: Homo sapiens

<400> SEQUENCE: 55

Tyr Leu Gly Ser Asn Arg Ala Ser
1               5

<210> SEQ ID NO 56

<211> LENGTH: 9
<212> TYPE: PRT
<213> ORGANISM: Homo sapiens

<400> SEQUENCE: 56

Met Gln Ala Leu Gln Thr Pro Leu Thr
1               5

<210> SEQ ID NO 57
<211> LENGTH: 369
<212> TYPE: DNA
<213> ORGANISM: Homo sapiens

<400> SEQUENCE: 57

| | | |
|---|---|---|
| caggtgcagc tgcaggagtc gggcccagga ctggtgaagc cttcggggac cctgtccctc | 60 |
| acctgcgctg tctctggtgg ctccatcagc actagtaatt ggtggagttg ggtccgccag | 120 |
| cccccaggga aggggctgga gtggattggg gaaatctatc acagtgggag catcaactac | 180 |
| aacccgtccc tcaagagtcg agtcaccata tcagtagaca ggtccaagaa ccagttctcc | 240 |
| ctgaagctga gctctgtgac cgccgcggac acggccgtgt attactgtgc gagagatcac | 300 |
| tatggttcgg ggagttatta taacggtatg gacgtctggg gccaagggac cacggtcacc | 360 |
| gtctcttca | 369 |

<210> SEQ ID NO 58
<211> LENGTH: 336
<212> TYPE: DNA
<213> ORGANISM: Homo sapiens

<400> SEQUENCE: 58

| | | |
|---|---|---|
| gatattgtga tgactcagtc tccactctcc ctgcccgtca cccctggaga gccggcctcc | 60 |
| atctcctgca ggtctagtca gagcctcctg tatagtgatg gatacaacta tttggattgg | 120 |
| tacctgcaga agccagggca gtctccacag ctcctgatct atttgggttc taatcgggcc | 180 |
| tccggggtcc ctgacaggtt cagtggcagt ggatcaggca cagattttac actgacaatc | 240 |
| agcagagtgg aggctgagga tgttggggtt tattactgca tgcaagctcg acaaactccg | 300 |
| tggacgttcg gccaagggac caaggtggaa atcaaa | 336 |

<210> SEQ ID NO 59
<211> LENGTH: 342
<212> TYPE: DNA
<213> ORGANISM: Homo sapiens

<400> SEQUENCE: 59

| | | |
|---|---|---|
| caggtgcagc tggtggagtc tgggggaggc gtggtccagc ctggagggtc cctgagactc | 60 |
| tcctgtgcag cgtctggatt caccttcagt gactatggct tcactgggt ccgccaggct | 120 |
| ccaggcaagg gtctggagtg ggtggcagtt atttggtatg atggaagtaa tgaatactat | 180 |
| acagactccg tgaagggccg attcaccatc tccagagaca attccaagaa cacgctgtat | 240 |
| ctgcaaatga acagtctgag agccgaggat acggctatgt atttctgtgt ggttaatcct | 300 |
| tttgactatt ggggccaggg aaccctggtc actgtctcct ca | 342 |

<210> SEQ ID NO 60
<211> LENGTH: 321
<212> TYPE: DNA
<213> ORGANISM: Homo sapiens

<400> SEQUENCE: 60

```
gacatccaga tgacccagtc tccatcctcc ctgtctgcat tgttggaga cagagtcacc    60 atcacttgcc gggcgagtca gggcattaac cattatttag cctggtatca acaaaaacca   120
gggaaagctc caaacctcct catccttgct gcatctactt tgctatcagg ggtcccatct   180
cggttcggtg gcagaggatc tgggacagat ttcactctca tcatcagcag cctgcagcct   240
gaagatgttg caacttacta ctgtcaaaaa tatgacagtg ccccgtacac ttttggccag   300
gggaccaagc tggagatcaa a                                             321

<210> SEQ ID NO 61
<211> LENGTH: 321
<212> TYPE: DNA
<213> ORGANISM: Homo sapiens

<400> SEQUENCE: 61
gacatccaga tgacccagtc tccatcctcc ctgtctgcat tgttggaga cagagtcacc    60 atcacttgcc gggcgagtca gggcattaac cattatttag cctggtatca acaaaaacca   120
gggaaagctc caaacctcct catccttgct gcatctactt tgctatcagg ggtcccatct   180
cggttcggtg gcagaggatc tgggacagat ttcactctca tcatcagcag cctgcagcct   240
gaagatgttg caacttacta ctgtcaaaaa tatgacagtg ccccgtacac ttttggccag   300
gggaccaagc tggagatcaa a                                             321

<210> SEQ ID NO 62
<211> LENGTH: 321
<212> TYPE: DNA
<213> ORGANISM: Homo sapiens

<400> SEQUENCE: 62
gaaattgtgt tgacacagtc tccagccacc ctgtctttgt ctccagggga aagagccacc    60
ctctcctgca gggccagtca gagtgttagc agctacttag cctggtacca gcagaaacct   120
ggccaggctc ccaggctcct catctatgat gcatccaaga gggccactgg catcccagcc   180
aggttcagtg gcagtgggtc tgggacagac ttcactctca ccatcagcag cctagagcct   240
gaagattttg cagtttatta ctgtcagcag cgtaacaact ggccgctcac tttcggcgga   300
gggaccaagg tggagatcaa a                                             321

<210> SEQ ID NO 63
<211> LENGTH: 357
<212> TYPE: DNA
<213> ORGANISM: Homo sapiens

<400> SEQUENCE: 63
caggtgcagc tgcaggagtc gggcccagga ctggtgaagc cttcggagac cctgtccctc    60
acctgcgctg tctctggtca ctccatcaga ggtagttact tctggggctg gatccggcag   120
cccccaggga gggcctgga gtggattggg agtatctatc atagtgggag tacctacaca   180
aatccgtccc tcaagagtcg agccaccata tcagtagaca cgtccaagaa tcagttctcc   240
ctgaagctga actctgtgac cgccgcagac acggccgtgt attactgtgc gagagatctg   300
gatatagcga ctacgcgaga ctactggggc cagggaaccc tggtcaccgt ctcctca     357

<210> SEQ ID NO 64
<211> LENGTH: 321
<212> TYPE: DNA
<213> ORGANISM: Homo sapiens

<400> SEQUENCE: 64
```

```
gacatccagt tgacccagtc tccatccttc ctgtctgcat ctgtaggaga cagagtcacc    60
atcatttgtc gggccagtca gggcattaac aattatttag cctggtatca gcaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240
gaagattttg caacttatta ctgtcaacag cttgatagtt accctcggac gttcggccaa   300
gggaccaagg tggaaatcaa a                                              321
```

```
<210> SEQ ID NO 65
<211> LENGTH: 360
<212> TYPE: DNA
<213> ORGANISM: Homo sapiens

<400> SEQUENCE: 65
gaggtgcaac tgttggagtc tgggggaggc ttggcacagc ctgggggggtc cctgagactc    60 tcctgtgcag cctctggatt ctcctttaac acctatctca tgcactgggt ccgccaggct   120
ccagggaagg ggctggagtg ggtctcagct attagtggtg gtggtggtaa cacatactac   180
gcagactccg tgaagggccg gttcaccatc tccagagaca attccaagaa cacgctgtat   240
ctgcaaatga acagcctgag agccgaggac acggccgttt attactgtgc gaaagaaaac   300
cgtatcccag tggccccctt tgactactgg ggccagggaa ccctggtcac cgtctcctca   360
```

```
<210> SEQ ID NO 66
<211> LENGTH: 321
<212> TYPE: DNA
<213> ORGANISM: Homo sapiens

<400> SEQUENCE: 66
gacatccaga tgacccagtc tccttccacc ctgtctgcat ctgtaggaga cagagtcacc    60
atcacttgcc gggccagtca gagtattagt acctggttgg cctggtatca acagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgatcttg caacttatta ctgccaacag tataatagtt tttcgtggac gttcggccaa   300
gggaccaagg tggaaatcaa a                                              321
```

```
<210> SEQ ID NO 67
<211> LENGTH: 375
<212> TYPE: DNA
<213> ORGANISM: Homo sapiens

<400> SEQUENCE: 67
caagtacagc tgcagcagtc aggtccagga ctggtgaacc cctcgcagac cctctcactc    60
acctgtgcca tctccgggga cagtgtctct agcaacagtg gtgcttggaa ctggatcagg   120
cagtccccat cgagaggcct tgagtggctg ggaaggacat actacaggtc caagtggtat   180
aatgattatg gaatatctgt gcaaagtcga ataaccatca cccagacac atccaagaac    240 cacttctccc tgcagctgaa ttctgtgact cccgaggaca cggctgtgta ttactgtgca   300
agagatccct attactatgg ttcggggagt tactttgact actggggcca gggaaccctg   360
gtcaccgtct cctca                                                    375
```

```
<210> SEQ ID NO 68
<211> LENGTH: 321
<212> TYPE: DNA
```

<213> ORGANISM: Homo sapiens

<400> SEQUENCE: 68

| | |
|---|---:|
| gaaatagtga tgacgcagtc tccagccacc ctgtctgtat ctccagggga aagagtcacc | 60 |
| ctctcctgca gggccagtct gagtgttaac agcaacttag cctggtacca gcagaaacct | 120 |
| ggccaggctc ccaggctcct catctatgat acatccacca gggccactgg tgtcccagcc | 180 |
| aggttcagtg gcagtgggtc tgggacagag ttcactctca ccatcagcag cctgcagtct | 240 |
| gaagattttg cagtttatta ctgtcagcag tatcattact ggccgctcac tttcggcggc | 300 |
| gggaccaagg tggagatcaa a | 321 |

<210> SEQ ID NO 69
<211> LENGTH: 381
<212> TYPE: DNA
<213> ORGANISM: Homo sapiens

<400> SEQUENCE: 69

| | |
|---|---:|
| caggtgcagc tggtggagtc tgggggaggc gtggtccagc ctgggaggtc cctgagactc | 60 |
| tcctgtgcag cgtctggatt cagtttcagt tactatggca tgcactgggt ccgccaggct | 120 |
| ccaggcaagg ggctggagtg gtggcagtt atatggtatg atggaagtaa taaatactat | 180 |
| gcagactccg tgaagggccg attcaccatc tccagagaca attccaagaa cacgttgtat | 240 |
| ctgcaaatga acagcctgag agccgaggac acggctgtgt attactgtgc gagtggtatt | 300 |
| actctggttc ggggagccga ttactattac aactacgata tggacgtctg gggccaaggg | 360 |
| accacggtca ccgtctcctc a | 381 |

<210> SEQ ID NO 70
<211> LENGTH: 336
<212> TYPE: DNA
<213> ORGANISM: Homo sapiens

<400> SEQUENCE: 70

| | |
|---|---:|
| gatattgtga tgactcagtc tccactctcc ctgcccgtca cccctggaga gccggcctcc | 60 |
| atctcctgca ggtctagtca gagcctcctg catagtaatg gatacaacta tttggattgg | 120 |
| tacctgcaga agccagggca gtctccacag ctcctgatct atttgggttc taatcgggcc | 180 |
| tccggggtcc ctgacaggtt cagtggcagt ggatcaggca cagattttac actgaaaatc | 240 |
| agcagagtgg aggctgagga tgttggggtt tattactgca tgcaagctct acaaactccc | 300 |
| ctcactttcg gcggagggac caaggtggag atcaaa | 336 |

<210> SEQ ID NO 71
<211> LENGTH: 143
<212> TYPE: PRT
<213> ORGANISM: Homo sapiens

<400> SEQUENCE: 71

Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg

```
                65                  70                  75                  80
Asp Phe His Met Ser Val Val Arg Ala Arg Arg Asn Asp Ser Gly Thr
                    85                  90                  95

Tyr Leu Cys Gly Ala Ile Ser Leu Ala Pro Lys Ala Gln Ile Lys Glu
                    100                 105                 110

Ser Leu Arg Ala Glu Leu Arg Val Thr Glu Arg Arg Ala Glu Val Pro
                    115                 120                 125

Thr Ala His Pro Ser Pro Ser Pro Arg Pro Ala Gly Gln Phe Gln
                130                 135                 140

<210> SEQ ID NO 72
<211> LENGTH: 288
<212> TYPE: PRT
<213> ORGANISM: Homo sapiens

<400> SEQUENCE: 72

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
            50                  55                  60

Leu Asn Trp Tyr Arg Met Ser Pro Ser Asn Gln Thr Asp Lys Leu Ala
65              70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285

<210> SEQ ID NO 73
<211> LENGTH: 948
```

```
<212> TYPE: DNA
<213> ORGANISM: Homo sapiens

<400> SEQUENCE: 73
gcctgagcag tggagaaggc ggcactctgg tggggctgct ccaggcatgc agatcccaca      60
ggcgccctgg ccagtcgtct gggcggtgct acaactgggc tggcggccag gatggttctt     120
agactcccca gacaggccct ggaacccccc caccttctcc ccagccctgc tcgtggtgac     180
cgaaggggac aacgccacct tcacctgcag cttctccaac acatcggaga gcttcgtgct     240
aaactggtac cgcatgagcc cagcaacca gacggacaag ctggccgctt ccccgagga      300
ccgcagccag cccggccagg actgccgctt ccgtgtcaca caactgccca cgggcgtga     360
cttccacatg agcgtggtca gggcccggcg caatgacagc ggcacctacc tctgtggggc     420
catctccctg gcccccaagg cgcagatcaa agagagcctg cgggcagagc tcaggggtgac     480
agagagaagg gcagaagtgc ccacagccca ccccagcccc tcacccaggc agccggcca     540
gttccaaacc ctggtggttg tgtcgtgggc cggcctgctg ggcagcctgg tgctgctagt     600
ctgggtcctg gccgtcatct gctcccgggc cgcacgaggg acaataggag ccaggcgcac     660
cggccagccc ctgaaggagg acccctcagc cgtgcctgtg ttctctgtgg actatgggga     720
gctggatttc cagtggcgag agaagacccc ggagccccc gtgccctgtg tccctgagca     780
gacggagtat gccaccattg tctttcctag cggaatgggc acctcatccc ccgcccgcag     840
gggctcagcc gacggccctc ggagtgccca gccactgagg cctgaggatg acactgctc     900
ttggccctc tgaccggctt ccttggccac cagtgttctg cagaccct                   948

<210> SEQ ID NO 74
<211> LENGTH: 984
<212> TYPE: DNA
<213> ORGANISM: Artificial Sequence
<220> FEATURE:
<223> OTHER INFORMATION: human IgG4 constant region with a S228P
      mutation

<400> SEQUENCE: 74
gctagcacca agggcccttc cgtgttccct ctggccccctt gctcccggtc cacctccgag     60
tccaccgccg ctctgggctg tctggtgaag gactacttcc ctgagcctgt gaccgtgagc    120
tggaactctg gcgccctgac ctccggcgtg cacaccttcc ctgccgtgct gcagtcctcc    180
ggcctgtact ccctgtcctc cgtggtgacc gtgccttcct cctccctggg caccaagacc    240
tacacctgca acgtggacca caagccttcc aacaccaagg tggacaagcg ggtggagtcc    300
aagtacggcc ctccttgccc tccctgccct gccctgagt tcctgggcgg acctccgtg     360
ttcctgttcc ctcctaagcc taaggacacc ctgatgatct cccggacccc tgaggtgacc    420
tgcgtggtgg tggacgtgtc ccaggaagat cctgaggtcc agttcaattg gtacgtggat    480
ggcgtggagg tgcacaacgc caagaccaag cctcgggagg aacagttcaa ctccacctac    540
cgggtggtgt ctgtgctgac cgtgctgcac caggactggc tgaacggcaa ggaatacaag    600
tgcaaggtca gcaacaaggg cctgccctcc tccatcgaga aaccatctc caaggccaag    660
ggccagcctc gcgagcctca ggtgtacacc ctgcctccta gccaggaaga gatgaccaag    720
aatcaggtgt ccctgacatg cctggtgaag ggcttctacc cttccgatat cgccgtggag    780
tgggagagca acggccagcc agagaacaac tacaagacca cccctcctgt gctggactcc    840
gacggctcct tcttcctgta ctccaggctg accgtggaca gtccggtg caggaaggc    900
aacgtctttt cctgctccgt gatgcacgag gccctgcaca accactacac ccagaagtcc    960
```
ctgtccctgt ctctgggcaa gtga                                                  984

<210> SEQ ID NO 75
<211> LENGTH: 327
<212> TYPE: PRT
<213> ORGANISM: Artificial Sequence
<220> FEATURE:
<223> OTHER INFORMATION: human IgG4 constant region with a S228P mutation

<400> SEQUENCE: 75

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 76

```
<211> LENGTH: 324
<212> TYPE: DNA
<213> ORGANISM: Artificial Sequence
<220> FEATURE:
<223> OTHER INFORMATION: human antibody light chain kappa constant
      region

<400> SEQUENCE: 76
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttga                                          324

<210> SEQ ID NO 77
<211> LENGTH: 107
<212> TYPE: PRT
<213> ORGANISM: Artificial Sequence
<220> FEATURE:
<223> OTHER INFORMATION: human antibody light chain kappa constant
      region

<400> SEQUENCE: 77

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

ANTI-PD-1 ANTIBODIES AND USES THEREOF

CROSS-REFERENCE TO RELATED APPLICATION

This application is a Section 371 of International Application No. PCT/CN2016/091962, filed Jul. 27, 2016, which was published in the English language on Feb. 2, 2017 under International Publication No. WO 2017/016497 A1, and claims priority under 35 U.S.C. § 119(b) to Chinese Application No. 201510451773.6, filed Jul. 28, 2015, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing File," a creation date of Jan. 25, 2018, and having a size of about 39 kb. The sequence listing submitted via EFS-Web is part of the specification and is herein incorporated by reference in its entirety.

FIELD OF THE INVENTION

The invention relates to monoclonal anti-PD-1 antibodies, nucleic acids and expression vectors encoding the antibodies, recombinant cells containing the vectors, and compositions comprising the antibodies. Methods of making the antibodies, and methods of using the antibodies to treat diseases including cancer and autoimmune diseases are also provided.

BACKGROUND OF THE INVENTION

Tumor cells are able to evade the immune system by "editing" host immunity in the tumor microenvironment in a variety of ways. One way in which tumors carry out this so-called "cancer immune escape" is by up regulating the expression of immune checkpoint proteins, which are key regulators of the immune system, thus suppressing the immune response. One such immunosuppressive co-signal is mediated by the PD-1 receptor and its ligand PD-L1.

PD-1 (Programmed Cell Death Protein 1) is a type I transmembrane protein that is 288 amino acids long and is one of the major immune checkpoint molecules (Blank et al., 2005, Cancer Immunotherapy, 54:307-314). PD-1 is primarily expressed on activated T cells, and it interacts with the ligands PD-L1 and PD-L2 to induce an inhibitory signal resulting in reduced T cell proliferation, cytokine production, and cytotoxic activity (Freeman et al., 2000, J. Exp. Med., 192:1027-34). PD-L1 is expressed on many cell types, including T, B, endothelial, epithelial, and antigen presenting cells, on cells of lung, liver and heart tissues, and on several types of tumor cells. In contrast, PD-L2 is narrowly expressed on professional antigen presenting cells, such as dendritic cells and macrophages.

The interaction between PD-1 and PD-L1 is critical for modulating the immune response, and it is the predominant mechanism by which PD-L1-expressing tumor cells escape from immune surveillance (Zippelius et al., 2015, Cancer Immunol Res., 3(3):236-44). Persistent expression of PD-1 by T cells is highly indicative of an exhausted phenotype, noted by a decrease in effector function. This phenotype has been observed in various types of tumor-infiltrating lymphocyte (TIL) and linked to poor prognosis and tumor recurrence (Wherry, 2011, Nat. Immunol., 12:492-99).

Blocking of the PD-1/PD-L1 interaction can activate the immune system and enhance antitumor immune responses, and it has been demonstrated that in multiple syngeneic mouse tumor models, blockade of PD-1 or its ligands promotes antitumor activity (Hirano et al., 2005, Cancer Res., 65:1089-96). Thus, the interaction between PD-1 and PD-L1 is an attractive target for cancer immunotherapy.

Cancer immunotherapy, a recent breakthrough in cancer treatment, employs a patient's own immune system to attack tumor cells. Inhibitors of immune checkpoint proteins have the potential to treat a variety of tumor types, such as metastatic melanoma, lung cancer, breast cancer, renal cell carcinoma, etc. Recent studies using cancer immunotherapy approaches have shown promising results, especially in the case of metastatic carcinomas (Weinstock and McDermott, 2015, TherAdv Urol., 7(6):365-77). In addition, cancer immunotherapy has shown great potential in the treatment of blood cancers, including Hodgkin's lymphoma, multiple myeloma, bone marrow dysplasia syndrome, non-Hodgkin's lymphoma, etc. (Zou and Chen L, 2008, Nat Rev Immunol., 8(6):467-77). Side effects caused by immune checkpoint inhibitors are negligible, reversible and manageable, and an effective immune checkpoint inhibitor may substantially improve the overall survival of cancer patients Immune checkpoint inhibitors can be used in combination with targeted therapy or conventional radiotherapy and chemotherapy, and such combinatorial therapy may be effective in the treatment of many types of cancer. Clinical trials of anti-PD-1 monoclonal antibodies have been initiated by BMS, Merck, MedImmune and CureTech, including, for example, three trials at the market stage; and clinical trials of anti-PD-L1 mAbs have also been initiated by Roche, MedImmune, Merck Serono and BMS, including, for example, three trials that have been withdrawn or terminated (clinicaltrials.gov, 2015).

Phase I clinical trials of a fully human IgG4 mAb from BMS, Nivolumab (Opdivo®), have been carried out. The first of those trials, carried out in 2010, was conducted in 39 patients with advanced solid tumors (Brahmer et al., 2010, J. Clin. Oncol., 28:3167-75). The response was 3/39, with mostly immune-related adverse effects (AEs) and one serious AE. The second trial, carried out in 2012, was conducted in 294 patients (Topalian et al., 2014, J. Clin. Oncol., 32:1020-30). There were objective responses in 16% of the non-small cell lung cancer patients, 28% of the metastatic melanoma patients, 29% of the renal cell cancer patients, and 0% of the castrate-resistant prostate cancer or colorectal cancer patients. Grade 3/4 treatment-related AEs occurred in 15% of patients, and there were three deaths.

Thus, despite the progress, there is a need in the art for more effective therapeutics comprising anti-PD-1 antibodies that effectively inhibit the PD-1/PD-L1 signaling activity while causing minimal adverse side effects in humans.

BRIEF SUMMARY OF THE INVENTION

The invention satisfies this need by providing monoclonal antibodies that specifically bind PD-1 with high affinity and induce the secretion of IFN-γ and IL-2 by immune cells, as measured in both a mixed lymphocyte reaction and a T lymphocyte stimulation assay. In particular, the fully human anti-PD-1 antibodies of the invention have a higher affinity to PD-1 than Nivolumab. Additionally, the antibodies demonstrate comparable characteristics to Pembrolizumab (Keytruda®, Merck), a humanized IgG4 anti-PD-1 mAb, but are predicted to have fewer immunogenic adverse side effects in humans than Pembrolizumab due to the fact that they are fully human, rather than simply humanized mAbs.

In one general aspect, the invention relates to isolated monoclonal antibodies or antigen-binding fragments thereof that bind PD-1.

According to a particular aspect, the invention relates to an isolated monoclonal antibody or antigen-binding fragment thereof comprising LCDR1, LCDR2, LCDR3, HCDR1, HCDR2 and HCDR3, having the polypeptide sequences of:
  (1) SEQ ID NOs: 30, 31, 32, 26, 27, and 28, respectively;
  (2) SEQ ID NOs: 6, 7, 8, 2, 3, and 4, respectively;
  (3) SEQ ID NOs: 14, 15, 16, 10, 11, and 12, respectively;
  (4) SEQ ID NOs: 22, 23, 24, 18, 19, and 20, respectively;
  (5) SEQ ID NOs: 38, 39, 40, 34, 35, and 36, respectively;
  (6) SEQ ID NOs: 46, 47, 48, 42, 43, and 44, respectively; or
  (7) SEQ ID NOs: 54, 55, 56, 50, 51, and 52, respectively;
  wherein the antibody or antigen-binding fragment thereof binds PD-1, preferably binds specifically to human PD-1.

According to another particular aspect, the invention relates to an isolated monoclonal antibody or antigen-binding fragment thereof, comprising a heavy chain variable region having a polypeptide sequence at least 95% identical to SEQ ID NO: 25, 1, 9, 17, 33, 41 or 49, or a light chain variable region having a polypeptide sequence at least 95% identical to SEQ ID NO: 29, 5, 13, 21, 37, 45 or 53.

According to one embodiment, the isolated monoclonal antibody or antigen-binding fragment thereof of the invention is human/rat chimeric.

According to another embodiment, the isolated monoclonal antibody or antigen-binding fragment thereof of the invention is human.

According to yet another embodiment, the isolated monoclonal antibody or antigen-binding fragment thereof of the invention further comprises a constant region, preferably a human heavy chain IgG4 constant region, more preferably a human heavy chain IgG4 constant region having one or more mutations, such as a S228P mutation, and a human antibody light chain kappa constant region.

In another general aspect, the invention relates to an isolated nucleic acid encoding a monoclonal antibody or antigen-binding fragment thereof of the invention.

In another general aspect, the invention relates to a vector comprising an isolated nucleic acid encoding a monoclonal antibody or antigen-binding fragment thereof of the invention.

In another general aspect, the invention relates to a host cell comprising an isolated nucleic acid encoding a monoclonal antibody or antigen-binding fragment thereof of the invention.

In another general aspect, the invention relates to a pharmaceutical composition, comprising an isolated monoclonal antibody or antigen-binding fragment thereof of the invention and a pharmaceutically acceptable carrier.

In another general aspect, the invention relates to a method of blocking the binding of PD-1 to PD-L1 or PD-L2, or a method of augmenting secretion of IFN-γ and IL-2, in a subject in need thereof, comprising administering to the subject a pharmaceutical composition of the invention.

In another general aspect, the invention relates to a method of treating a disease, disorder or condition, preferably an infectious disease, an inflammatory disease, an immune disease, an autoimmune disease, or a graft versus host disease in a subject in need thereof, comprising administering to the subject a pharmaceutical composition of the invention.

In another general aspect, the invention relates to a method of treating a hyperproliferative disease in a subject in need thereof, comprising administering to the subject a pharmaceutical composition of the invention. The hyperproliferative disease can be a non-malignant disease, including but not limited to, atherosclerosis, benign hyperplasia, benign prostatic hypertrophy. The hyperproliferative disease can also be a tumor, or a malignant disease. The tumor can be selected from the group consisting of a solid tumor, a hematologic cancer, bladder cancer, biliary cancer, brain cancer, breast cancer, colon cancer, esophageal cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer.

In another general aspect, the invention relates to a method of producing a monoclonal antibody or antigen-binding fragment thereof of the invention, comprising culturing a cell comprising a nucleic acid encoding the monoclonal antibody or antigen-binding fragment under conditions to produce the monoclonal antibody or antigen-binding fragment thereof, and recovering the antibody or antigen-binding fragment thereof from the cell or cell culture.

In another general aspect, the invention relates to a method of producing a pharmaceutical composition comprising a monoclonal antibody or antigen-binding fragment thereof of the invention, comprising combining the monoclonal antibody or antigen-binding fragment thereof with a pharmaceutically acceptable carrier to obtain the pharmaceutical composition.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings.

DETAILED DESCRIPTION OF THE INVENTION

Figure 1:
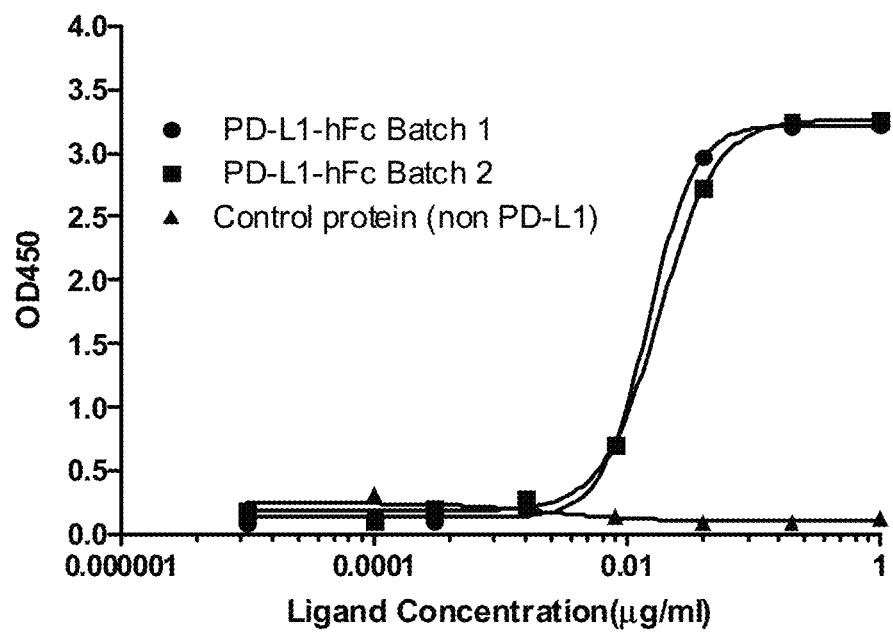
FIG. 1 shows the binding activity of PD-1-hFc protein to biotin-labeled PD-L1-hFc.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical value, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

The invention generally relates to isolated anti-PD-1 antibodies, nucleic acids and expression vectors encoding the antibodies, recombinant cells containing the vectors, and compositions comprising the antibodies. Methods of making the antibodies, and methods of using the antibodies to treat diseases including cancer and autoimmune diseases are also provided. The antibodies of the invention possess one or more desirable functional properties, including but not limited to high-affinity binding to PD-1, high specificity to PD-1, the ability to block the binding of PD-1 to its ligand PD-L1 and PD-L2, and the ability to stimulate secretion of the cytokines IFN-γ and IL-2.

In a general aspect, the invention relates to isolated monoclonal antibodies or antigen-binding fragments thereof that bind PD-1.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., CDR1, CDR2, and CDR3). The light chain variable region domains are alternatively referred to as LCDR1, LCDR2 and LCRD3, and the heavy chain variable region domains are alternatively referred to as HCDR1, HCRD2 and HCDR3.

As used herein, the term an "isolated antibody" refers to an antibody which is substantially free of other antibodies having different antigenic specificities (e.g., an isolated antibody that specifically binds to PD-1 is substantially free of antibodies that do not bind to PD-1). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi-specific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the constant region of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "PD-1" refers to the Programmed Cell Death 1 protein, a 50-55 kDa type I transmembrane receptor that is expressed on activated T, B, and myeloid lineage cells (Greenwald et al., 2005, Annu. Rev. Immunol. 23:515-48; Sharpe et al., 2007, Nat. Immunol. 8:239-45). The amino acid sequence of human PD-1 is represented in GenBank Accession No. NP_005009.2. Two ligands for PD-1 have been identified, PD-L1 and PD-L2.

As used herein, an antibody that "specifically binds to PD-1" refers to an antibody that binds to a PD-1, preferably a human PD-1, with a KD of $1\times10^{-7}$M or less, preferably $1\times10^{-8}$M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as a Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising LCDR1, LCDR2, LCDR3, HCDR1, HCDR2 and HCDR3, having the polypeptide sequences of:
(1) SEQ ID NOs: 30, 31, 32, 26, 27, and 28, respectively;
(2) SEQ ID NOs: 6, 7, 8, 2, 3, and 4, respectively;
(3) SEQ ID NOs: 14, 15, 16, 10, 11, and 12, respectively;
(4) SEQ ID NOs: 22, 23, 24, 18, 19, and 20, respectively;
(5) SEQ ID NOs: 38, 39, 40, 34, 35, and 36, respectively;
(6) SEQ ID NOs: 46, 47, 48, 42, 43, and 44, respectively; or
(7) SEQ ID NOs: 54, 55, 56, 50, 51, and 52, respectively;
wherein the antibody or antigen-binding fragment thereof binds PD-1, preferably specifically binds to human PD-1.

According to another particular aspect, the invention relates to an isolated monoclonal antibody or antigen-binding fragment thereof of the invention, comprising a heavy chain variable region having a polypeptide sequence at least 95% identical to SEQ ID NO: 25, 1, 9, 17, 33, 41 or 49, or a light chain variable region having a polypeptide sequence at least 95% identical to SEQ ID NO: 29, 5, 13, 21, 37, 45 or 53. Preferably, the isolated monoclonal antibody or antigen-binding fragment thereof of the invention comprises a heavy chain variable region having a polypeptide sequence at least 95% identical to SEQ ID NO: 25, 1, 9, 17, 33, 41 or 49, and a light chain variable region having a polypeptide sequence at least 95% identical to SEQ ID NO: 29, 5, 13, 21, 37, 45 or 53, respectively.

According to another particular aspect, the invention relates to an isolated monoclonal antibody or antigen-binding fragment thereof of the invention, comprising:
a. a heavy chain variable region having the polypeptide sequence of SEQ ID NO: 25, and a light chain variable region having the polypeptide sequence of SEQ ID NO: 29;
b. a heavy chain variable region having the polypeptide sequence of SEQ ID NO: 1, and a light chain variable region having the polypeptide sequence of SEQ ID NO: 5;
c. a heavy chain variable region having the polypeptide sequence of SEQ ID NO: 9, and a light chain variable region having the polypeptide sequence of SEQ ID NO: 13;
d. a heavy chain variable region having the polypeptide sequence of SEQ ID NO: 17, and a light chain variable region having the polypeptide sequence of SEQ ID NO: 21;
e. a heavy chain variable region having the polypeptide sequence of SEQ ID NO: 33, and a light chain variable region having the polypeptide sequence of SEQ ID NO: 37;
f. a heavy chain variable region having the polypeptide sequence of SEQ ID NO: 41, and a light chain variable region having the polypeptide sequence of SEQ ID NO: 45; or
g. a heavy chain variable region having the polypeptide sequence of SEQ ID NO: 49, and a light chain variable region having the polypeptide sequence of SEQ ID NO: 53.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 6, 7, 8, 2, 3, and 4, respectively. In another embodiment, the isolated monoclonal antibody or antigen-binding fragment thereof comprises a heavy chain variable region having a polypeptide sequence at least 95% identical to SEQ ID NO: 1, and a light chain variable region having a polypeptide sequence at least 95% identical to SEQ ID NO: 5. Preferably, the isolated monoclonal antibody or antigen-binding fragment thereof comprises a heavy chain variable region having the polypeptide sequence of SEQ ID NO: 1; and a light chain variable region having the polypeptide sequence of SEQ ID NO: 5.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 14, 15, 16, 10, 11, and 12, respectively, respectively. In another embodiment, the isolated monoclonal antibody or antigen-binding fragment thereof comprises a heavy chain variable region having a polypeptide sequence at least 95% identical to SEQ ID NO: 9, and a light chain variable region having a polypeptide sequence at least 95% identical to SEQ ID NO: 13. Preferably, the isolated monoclonal antibody or antigen-binding fragment thereof comprises a heavy chain variable region having the polypeptide sequence of SEQ ID NO: 9; and a light chain variable region having the polypeptide sequence of SEQ ID NO: 13.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 22, 23, 24, 18, 19, and 20, respectively, respectively. In another embodiment, the isolated monoclonal antibody or antigen-binding fragment thereof comprises a heavy chain variable region having a polypeptide sequence at least 95% identical to SEQ ID NO: 17, and a light chain variable region having a polypeptide sequence at least 95% identical to SEQ ID NO: 21. Preferably, the isolated monoclonal antibody or antigen-binding fragment thereof comprises a heavy chain variable region having the polypeptide sequence of SEQ ID NO: 17; and a light chain variable region having the polypeptide sequence of SEQ ID NO: 21.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 30, 31, 32, 26, 27, and 28, respectively. In another embodiment, the isolated monoclonal antibody or antigen-binding fragment thereof comprises a heavy chain variable region having a polypeptide sequence at least 95% identical to SEQ ID NO: 25, and a light chain variable region having a polypeptide sequence at least 95% identical to SEQ ID NO: 29. Preferably, the isolated monoclonal antibody or antigen-binding fragment thereof comprises a heavy chain variable region having the polypeptide sequence of SEQ ID NO: 25; and a light chain variable region having the polypeptide sequence of SEQ ID NO: 29.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 38, 39, 40, 34, 35, and 36, respectively. In another embodiment, the isolated monoclonal antibody or antigen-binding fragment thereof comprises a heavy chain variable region having a polypeptide sequence at least 95% identical to SEQ ID NO: 33, and a light chain variable region having a polypeptide sequence at least 95% identical to SEQ ID NO: 37. Preferably, the isolated monoclonal antibody or antigen-binding fragment thereof comprises a heavy chain variable region having the polypeptide sequence of SEQ ID NO: 33; and a light chain variable region having the polypeptide sequence of SEQ ID NO:37.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 46, 47, 48, 42, 43, and 44, respectively. In another embodiment, the isolated monoclonal antibody or antigen-binding fragment thereof comprises a heavy chain variable region having a polypeptide sequence at least 95% identical to SEQ ID NO: 41, and a light chain variable region having a polypeptide sequence at least 95% identical to SEQ ID NO: 45. Preferably, the isolated monoclonal antibody or antigen-binding fragment thereof comprises a heavy chain variable region having the polypeptide sequence of SEQ ID NO: 41; and a light chain variable region having the polypeptide sequence of SEQ ID NO:45.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 54, 55, 56, 50, 51, and 52, respectively. In another embodiment, the isolated monoclonal antibody or antigen-binding fragment thereof comprises a heavy chain variable region having a polypeptide sequence at least 95% identical to SEQ ID NO: 49, and a light chain variable region having a polypeptide sequence at least 95% identical to SEQ ID NO: 53. Preferably, the isolated monoclonal antibody or antigen-binding fragment thereof comprises a heavy chain variable region having the polypeptide sequence of SEQ ID NO: 49; and a light chain variable region having the polypeptide sequence of SEQ ID NO:53.

According to another particular aspect, the invention relates to an isolated monoclonal antibody or antigen-binding fragment thereof of the invention, wherein the antibody or antigen-binding fragment thereof is chimeric.

According to another particular aspect, the invention relates to an isolated monoclonal antibody or antigen-binding fragment thereof of the invention, wherein the antibody or antigen-binding fragment thereof is human.

According to another particular aspect, the invention relates to an isolated monoclonal antibody or antigen-binding fragment thereof of the invention, comprising a constant region, preferably a human heavy chain IgG4 constant region, more preferably a human heavy chain IgG4 constant region having a S228P mutation (SEQ ID NO: 75), and a human antibody light chain, preferably a human light chain kappa constant region (SEQ ID NO: 77).

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody) or CHO-K1 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

In another general aspect, the invention relates to a pharmaceutical composition, comprising an isolated monoclonal antibody or antigen-binding fragment thereof of the invention and a pharmaceutically acceptable carrier.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

In another general aspect, the invention relates to a method of blocking the binding of PD-1 to PD-L1 or to PD-L2, or of augmenting secretion of IFN-γ and IL-2 in a subject in need thereof, comprising administering to the subject a pharmaceutical composition of the invention.

The functional activity of antibodies and antigen-binding fragments thereof that bind PD-1 can be characterized by methods known in the art and as described herein. Methods for characterizing antibodies and antigen-binding fragments thereof that bind PD-1 include, but are not limited to, affinity and specificity assays including Biacore, ELISA, and FACS analysis; receptor ligand binding assays to detect blocking of the binding of PD-1 to PD-L1 and PD-L2; assays to detect induction of lymphocytic cytokine production by the blocking of the binding of PD-1 to PD-L1 and PD-L2; cell cytotoxicity assays to detect the presence of antibody-dependent cell-mediated cytotoxicity (ADCC), and complement dependent cytotoxicity (CDC) activity of the antibodies; experiments to detect the inhibition of tumor growth in mouse tumor models; etc. According to particular embodiments, the methods for characterizing antibodies and antigen-binding fragments thereof that bind PD-1 include those described in Examples 2-12 below.

In another general aspect, the invention relates to a method of treating an infectious disease or a graft versus host disease in a subject in need thereof, comprising administering to the subject a pharmaceutical composition of the invention. In another general aspect, the invention relates to a method of treating a tumor in a subject in need thereof, comprising administering to the subject a pharmaceutical composition of the invention.

As used herein, the term "subject" refers to an animal, and preferably a mammal. According to particular embodiments, the subject is a mammal including a non-primate (e.g., a camel, donkey, zebra, cow, pig, horse, goat, sheep, cat, dog, rat, rabbit, guinea pig or mouse) or a primate (e.g., a monkey, chimpanzee, or human). In particular embodiments, the subject is a human.

According to embodiments of the invention, the pharmaceutical composition comprises a therapeutically effective amount of the anti-PD-1 antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-PD-1 antibodies or antigen-binding fragments thereof, a therapeutically effective amount means an amount of the anti-PD-1 antibody or antigen-binding fragment thereof that stimulates an immune response in a subject in need thereof. Also as used herein with reference to anti-PD-1 antibodies or antigen-binding fragments thereof, a therapeutically effective amount means an amount of the anti-PD-1 antibody or antigen-binding fragment thereof that results in treatment of a disease, disorder, or condition; prevents or slows the progression of the disease, disorder, or condition; or reduces or completely alleviates symptoms associated with the immune disease, disorder, or condition.

According to particular embodiments, the disease, disorder or condition to be treated is a hyperproliferative disease, an infectious disease, an inflammatory disease, an immune disease, an autoimmune disease, or a graft versus host disease. According to more particular embodiments, the disease, disorder or condition to be treated is an infectious disease, an inflammatory disease, an immune disease, an autoimmune disease, or a graft versus host disease. According to more particular embodiments, the disease, disorder or condition to be treated is a non-malignant hyperproliferative disease, including but not limited to, atherosclerosis, benign hyperplasia, benign prostatic hypertrophy. According to other particular embodiments, the disease, disorder or condition to be treated is a tumor, or a malignant hyperproliferative disease, preferably a tumor selected from the group consisting of a solid tumor, a hematologic cancer, bladder cancer, biliary cancer, brain cancer, breast cancer, colon cancer, esophageal cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder od condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, an inflammatory disease, disorder or condition, an immune disease, disorder or condition, an autoimmune disease, disorder or condition, or an infectious disease, disorder or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, a composition used in the treatment of a cancer, an inflammatory disease, disorder or condition, an immune disease, disorder or condition, an autoimmune disease, disorder or condition, or an infectious disease, disorder or condition can be used in combination with another treatment including, but not limited to, a chemotherapy, an anti-CD20 mAb, an anti-CTLA-4 antibody, an antiangiogenic agent, a radiation therapy, other immune-oncology drug, a targeted therapy, anti-PD-L1 antibody or other anticancer drugs.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

EMBODIMENTS

The invention provides also the following non-limiting embodiments.

Embodiment 1 is an isolated monoclonal antibody or antigen-binding fragment thereof comprising LCDR1, LCDR2, LCDR3, HCDR1, HCDR2 and HCDR3, having the polypeptide sequences of:
 (1) SEQ ID NOs: 30, 31, 32, 26, 27, and 28, respectively;
 (2) SEQ ID NOs: 6, 7, 8, 2, 3, and 4, respectively;
 (3) SEQ ID NOs: 14, 15, 16, 10, 11, and 12, respectively;
 (4) SEQ ID NOs: 22, 23, 24, 18, 19, and 20, respectively;
 (5) SEQ ID NOs: 38, 39, 40, 34, 35, and 36, respectively;
 (6) SEQ ID NOs: 46, 47, 48, 42, 43, and 44, respectively; or
 (7) SEQ ID NOs: 54, 55, 56, 50, 51, and 52, respectively;
 wherein the antibody or antigen-binding fragment thereof binds PD-1.

Embodiment 2 is the isolated monoclonal antibody or antigen-binding fragment of Embodiment 1, comprising a heavy chain variable region having a polypeptide sequence at least 95% identical to SEQ ID NO: 25, 1, 9, 17, 33, 41 or 49, or a light chain variable region having a polypeptide sequence at least 95% identical to SEQ ID NO: 29, 5, 13, 21, 37, 45 or 53.

Embodiment 3 is the isolated monoclonal antibody or antigen-binding fragment of Embodiment 2, comprising a heavy chain variable region having a polypeptide sequence at least 95% identical to SEQ ID NO: 25, 1, 9, 17, 33, 41 or 49, and a light chain variable region having a polypeptide sequence at least 95% identical to SEQ ID NO: 29, 5, 13, 21, 37, 45 or 53, respectively.

Embodiment 4 is the isolated monoclonal antibody or antigen-binding fragment of Embodiment 3, comprising:
 (a) a heavy chain variable region having the polypeptide sequence of SEQ ID NO: 25, and a light chain variable region having the polypeptide sequence of SEQ ID NO: 29;
 (b) a heavy chain variable region having the polypeptide sequence of SEQ ID NO: 1, and a light chain variable region having the polypeptide sequence of SEQ ID NO: 5;
 (c) a heavy chain variable region having the polypeptide sequence of SEQ ID NO: 9, and a light chain variable region having the polypeptide sequence of SEQ ID NO: 13;
 (d) a heavy chain variable region having the polypeptide sequence of SEQ ID NO: 17, and a light chain variable region having the polypeptide sequence of SEQ ID NO: 21;
 (e) a heavy chain variable region having the polypeptide sequence of SEQ ID NO: 33, and a light chain variable region having the polypeptide sequence of SEQ ID NO: 37;

(f) a heavy chain variable region having the polypeptide sequence of SEQ ID NO: 41, and a light chain variable region having the polypeptide sequence of SEQ ID NO: 45; or (g) a heavy chain variable region having the polypeptide sequence of SEQ ID NO: 49, and a light chain variable region having the polypeptide sequence of SEQ ID NO: 53.

Embodiment 5 is the isolated monoclonal antibody or antigen-binding fragment of any of Embodiments 1 to 4, wherein the antibody or antigen-binding fragment thereof is chimeric.

Embodiment 6 is isolated monoclonal antibody or antigen-binding fragment of any of Embodiments 1 to 5, wherein the antibody or antigen-binding fragment thereof is human.

Embodiment 7 is the isolated antibody or antigen-binding fragment of Embodiment 6, comprising a human heavy chain IgG4 constant region with a S228P mutation, and a human antibody light chain kappa constant region.

Embodiment 8 is the isolated antibody or antigen-binding fragment of any of Embodiments 1 to 7, wherein the antibody or antigen-binding fragment binds to a human PD-1 with a $K_D$ of $5\times10^{-9}$M or less, preferably a $K_D$ of $1\times10^{-9}$M or less, wherein the $K_D$ is measured by surface plasmon resonance analysis, such as by using a Biacore system, or by a bio-layer interferometry technology, such as by using a Octet RED96 system.

Embodiment 9 is an isolated nucleic acid encoding the monoclonal antibody or antigen-binding fragment of any of Embodiments 1 to 8.

Embodiment 10 is a vector comprising the isolated nucleic acid of Embodiment 9.

Embodiment 11 is a host cell comprising the nucleic acid of Embodiment 10.

Embodiment 12 is a pharmaceutical composition, comprising the isolated monoclonal antibody or antigen-binding fragment of any of Embodiments 1 to B and a pharmaceutically acceptable carrier.

Embodiment 13 is a method of blocking binding of PD-1 to PD-L1 or PD-L2, or augmenting secretion of IFN-γ and IL-2 in a subject in need thereof, comprising administering to the subject the pharmaceutical composition of Embodiment 12.

Embodiment 14 is a method of treating an infectious disease, an inflammatory disease, an immune disease, an autoimmune disease, or a graft versus host disease in a subject in need thereof, comprising administering to the subject the pharmaceutical composition of Embodiment 12.

Embodiment 15 is the method of Embodiment 14, further comprising administering to the subject an additional agent for treating the infectious disease, inflammatory disease, immune disease, autoimmune disease, or graft versus host disease in the subject in need thereof.

Embodiment 16 is a method of treating a hyperproliferative disease in a subject in need thereof, comprising administering to the subject the pharmaceutical composition of Embodiment 12, Embodiment 17 is the method of Embodiment 16, wherein the hyperproliferative disease is a non-malignant disease, preferably selected from the group consisting of atherosclerosis, benign hyperplasia and benign prostatic hypertrophy.

Embodiment 18 is the method of Embodiment 16, wherein the hyperproliferative disease is a tumor, or a malignant disease, preferably, the tumor is selected from the group consisting of a solid tumor, a hematologic cancer, bladder cancer, biliary cancer, brain cancer, breast cancer, colon cancer, esophageal cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer.

Embodiment 19 is the method of any of Embodiments 16-18, further comprising administering to the subject an additional agent for treating the hyperproliferative disease in the subject in need thereof.

Embodiment 20 is a method of producing the monoclonal antibody or antigen-binding fragment of any of Embodiments 1 to 8, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or cell culture.

Embodiment 21 is a method of producing a pharmaceutical composition comprising the monoclonal antibody or antigen-binding fragment of any of Embodiments 1 to 8, comprising combining the monoclonal antibody or antigen-binding fragment with a pharmaceutically acceptable carrier to obtain the pharmaceutical composition.

Embodiment 22 is an isolated monoclonal antibody or antigen-binding fragment of any of Embodiments 1 to 8 for use in treating an infectious disease, an inflammatory disease, an immune disease, an autoimmune disease, or a graft versus host disease in a subject in need thereof.

Embodiment 23 is an isolated monoclonal antibody or antigen-binding fragment of any of Embodiments 1 to 8 for use in treating a hyperproliferative disease, such as a non-malignant disease selected from the group consisting of atherosclerosis, benign hyperplasia and benign prostatic hypertrophy, or a tumor selected from the group consisting of a solid tumor, a hematologic cancer, bladder cancer, biliary cancer, brain cancer, breast cancer, colon cancer, esophageal cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer.

Embodiment 24 is an use of an isolated monoclonal antibody or antigen-binding fragment of any of Embodiments 1 to 8 for manufacturing a pharmaceutical composition in treating an infectious disease, an inflammatory disease, an immune disease, an autoimmune disease, or a graft versus host disease in a subject in need thereof.

Embodiment 25 is an use of an isolated monoclonal antibody or antigen-binding fragment of any of Embodiments 1 to 8 for manufacturing a pharmaceutical composition in treating a hyperproliferative disease, such as a non-malignant disease selected from the group consisting of atherosclerosis, benign hyperplasia and benign prostatic hypertrophy, or a tumor selected from the group consisting of a solid tumor, a hematologic cancer, bladder cancer, biliary cancer, brain cancer, breast cancer, colon cancer, esophageal cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer.

EXAMPLES

The following examples of the invention are to further illustrate the nature of the invention. It should be understood that the following examples do not limit the invention and that the scope of the invention is to be determined by the appended claims.

Example 1—Generation of Anti-PD-1 Antibodies

Human PD-1 protein was used as an immunogen to generate anti-PD-1 antibodies. The uses of human immunoglobulin transgenic mouse technology for the development and preparation of fully human antibodies was first described by Abgenix (xeno mouse and Medarex (HuMab "mouse"); Lonberg et al., 1994, Nature 368: 856-859; Lonberg and Huszar, 1995, Internal Rev. Immunol. 13:65-93; Harding and Lonberg, 1995, Ann. N.Y. Acad. Sci. 764:536-546).

Antibodies with high affinity ($K_D < 1*10^{-9}$M) to PD-1 were obtained by carrying out pilot antibody production, purification and validation. The antibodies, which are specific for PD-1 and do not cross react with other immune checkpoints such as B7.1, CD28, CTLA-4, and ICOS, are able to block the binding of PD-1 to PD-L1 and PD-L2. The amino acid sequences of the heavy and light chain variable regions of the generated anti-PD-1 antibodies were determined using standard molecular biology methods and are summarized in Table 1.

TABLE 1

SEQ ID NOs of the amino acid sequences of the heavy chain variable regions, HCDRs, light chain variable regions and LCDRs of chimeric anti-PD-1 antibodies of the invention

| | SEQ ID Nos | | | | | | | |
|---|---|---|---|---|---|---|---|---|
| | Heavy Chain | | | | Light Chain | | | |
| Clone ID | variable region | CDR1 | CDR2 | CDR3 | variable region | CDR1 | CDR2 | CDR3 |
| 9B2C6C9 | 1 | 2 | 3 | 4 | 5 | 6 | 7 | 8 |
| 76G5B3 | 9 | 10 | 11 | 12 | 13 | 14 | 15 | 16 |
| 32B5C7 | 17 | 18 | 19 | 20 | 21 | 22 | 23 | 24 |
| 223G6B5 | 25 | 26 | 27 | 28 | 29 | 30 | 31 | 32 |
| 21G8F11 | 33 | 34 | 35 | 36 | 37 | 38 | 39 | 40 |
| 226C3A7 | 41 | 42 | 43 | 44 | 45 | 46 | 47 | 48 |
| 204C5E12 | 49 | 50 | 51 | 52 | 53 | 54 | 55 | 56 |

The heavy chain and light chain variable regions of the anti-PD-1 antibodies listed in Table 1 are encoded by the nucleic acid sequences summarized in Table 2.

TABLE 2

SEQ ID NOs of the nucleic acid sequences of the heavy chain and light chain variable regions of chimeric anti-PD-1 antibodies of the invention

| | SEQ ID NOs (nucleotides of the sequence corresponding to CDRs) | |
|---|---|---|
| Clone ID | Heavy Chain | Light Chain variable region |
| 9B2C6C9 | 57 (CDR1: nt 76-108) (CDR2: nt 151-198) (CDR3: nt 295-336) | 58 (CDR1: nt 70-117) (CDR2: nt 163-183) (CDR3: nt 280-306) |
| 76G5B3 | 59 (CDR1: nt 76-105) (CDR2: nt 148-198) (CDR3: nt 295-309) | 60 (CDR1: nt 70-102) (CDR2: nt 148-168) (CDR3: nt 265-291) |
| 32B5C7 | 61 (CDR1: nt 76-105) (CDR2: nt 148-198) (CDR3: nt 295-312) | 62 (CDR1: nt 70-102) (CDR2: nt 148-168) (CDR3: nt 265-291) |
| 223G6B5 | 63 (CDR1: nt 76-108) (CDR2: nt 151-198) (CDR3: nt 295-324) | 64 (CDR1: nt 70-102) (CDR2: nt 148-168) (CDR3: nt 265-291) |
| 21G8F11 | 65 (CDR1: nt 76-105) (CDR2: nt 148-198) (CDR3: nt 295-327) | 66 (CDR1: nt 70-102) (CDR2: nt 148-168) (CDR3: nt 265-291) |
| 226C3A7 | 67 (CDR1: nt 76-111) (CDR2: nt 154-207) (CDR3: nt 304-342) | 68 (CDR1: nt 70-102) (CDR2: nt 148-168) (CDR3: nt 265-291) |
| 204C5E12 | 69 (CDR1: nt 76-105) (CDR2: nt 148-198) (CDR3: nt 295-348) | 70 (CDR1: nt 70-117) (CDR2: nt 163-183) (CDR3: nt 280-306) |

Fully human versions of the anti-PD-1 antibodies were generated. The fully human anti-PD-1 antibodies bound to the extracellular domain of human PD-1 with high affinity ($K_D < 1*10^{-9}$M), and blocked the binding of PD-1 to its ligands, PD-L1 and PD-L2. The anti-PD-1 antibodies do not exhibit non-specific binding to human B7.1, CD28, CTLA-4, ICOS or other similar protein antigens. The biological activities of the anti-PD-1 antibodies were evaluated by mixed lymphocyte and T cell stimulation assays, in which they increased secretion of the IFN-γ and IL-2 cytokines. While not wishing to be bound by theories, it is believed that the anti-PD-1 antibodies can be used to suppress PD-1-mediated signaling pathways that negatively-regulate immune responses, and to therefore enhance tumor-specific immune responses, either as a monotherapy or in combination with anti-PD-L1 monoclonal antibodies or other anti-cancer drugs as a cancer immunotherapy, particularly for patients having PD-L1 positive tumors. The anti-PD-1 antibodies can be used for the treatment of cancers and autoimmune diseases.

Example 2—Preparation of Anti-PD-1 Antibodies (Step 1) Preparation of Immunogen A, PD-1$^{ECD}$-hFc Protein (Also Referred to as PD-1-hFc Herein)

The coding sequence of the human PD-1 extracellular domain (PD-1$^{ECD}$; SEQ ID NO: 71), corresponding to amino acids Leu25-Glu167 of SEQ ID No.72, was cloned along with the coding sequence of human IgG Fc fragment (hFc) into a pCpC vector (Invitrogen, #V044-50) using standard molecular biology cloning techniques (Sambrook and Russell, 1989, Molecular cloning: a laboratory manual, New York: Cold Spring Harbor Laboratory Press, 2nd ed.). HEK293 cells (Invitrogen) were transiently transfected using polyethylenimine (PEI, Polysciences) with the plasmid and expanded in FreeStyle 293 expression medium (Invitrogen) at 37° C. After 4 days of expansion, the culture medium was collected and centrifuged to remove cell components. The culture supernatant, which contained the recombinant PD-1$^{ECD}$-hFc, was subjected to Protein A chromatography (Mabselect, GE Healthcare). The ultraviolet (UV) absorption (A280 nm) was monitored with a UV detector, and the samples were washed with PBS (pH 7.2) until the UV A280 nm absorption returned to baseline levels, at which point the PD-1$^{ECD}$-hFc fusion protein was eluted from the Protein A affinity column with 0.1M glycine hydrochloride (pH2.5). The sample was dialyzed with PBS phosphate buffer (pH 7.2) at 4° C. overnight. After dialysis, the purified PD-1 immunogen was passed through a 0.22 micron sterile filter, aliquoted and stored at −80° C.

Recombinant human PD-L1 extracellular domain (PD-L1$^{ECD}$) (corresponding to amino acids Phe19-Thr239 of Uniprot database protein Q9NZQ7.1) fused to hFc was prepared in the same way that the PD-1$^{ECD}$-hFc recombinant protein was prepared above. Purified PD-L1$^{ECD}$-hFc (also referred to as PD-L1-hFc herein) was biotinylated by mixing and incubating the protein with biotin (Sigma S3295).

To characterize the PD-1$^{ECD}$-hFc immunogen, the sample's protein concentration and purity were determined, and the immunogen's molecular weight and biological activity were determined.

The biological activity of the PD-1$^{ECD}$-hFc immunogen was determined by a ligand binding assay. Recombinant PD-1$^{ECD}$-hFc protein was diluted in PBS to a concentration of 1 μg/mL, and 100 μL of the diluted PD-1$^{ECD}$-hFc protein sample were added per well to microtiter plates, which were incubated overnight at 4° C. to coat the plates with the recombinant protein. The plates were then blocked with a blocking solution (containing 1% BSA, pH7.4 PBS buffer, w/v) at 37° C. for two hours and then incubated with serial dilutions of the biotinylated PD-L1$^{ECD}$-hFc protein or a control protein (biotinylatednon-PD-L1$^{ECD}$-hFc) for 1 hour at 37° C. Horseradish peroxidase (HRP) conjugated streptavidin (Sigma B2438) was added, and the plates were incubated at room temperature for 30 minutes. 100 uL of tetramethylbenzidine (TMB) were added, and the plates were incubated at room temperature for 15 minutes. 50 uL of IN HCl were added to terminate the reaction, and the OD450 nm was determined by amicrotiter plate reader. FIG. 1 and Table 3 show the concentration-dependent binding of the biotinylated PD-L1$^{ECD}$-hFc protein or control protein to purified PD-1$^{ECD}$-hFc fusion protein. Binding to PD-1$^{ECD}$-hFc was observed with biotinylated PD-L1$^{ECD}$-hFc, but not with the control protein that does not contain the sequence of PD-L1$^{ECD}$.

TABLE 3

Binding activities of PD-1$^{ECD}$-hFc to biotinylated PD-L1$^{ECD}$-hFc

| Biotinylated Sample | OD$_{450\ nm}$ PD-L1$^{ECD}$-hFc/Control Protein Concentration (μg/mL) | | | | | | | |
|---|---|---|---|---|---|---|---|---|
| | 1 | 0.2 | 0.04 | 0.008 | 0.0016 | 0.0003 | 0.0001 | 0.00001 |
| PD-L1$^{ECD}$-hFc Batch1 | 3.23 | 3.205 | 2.97 | 0.705 | 0.205 | 0.11 | 0.145 | 0.09 |
| PD-L1$^{ECD}$-hFc Batch2 | 3.26 | 3.24 | 2.73 | 0.705 | 0.285 | 0.205 | 0.1 | 0.185 |
| Control protein | 0.13 | 0.095 | 0.09 | 0.14 | 0.195 | 0.195 | 0.32 | 0.205 |

(Step 2) Preparation of Immunogen B, HEK293 Cells Over Expressing hPD-1

The nucleotide sequence encoding human PD-1 (SEQ ID NO: 73) was subcloned into a pIRES vector (Clontech), and the plasmid was prepared. HEK293 and CHO-K1 cells (Invitrogen) were transiently transfected with the plasmid using PEI, and transformants were selected in DMEM culture media containing 0.5 g/mL antibiotics and 10% (w/w) fetal bovine serum (FBS) for 2 weeks. A limited dilution into a 96-well culture plate was carried out, and the plate was incubated at 37° C. with 5% (v/v) CO$_2$ for approximately 2 weeks. After selection, monoclones were expanded in 6-well plates, and the expanded clones were screened by flow cytometry using commercially available anti-PD-1 antibodies (R&D Systems). Clones exhibiting higher growth rates and higher fluorescence intensity as measured by FACS were further expanded and cryopreserved in liquid nitrogen.

Figure 2:
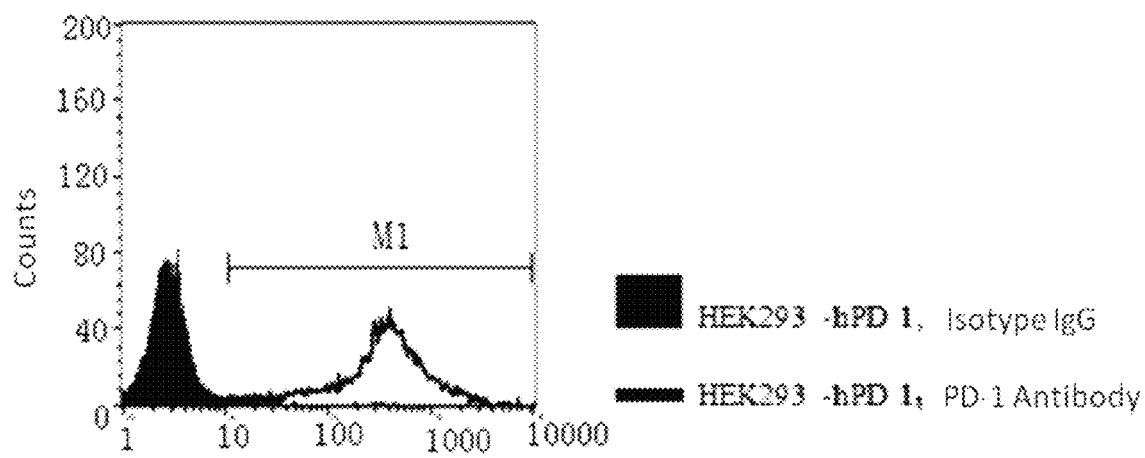
FIG. 2 shows the flow cytometry profile of HEK293 cells stably transfected with PD-1 protein.

FIG. 2 shows the flow cytometry profile of the HEK293 cells stably transfected with the recombinant hPD-1 protein. The percentage of FACS-positive cells are shown in Table 4 as an indication of the expression levels of hPD-1 protein.

TABLE 4 hPD-1 expression levels of recombinant HEK293 clones, as determined by FACS

| No. | Recombinant cell clone ID | PD mAb Gated (%) | MFI | IgG Control Gated (%) | MFI |
|---|---|---|---|---|---|
| 1 | 293F-hPD1 1A2 | 43.38 | 17.8 | 0.83 | 3.11 |
| 2 | 293F-hPD1 1A6 | 96.23 | 275.9 | 0.45 | 2.9 |
| 3 | 293F-hPD1 1B4 | 95.9 | 266.52 | 0.54 | 3.13 |
| 4 | 293F-hPD1 1C1 | 95.5 | 261.6 | 0.92 | 3.09 |
| 5 | 293F-hPD1 1C10 | 96.43 | 297.88 | 0.44 | 3.13 |
| 6 | 293F-hPD1 1C6 | 97.47 | 196.04 | 2.8 | 3.7 |
| 7 | 293F-hPD1 1D2 | 96.95 | 226.39 | 0.57 | 3.08 |
| 8 | 293F-hPD1 1D4 | 96.71 | 202.08 | 1.45 | 3.31 |
| 9 | 293F-hPD1 1D6 | 94.41 | 255.87 | 0.74 | 3.11 |
| 10 | 293F-hPD1 1D7 | 95.13 | 246.53 | 0.81 | 3.03 |
| 11 | 293F-hPD1 1E1 | 95.77 | 174.74 | 0.53 | 3.17 |
| 12 | 293F-hPD1 1E2 | 95.67 | 222.33 | 1.74 | 3.66 |
| 13 | 293F-hPD1 1F1 | 96.68 | 303.23 | 0.72 | 3.37 |

TABLE 4-continued hPD-1 expression levels of recombinant HEK293 clones, as determined by FACS

| No. | Recombinant cell clone ID | PD mAb Gated (%) | MFI | IgG Control Gated (%) | MFI |
|---|---|---|---|---|---|
| 14 | 293F-hPD1 1F4 | 97.05 | 248.22 | 1.38 | 2.93 |
| 15 | 293F-hPD1 1F5 | 96.01 | 148.82 | 0.64 | 2.86 |
| 16 | 293F-hPD1 1F8 | 96.16 | 234.31 | 0.7 | 3.21 |
| 17 | 293F-hPD1 1G1 | 96.45 | 312.87 | 0.71 | 3.08 |
| 18 | 293F-hPD1 1G10 | 98.67 | 341.57 | 0.44 | 2.9 |
| 19 | 293F-hPD1 1G11 | 95.53 | 300.49 | 0.59 | 3.4 |
| 20 | 293F-hPD1 1G12 | 95.47 | 339.92 | 0.43 | 3.13 |
| 21 | 293F-hPD1 1G4 | 97.87 | 366.88 | 0.71 | 3.27 |

TABLE 4-continued hPD-1 expression levels of recombinant HEK293 clones, as determined by FACS

| No. | Recombinant cell clone ID | PD mAb Gated (%) | MFI | IgG Control Gated (%) | MFI |
|---|---|---|---|---|---|
| 22 | 293F-hPD1 1G6 | 97.38 | 293.46 | 0.67 | 2.94 |
| 23 | 293F-hPD1 1H5 | 96.99 | 223.54 | 1.14 | 3.46 |

(Step 3) Preparation of Immunogen C, hPD-1 Expressing Construct

The coding sequence of full length human PD-1 protein (SEQ ID No.73) was subcloned into a pcDNA3.1 vector (Invitrogen), and the resulting plasmid was coated onto a 1.0 um colloidal gold bullet (Bio-RAD) for subsequent immunization using a Helios gene gun (Bio-rad No. 165-2431), following the instructions of the Helios gene gun data sheet.

(Step 4) Hybridoma Cell Fusion and Antibody Screening

Human Ig Fc does not interact with the mouse Fc receptor, so immune responses triggered in mice by hFc-containing immunogens are weak, resulting in low efficiency generation of monoclonal antibodies. Harbour H2L2 transgenic mice were generated by introducing the gene encoding the human immunoglobulin (Ig) variable region and the gene encoding the rat Ig constant region into the mouse genome, such that the mice contained a chimeric Ig comprising hV-rC, while expression of the mouse Ig was disabled (WO 2010/070263 A1). Harbour H2L2 transgenic mice are able to produce comparable immune responses and antibody titers to wild type mice (e.g., Balb/c).

Figure 3:
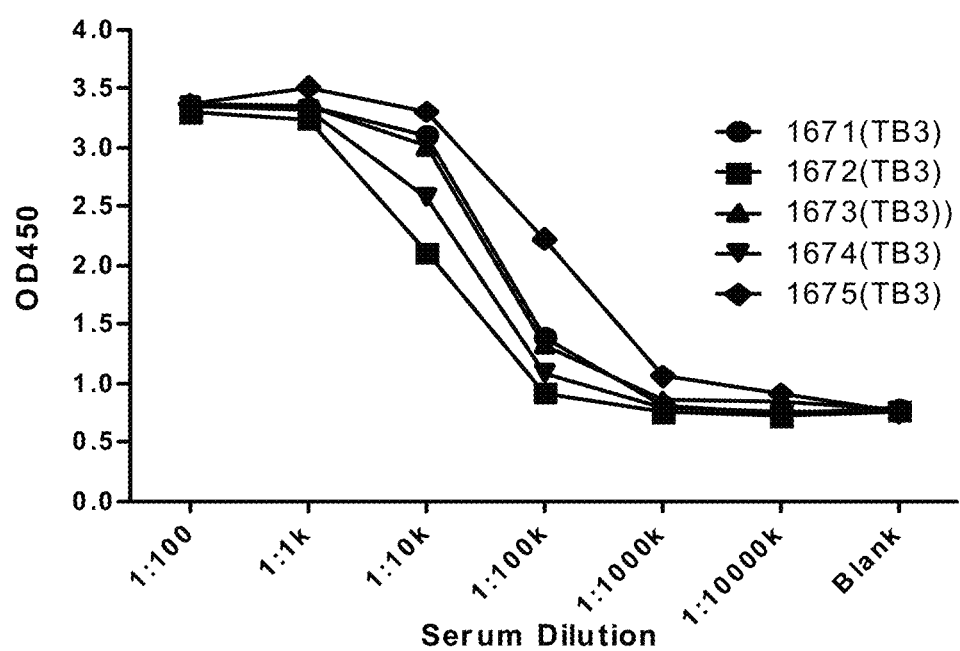
FIG. 3 shows the ELISA measurement of serum antibody titers of transgenic mice after immunization with PD-1 protein, where 1671-1675 represent the mouse ID numbers.

(part 4A) 6-8 week old Harbour H2L2 transgenic mice (Beijing WeitongLihua) were immunized with Immunogen A, and the mice were kept under Specific Pathogen Free (SPF) conditions. In the first immunization, 50 ug of Immunogen A was injected into the abdominal cavity of each mouse along with 0.25 mL Complete Freund's Adjuvant (CFA). To enhance the immune response, 50 ug of Immunogen A was injected into the abdominal cavity of each mouse along with 0.25 Incomplete Freund's Adjuvant (IFA) two weeks after the first immunization, and subsequent boosts were administered 3 weeks apart. Blood samples were collected one week after immunization. The antibody titer and specificity in serum were determined by ELISA and FACS analysis, and the results are shown in FIG. 3 and Table 5. Table 5 shows that serum from mice immunized with PD-1$^{ECD}$-hFc exhibited different levels of binding to Immunogen A. The highest serum dilution was about one million. The blank control was 1% (w/w) BSA. The OD450 nm values shown in Table 5 are the serum titer values from 7 days after the third boost, as determined by ELISA.

TABLE 5

Serum titers of Harbour H2L2 transgenic mice immunized with hPD-1$^{ECD}$-hFc fusion protein, as determined by ELISA

| Animal No. | OD$_{450\,nm}$ Serum dilution factors | | | | | | |
|---|---|---|---|---|---|---|---|
| | 1:100 | 1:10$^3$ | 1:10$^4$ | 1:10$^5$ | 1:10$^6$ | 1:10$^7$ | Blank |
| 1671 (TB3) | 3.3651 | 3.3434 | 3.1001 | 1.3935 | 0.8103 | 0.7423 | 0.7921 |
| 1672 (TB3) | 3.2939 | 3.2384 | 2.1086 | 0.9142 | 0.7536 | 0.7248 | 0.7682 |
| 1673 (TB3) | 3.3487 | 3.3544 | 3.0128 | 1.3243 | 0.859 | 0.8475 | 0.7715 |
| 1674 (TB3) | 3.3584 | 3.325 | 2.5794 | 1.0904 | 0.788 | 0.7563 | 0.7558 |
| 1675 (TB3) | 3.3611 | 3.513 | 3.3012 | 2.2199 | 1.0601 | 0.9124 | 0.7528 |

(part4B) 6-8 week old Harbour H2L2 transgenic mice (Beijing WeitongLihua) were immunized with Immunogen B, and the mice were kept under SPF conditions. HEK293 cells were stably transfected with the pIRES plasmid encoding full length hPD-1 (see Example 2, step 2)) using X-treme gene HP DNA Transfection reagent (Roche, #06 366 236 001). Cells were cultured in T-75 culture flasks. When the cells reached 90% confluence, the media was aspirated, and the cells were washed twice with DMEM medium (Invitrogen) and treated with non-enzymatic cell dissociation buffer (Invitrogen) at 37° C. until the cells were detached from the culture flask. The cells were collected and washed twice with DMEM medium, and cell counts were determined and adjusted to 2×10$^7$ cells/mL using PBS buffer (pH7.2). Mice were injected with 0.5 mL of cell suspension for each immunization. Two weeks after the first immunization, a boost was administered, and subsequent boosts were administered 3 weeks apart. Blood samples were collected one week after immunization. The antibody titer and specificity in serum were determined by flow cytometry. After the second boost, the serum titer was over 1:1000, as determined by flow cytometry, and over 1:10,000, as determined by ELISA.

(part4C) 6-8 week old Harbour H2L2 transgenic mice (Beijing WeitongLihua) were immunized with Immunogen C, and the mice were kept under SPF conditions. All mice were immunized with the Helios gene gun 4 times, with 4 shots per immunization. Each shot contained 1 ug cDNA. Two weeks after the first immunization, a boost was administered, and subsequent boosts were administered 3 weeks apart. Blood samples were collected one week after immunization, and the serum titer was determined by ELISA and FACS. The serum titer after the second boost was 1:1000, as determined by flow cytometry, and over 1:10,000, as determined by ELISA.

Prior to the completion of steps 4A-C above, mice with specific immune response against hPD-1 were selected for fusion and were given a final boost by intraperitoneal injection of 100 ug of purified PD-1$^{ECD}$-hFc (for mice immunized with Immunogen A or Immunogen C) or HKE293 cells stably transfected with hPD-1 (for mice immunized with Immunogen B). Five days later, the mice were sacrificed, and their splenocytes were collected. NH$_4$OH was added to the splenocyte samples to a final concentration of 1% (w/w) to lyse red blood cells in the sample. The samples were centrifuged at 1000 rpm and washed three times with DMEM culture media. The viability of the splenocytes was determined, and viable splenocytes were then fused with mouse myeloma cells SP2/0 (ATCC) at a ratio of 5:1 by the high efficiency electric fusion method (see Methods in Enzymology, Vol. 220).

Fused cells were re-suspended in DMEM media containing 20% FBS and 1× hypoxanthine-aminopterin-thymidine (HAT) medium (w/w), and the concentration was adjusted to 10$^5$ cells/200 uL. 200 uL of fused cells were added to each well of 96-well plate, which was incubated at 37° C., 5% CO$_2$. 14 days after cell fusion, hybridoma supernatants were collected and screened by ELISA and Acumen (microplate cell assay). Clones with an OD450 nm greater than 1.0 by ELISA and an MFI value greater than 100 by Acumen were expanded in a 24-well plate containing DMEM with 10% (w/w) heat-inactivated FBS at 37° C., 5% (v/v) CO$_2$. Supernatants were collected after 3 days of culturing. The antibody isotypes were determined, and their ability to bind to recombinant PD-1$^{ECD}$ protein and PD-1-expressing cells was determined by ELISA and flow cytometry (see Example 3). A receptor ligand binding assay was performed to determine the blocking activity of the hybridoma supernatant (see Examples 4-5).

Based on the 24-well plate screening results, clones with OD450 nm values greater than 1.0 by the ELISA binding assay, MFI values greater than 50 by the FACS binding assay, and inhibition rates greater than 60% by the receptor ligand binding assay were selected and subcloned. Subcloning was carried out by limited dilution in a 96-well plate with DMEM media containing 10% (v/v) FBS at 37° C. and 5% (v/v) CO$_2$. After 10 days of culturing, the supernatants were collected and preliminarily screened by ELISA and Acumen. Positive clones were expanded in a 24-well plate and cultured for 3 days. Supernatants were collected. ELISA and FACS binding assays were performed to determine the binding activity, and receptor ligand binding assays were performed to assess the biological activity. The selection criteria was as follows: OD450 nm>1.0 by ELISA, MFI value >50 by FACS, and inhibition rate >60% by receptor ligand binding assay. Clones that met the selection criteria were expanded in DMEM media containing 10% (w/w) FBS at 37° C., 5% (v/v) CO$_2$ and frozen in liquid nitrogen so that the hybridoma cells could be used for subsequent antibody production and purification.

(Step 5) Production and Purification of Lead Candidate Antibodies

The antibody concentrations from the hybridoma cells were low, about 1-10 ug/mL, and there was a large variation in antibody concentrations. In addition, the FBS and the components of the culture medium can interfere with the analysis. Therefore, it was necessary to perform small scale antibody production and purification (1-5 mg).

Hybridoma cells from Example 2 (part 4) were cultured in T-75 culture flasks using Hybridoma serum free medium (Invitrogen), and passaged for 3 generations. Cells were transferred to 2 L culture flasks when the hybridoma cells were in good condition. 500 mL of production media was added to each culture flask, and the cell density was adjusted to 10$^5$ cells/mL. The culture flasks were placed onto a rotary incubator at 37° C. with a rotating speed of 3 cycles per minute. Hybridoma cells were cultured for 14 days, after which the supernatant was collected and the cells were removed. The supernatants were then filtered through 0.45 micron filtration. The culture supernatants were then ready for purification or storage at −30° C.

Monoclonal antibodies were purified by passing the hybridoma culture supernatants through 2 mL Protein G columns (GE Healthcare). Protein G columns were first equilibrated with PBS buffer (pH7.2), and the hybridoma culture supernatants were then applied to the equilibrated Protein G columns with a constant flow rate of 3 mL/minute. The columns were then washed with 4 volumes of PBS buffer. The anti-PD-1 antibodies were then eluted with elution buffer (0.1M acetate buffer, pH2.5), and the UV absorbance of the eluates were monitored using a UV detector (A280 UV absorption peak). 10% of 1.0M Tris-HCL buffer was added to the eluates to neutralize the pH, and the samples were sterile-filtered by passing them through 0.22 micron filters. Sterile-filtered purified anti-PD-1 antibodies were obtained.

The concentrations of purified anti-PD-1 antibodies was determined by UV absorbance (A280/1.4), and the purity and endotoxin level (Lonza kit) were measured. The results of the analyses are shown in Table 6. The purified anti-PD-1 antibodies had endotoxin concentrations less than 1.0 EU/mg.

TABLE 6

Quality Control analysis of Purified Chimeric PD-1 mAbs from Hybridoma

| Clone ID | Purity | Protein Concentration (µg/mL) | Endotoxin (EU/µg) |
| --- | --- | --- | --- |
| 9B2C6C9 | >90% | 0.44 | 4.76 |
| 76G5B3 | >90% | 0.52 | 0.56 |
| 32B5C7 | >90% | 1.65 | 0.99 |
| 223G6B5 | >90% | 11.9 | 0.097 |
| 21G8F11 | ND | 3.5 | ND |

Example 3—Characterization of Lead Candidate Antibodies (Part A) Detection of the Binding of Anti-PD-1 Antibodies to Recombinant PD-1$^{ECD}$-hFc Protein by ELISA The binding of purified anti-PD-1 antibodies from Example 2 to recombinant human PD-1$^{ECD}$-hFc protein, cyno PD-1$^{ECD}$-hFc protein and other PD-1 family-related immune checkpoint proteins was analyzed by ELISA to determine the specificity of the antibodies.

Figure 4A:
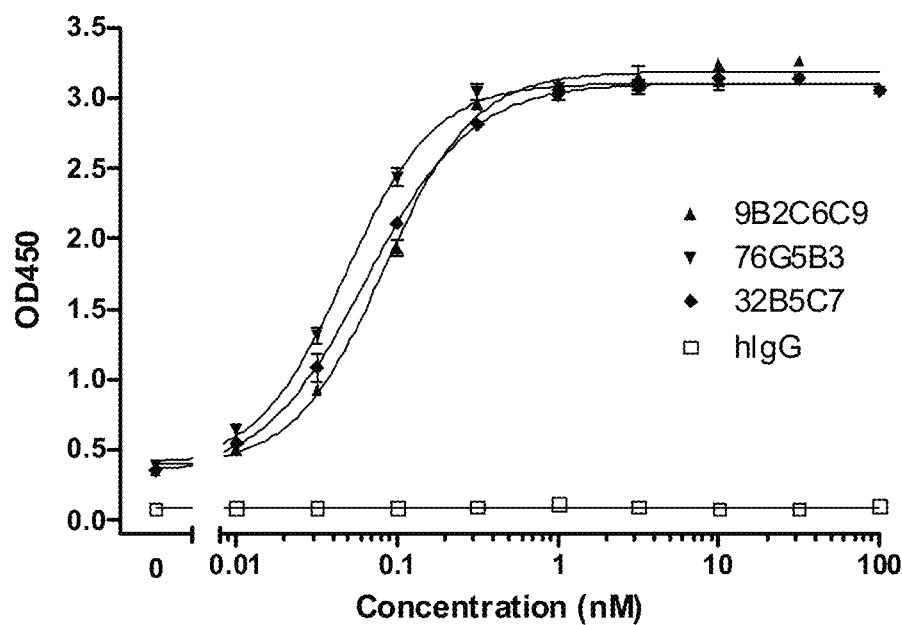
FIG. 4A and FIG. 4B show the binding activity of chimeric anti-PD-1 antibodies according to embodiments of the invention to human PD-1-hFc protein, as measured by ELISA.
Figure 4B:
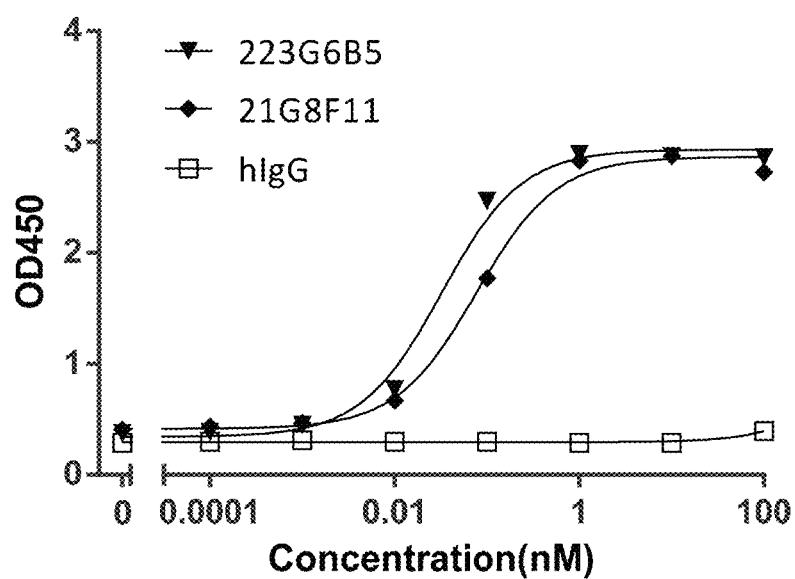
Figure 5A:
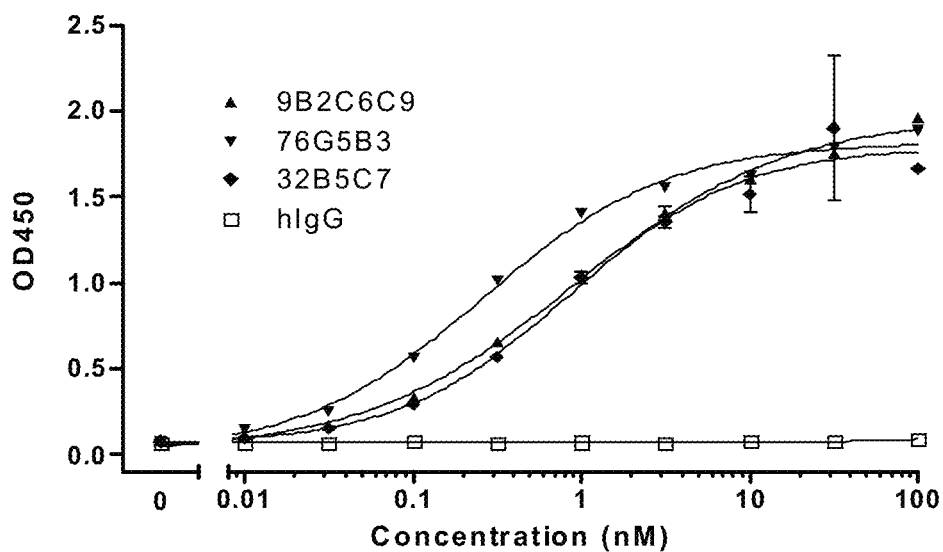
FIG. 5A and FIG. 5B show the binding activity of chimeric anti-PD-1 antibodies according to embodiments of the invention to cyno monkey PD-1-hFc protein, as measured by ELISA.
Figure 5B:
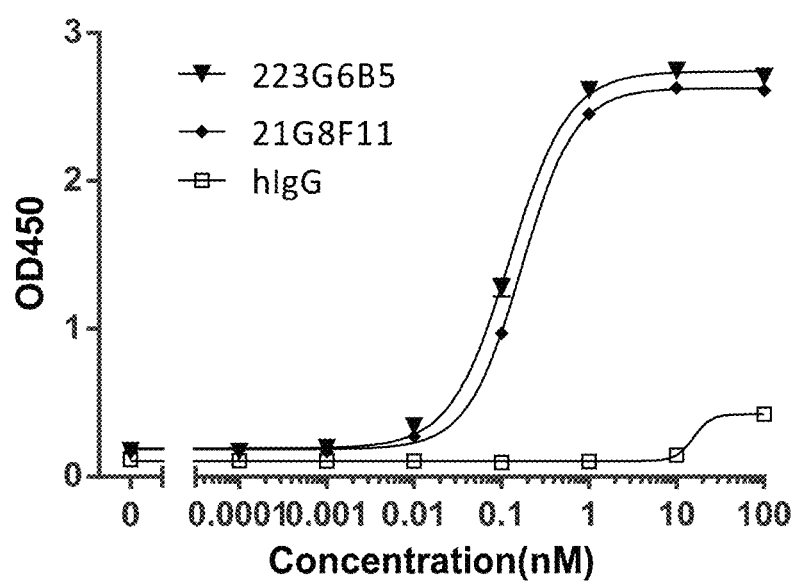
Figure 6A:
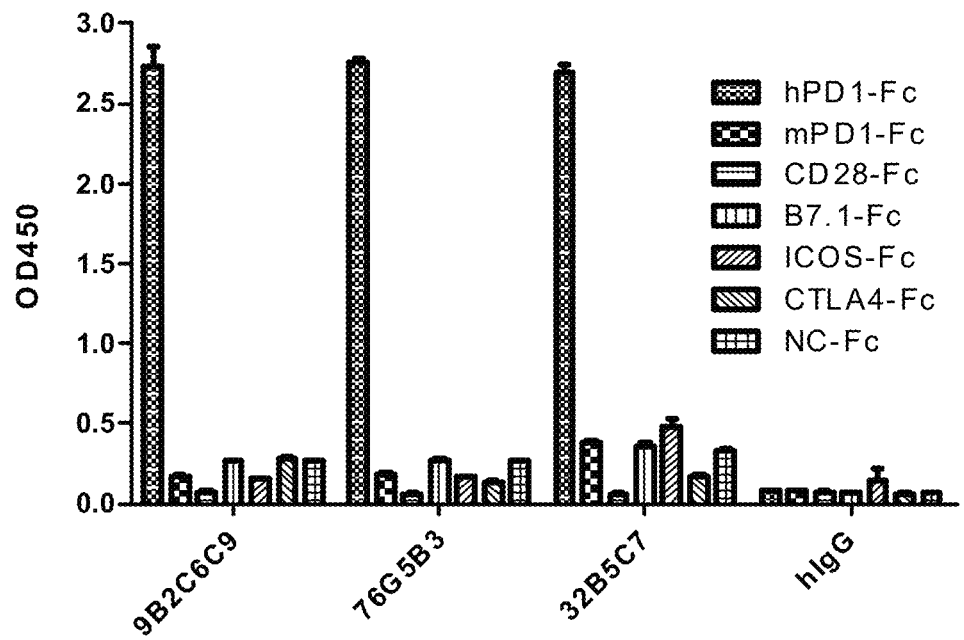
FIG. 6A and FIG. 6B show the binding activity of chimeric anti-PD-1 antibodies according to embodiments of the invention to other immune checkpoint proteins, as measured by ELISA.
Figure 6B:
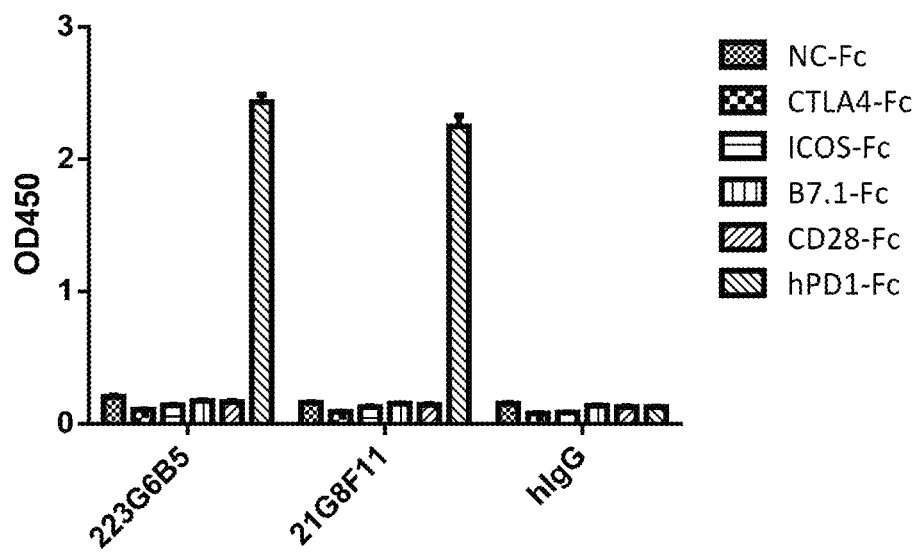

Purified Immunogen A (hPD-1$^{ECD}$-hFc protein) from Example 2, cyno PD-1$^{ECD}$-hFc protein (prepared using the method for preparing Immunogen A (see Example 2, step 1), comprising the amino acid sequence of the extracellular domain of cyno PD-1, which corresponds to amino acids Leu25-Gln167 of Uniprot database protein B0LAJ3), and other immune checkpoint proteins (CD28, B7-1, ICOS, CTLA4 and NC-Fc) (R&D Systems) were diluted to 1 ug/mL in PBS. 100 uL of the diluted recombinant proteins were added to each well of 96-well plate. The plates were sealed with plastic film and incubated at 4° C. overnight. The plates were washed twice with wash buffer (PBS+0.01% (v/v) Tween20), and incubated with blocking buffer (PBS+ 0.01% (v/v) Tween20+1% (w/w) BSA) at room temperature for 2 hours. The blocking buffer was aspirated away, and 100 uL of purified anti-PD-1 antibodies were added to each well and incubated for 2 hours at 37° C. The plates were washed three times with wash buffer (PBS+0.01% (v/v) Tween20). HRP-conjugated secondary antibody (Sigma) was added to each well and incubated for 2 hours at 37° C. After the plates were washed three times with wash buffer, 100 uL TMB substrate was added to each well and incubated for 30 minutes at room temperature. 100 uL stop solution (0.1N HCl) was added to each well to stop the reaction. The absorbance at 450 nm was measured with an ELISA plate reader (384plus SpectraMax, Molecular Devices). The results are shown in FIGS. 4-6 and in Tables 7-9. The IgG control was human IgG.

TABLE 9

Binding activities of chimeric anti-PD-1 mAbs to other immune checkpoint proteins, as measured by ELISA

| | $OD_{450\,nm}$ Immune check point proteins | | | | | |
|---|---|---|---|---|---|---|
| Clone ID | hPD 1 | CD28 | B7.1 | ICOS | CTLA4 | NC-Fc |
| 9B2C6C9 | 2.732 | 0.066 | 0.27 | 0.161 | 0.281 | 0.264 |
| 76G5B3 | 2.761 | 0.061 | 0.271 | 0.173 | 0.135 | 0.268 |
| 32B5C7 | 2.694 | 0.062 | 0.36 | 0.483 | 0.172 | 0.327 |
| 223G6B5 | 2.43 | 0.166 | 0.174 | 0.140 | 0.106 | 0.207 |
| 21G8F11 | 2.25 | 0.144 | 0.154 | 0.128 | 0.091 | 0.161 |
| IgG control | 0.082 | 0.064 | 0.07 | 0.142 | 0.062 | 0.068 |

(Part B) Detection of the Binding of Anti-PD-1 Antibodies to Cells Expressing PD-1 by Flow Cytometry CHO-K1 cells were stably transfected with pIRES plasmid containing the nucleic acid sequence encoding full length human PD-1 (see Example 2, step 2) to generate CHO-K1 cells stably expressing human PD-1 (herein

TABLE 7

Binding activities of chimeric anti-PD-1 mAbs to human PD-1$^{ECD}$-hFc, as measured by ELISA

| | $OD_{450\,nm}$ Antibody concentration (nM) | | | | | | | | |
|---|---|---|---|---|---|---|---|---|---|
| Clone ID | 100 | 31.6 | 10 | 3.16 | 1 | 0.316 | 0.1 | 0.0316 | 0.01 | 0.00316 |
| 9B2C6C9 | 3.07 | 3.26 | 3.25 | 3.14 | 3.10 | 2.95 | 1.93 | 0.93 | 0.50 | 0.36 |
| 76G5B3 | 3.05 | 3.13 | 3.12 | 3.07 | 3.07 | 3.04 | 2.43 | 1.31 | 0.65 | 0.38 |
| 32B5C7 | 3.05 | 3.14 | 3.14 | 3.07 | 3.02 | 2.81 | 2.11 | 1.09 | 0.55 | 0.36 |
| IgG control | 0.10 | 0.08 | 0.08 | 0.09 | 0.12 | 0.10 | 0.09 | 0.09 | 0.09 | 0.08 |

| | $OD_{450\,nm}$ Antibody concentration (nM) | | | | | | |
|---|---|---|---|---|---|---|---|
| Clone ID | 100 | 10 | 1 | 0.1 | 0.01 | 0.001 | 0.0001 | 0.00001 |
| 223G6B5 | 2.86 | 2.87 | 2.89 | 2.47 | 0.771 | 0.451 | 0.385 | 0.375 |
| 21G8F11 | 2.73 | 2.87 | 2.83 | 1.77 | 0.669 | 0.468 | 0.433 | 0.405 |
| 226C3A7 | 2.83 | 2.86 | 2.86 | 2.54 | 0.90 | 0.45 | 0.40 | 0.39 |
| 204C5E12 | 2.77 | 2.84 | 2.87 | 2.13 | 0.68 | 0.48 | 0.43 | 0.43 |
| IgG Control | 0.395 | 0.287 | 0.288 | 0.297 | 0.298 | 0.311 | 0.298 | 0.287 |

TABLE 8

Binding activities of chimeric anti-PD-1 mAbs to Cyno Monkey PD-1$^{ECD}$-hFc, as measured by ELISA

| | $OD_{450\,nm}$ Antibody concentration (nM) | | | | | | | | |
|---|---|---|---|---|---|---|---|---|---|
| Clone ID | 100 | 31.6 | 10 | 3.16 | 1 | 0.316 | 0.1 | 0.0316 | 0.01 | 0.00316 |
| 9B2C6C9 | 1.96 | 1.75 | 1.61 | 1.41 | 1.05 | 0.65 | 0.33 | 0.17 | 0.11 | 0.07 |
| 76G5B3 | 1.89 | 1.78 | 1.62 | 1.56 | 1.40 | 1.01 | 0.56 | 0.25 | 0.14 | 0.07 |
| 32B5C7 | 1.66 | 1.90 | 1.51 | 1.35 | 1.03 | 0.57 | 0.29 | 0.15 | 0.10 | 0.08 |
| IgG control | 0.09 | 0.07 | 0.07 | 0.07 | 0.07 | 0.07 | 0.08 | 0.07 | 0.07 | 0.07 |

Figure 7A:
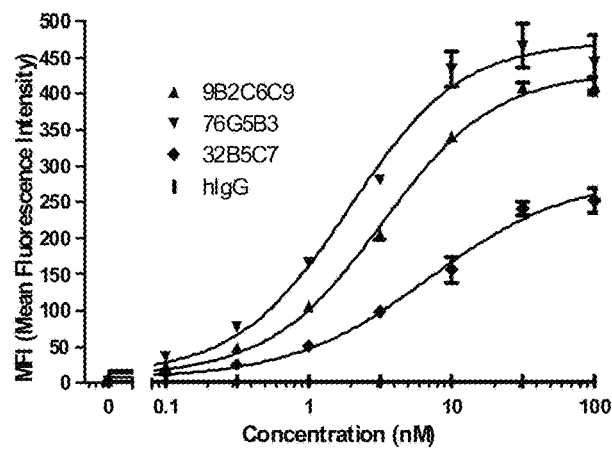
FIGS. 7A-7C show the cell-based binding activity of chimeric anti-PD-1 antibodies according to embodiments of the invention to CHO-K1-hPD-1, as measured by flow cytometry.
Figure 7B:
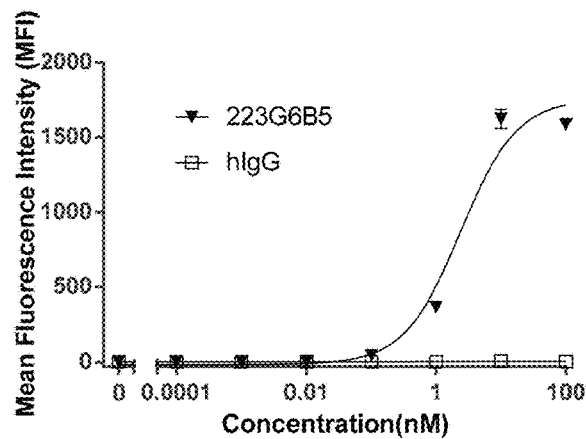
Figure 7C:
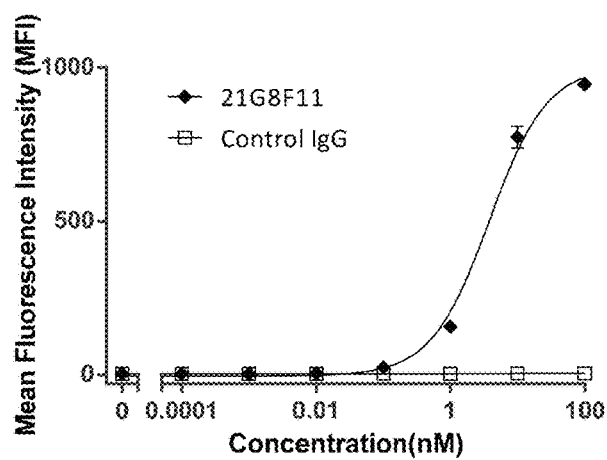
Figure 8A:
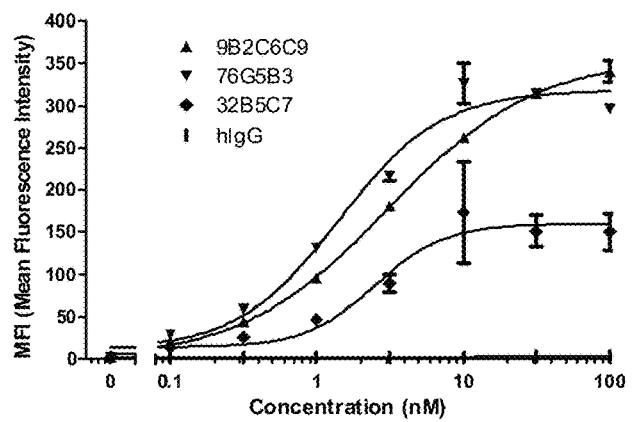
FIGS. 8A-8C show the cell-based binding activity of chimeric anti-PD-1 antibodies according to embodiments of the invention to CHO-K1-cPD-1, as measured by flow cytometry.
Figure 8B:
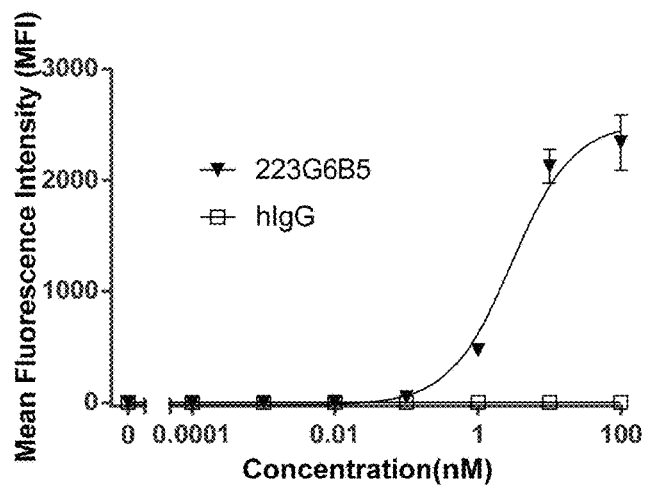
Figure 8C:
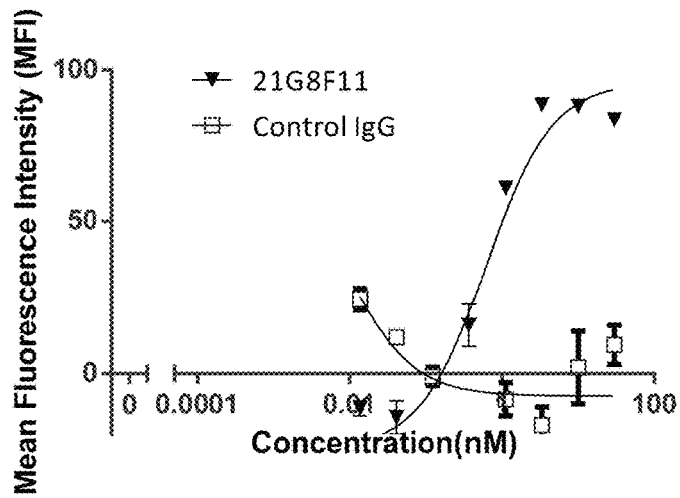

| | $OD_{450\,nm}$ Antibody concentration (nM) | | | | | | |
|---|---|---|---|---|---|---|---|
| Clone ID | 100 | 10 | 1 | 0.1 | 0.01 | 0.001 | 0.0001 | 0.00001 |
| 223G6B5 | 2.70 | 2.74 | 2.61 | 1.28 | 0.342 | 0.193 | 0.170 | 0.174 |
| 21G8F11 | 2.61 | 2.63 | 2.45 | 0.972 | 0.270 | 0.172 | 0.182 | 0.171 |
| IgG Control | 0.423 | 0.146 | 0.105 | 0.097 | 0.105 | 0.106 | 0.110 | 0.116 | referred to as CHO-K1-hPD-1 cells). Other CHO-K1 were stably transfected with pIRES plasmid containing the nucleic acid sequence encoding full length cyno PD-1 to generate CHO-K1 cells stably expressing cyno PD-1 (herein referred to as CHO-K1-cPD-1 cells). CHO-K1-hPD-1 and CHO-K1-cPD-1 cells were cultured and expanded in T-75 culture flasks to 90% confluence. The culture media was aspirated, and the cells were washed twice with HBSS (Hanks Balanced Salt Solution, Invitrogen). The cells were treated with enzyme-free cell dissociation solution (Versene solution, Invitrogen) and collected. The cells were then washed twice with HBSS, cell counts were determined, and cells were resuspended with HBSS at $2\times10^6$ cells/mL. Goat serum was added to the cell suspension to a final concentration of 1%, and the cells were blocked for 30 minutes on ice and then washed twice with HBSS. The cells were collected after centrifugation and resuspended in FACS buffer (HBSS+1% BSA, v/v) at $2\times10^6$ cells/mL. 100 uL of the cell suspension were then added to each well of 96-well plate. 100 uL of purified anti-PD-1 antibodies from Example 2 were added to each well of the 96-well plate and incubated for 2 hours on ice. Cells were washed twice with FACS buffer, and 100 uL of Alexa 488-labeled secondary antibody (Invitrogen) were added to the 96-well plate and incubated for 1 hour on ice. The samples were washed three times with FACS buffer, and 100 uL fixation buffer (4% paraformaldehyde v/v) were added to each well and incubated for 10 minutes. The cells were then washed twice with FACS buffer and resuspended in 100 uL FACS buffer. The mean fluorescence intensity (MFI) was determined using FACS Calibur (BD), and the results are shown in FIGS. 7-8 and in Tables 10-11. The IgG control was human IgG, and the values in the tables are the mean fluorescence intensity of the cell population.

TABLE 10

Binding activities of chimeric anti-PD-1 mAbs to CHO-K1-hPD-1, as determined by FACS

| | Mean fluorescence intensity Antibody concentration (nM) | | | | | | | |
|---|---|---|---|---|---|---|---|---|
| Clone ID | 100 | 31.6 | 10 | 3.16 | 1 | 0.316 | 0.1 | 0.0316 |
| 9B2C6C9 | 410.6 | 407.6 | 340.7 | 206.1 | 105.05 | 49 | 23.4 | 2.15 |
| 76G5B3 | 443.2 | 466.25 | 434.55 | 279.9 | 165.95 | 76.8 | 36.25 | 2.2 |
| 32B5C7 | 252.55 | 241.2 | 155.9 | 97.5 | 51.1 | 26.1 | 13.2 | 2.1 |
| 226C3A7 | 824.7 | 825.5 | 203.2 | 22.9 | 5.2 | 3.4 | 3.2 | 4.1 |
| 204C5E12 | 1492.9 | 985.5 | 160.2 | 21.4 | 5.0 | 3.0 | 2.9 | 3.0 |
| IgG control | 2.75 | 2.5 | 2.25 | 2.2 | 2.15 | 2.15 | 2.15 | 2.25 |

| | Mean fluorescence intensity Antibody concentration (nM) | | | | | | | |
|---|---|---|---|---|---|---|---|---|
| Clone ID | 100 | 10 | 1 | 0.1 | 0.01 | 0.001 | 0.0001 | 0.00001 |
| 223G6B5 | 1587 | 1623 | 369.0 | 45.0 | 7.9 | 4.2 | 3.3 | 3.3 |
| 21G8F11 | 661.1 | 696.2 | 165.6 | 22.8 | 5.4 | 3.1 | 2.9 | 2.9 |
| IgG Control | 4.3 | 8.3 | 3.6 | 3.1 | 2.9 | 2.9 | 3.1 | 2.7 |

TABLE 11

Binding activities of chimeric anti-PD-1 mAbs to CHO-K1-cPD-1, as determined by FACS

| | Mean fluorescence intensity Antibody concentration (nM) | | | | | | | |
|---|---|---|---|---|---|---|---|---|
| Clone ID | 100 | 31.6 | 10 | 3.16 | 1 | 0.316 | 0.1 | 0.0316 |
| 9B2C6C9 | 340.4 | 313.8 | 262.2 | 180.8 | 94.6 | 43.3 | 21.1 | 2.2 |
| 76G5B3 | 296.7 | 314.5 | 326.2 | 217.3 | 131.7 | 59.3 | 28.4 | 2.3 |
| 32B5C7 | 150.2 | 151.4 | 173.9 | 89.0 | 46.3 | 25.8 | 13.7 | 2.2 |
| 226C3A7 | 932.6 | 848.4 | 220.8 | 28 | 5.8 | 3.6 | 3.3 | 3.3 |
| 204C5E12 | 944.5 | 772.9 | 156.3 | 23.4 | 5.1 | 3.1 | 3.1 | 2.9 |
| IgG control | 2.9 | 3.0 | 2.4 | 2.3 | 2.2 | 2.2 | 2.2 | 2.2 |

| | Mean fluorescence intensity Antibody concentration (nM) | | | | | | | |
|---|---|---|---|---|---|---|---|---|
| Clone ID | 100 | 10 | 1 | 0.1 | 0.01 | 0.001 | 0.0001 | 0.00001 |
| 223G6B5 | 2339 | 2125 | 474.6 | 50.6 | 8.9 | 4.0 | 3.3 | 3.3 |
| 21G8F11 | 944.5 | 772.9 | 156.3 | 23.4 | 5.1 | 3.1 | 3.1 | 2.9 |
| IgG Control | 5.0 | 4.5 | 3.2 | 3.6 | 3.2 | 3.0 | 3.0 | 2.9 |

(Part C) Binding Affinity and Dissociation Constant of Anti-PD-1 Antibodies

Dissociation constants were determined by Octed red 96 (Fortiebio). The detailed operation and methods were followed according to the specifications of the instrument provided by the manufacturer. Briefly, a streptavidin sensor (SA sensor, Fortiebio) was used for the affinity determination. Biotinylated PD-1$^{ECD}$-hFc (Immunogen A) was diluted to 10 ug/mL in PBS buffer (pH7.4) containing 0.1% (w/w) BSA and 0.02% (v/v) Tween20 and incubated with the streptavidin sensor. Five different concentrations of anti-PD-1 antibody were incubated with the Immunogen A-loaded streptavidin sensor at 30° C. for 3 minutes. The reaction mixture was further incubated in PBS buffer (pH7.4) containing 0.1% (v/w) BSA and 0.02% (v/v) Tween20 at 30° C. for 5 minutes. The association and dissociation signals of anti-PD-1 antibodies to Immunogen A were recorded in real time using Octet Red 96. The affinity, association and dissociation constants were determined using Octet User software, and the results are shown in Table 12.

TABLE 12

Binding kinetics and affinities of anti-PD-1 chimeric mAbs to human PD-1$^{ECD}$-hFc protein, as determined by Octet Red 96

| Clone ID | $K_D$ (nM) | $k_a$ (l/Ms) | $k_d$ (l/s) |
|---|---|---|---|
| 9B2C6C9 | 0.269 | 9.01 × 10$^4$ | 2.43 × 10$^{-5}$ |
| 76G5B3 | 0.032 | 4.08 × 10$^5$ | 1.30 × 10$^{-5}$ |
| 32B5C7 | 0.045 | 2.12 × 10$^5$ | 9.64 × 10$^{-6}$ |

Example 4—Determination of the Ability of the Anti-PD-1 Antibodies to Block the Binding of PD-1 to its Ligands PD-L1 and PD-L2

Protein- and cell-based receptor ligand binding assays were performed to determine the ability of the anti-PD-1 antibodies to block the binding of PD-1 to its ligands PD-L1 and PD-L2.

Biotinylated recombinant PD-L1$^{ECD}$ and PD-L2$^{ECD}$ proteins were prepared as described for biotinylated recombinant PD-1$^{ECD}$-hFc in Example 2. The extracellular domain of PD-L1 corresponds to amino acids Phe19-THr239 of Uniprot database protein Q9NZQ7.1, and the extracellular domain of PD-L2 corresponds to amino acids Leu20-Pro219 of Uniprot database protein Q9BQ51.

Figure 9A:
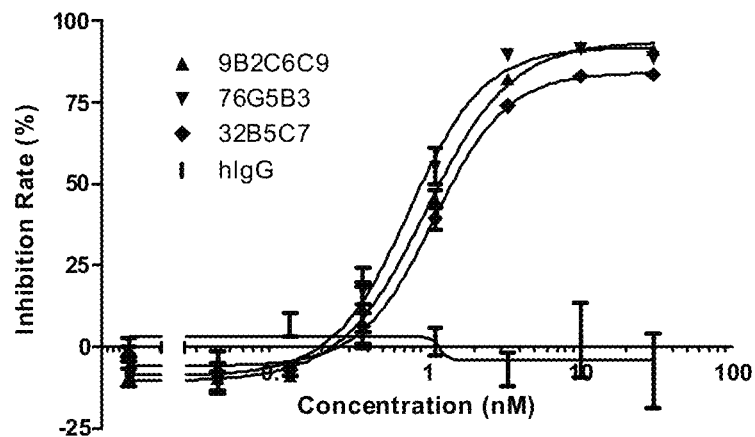
FIGS. 9A-9C show the inhibition of binding of PD-1 protein to its ligand PD-L1 by chimeric anti-PD-1 antibodies according to embodiments of the invention, as measured by a protein-based receptor ligand blocking assay.
Figure 9B:
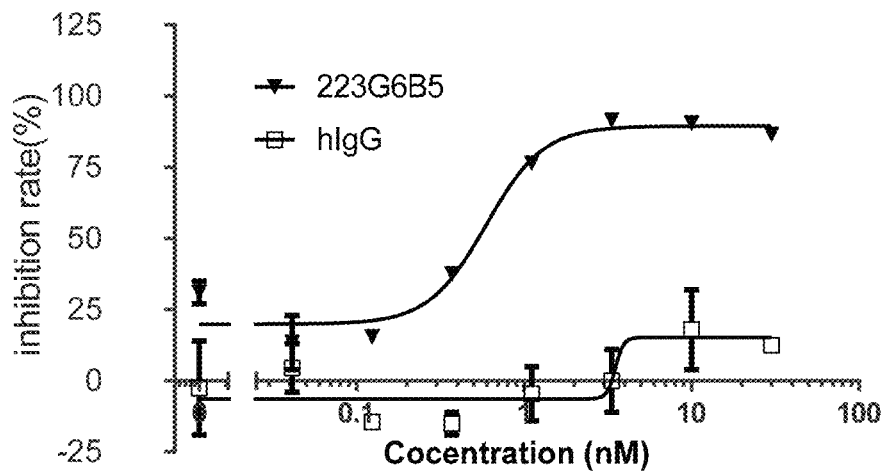
Figure 9C:
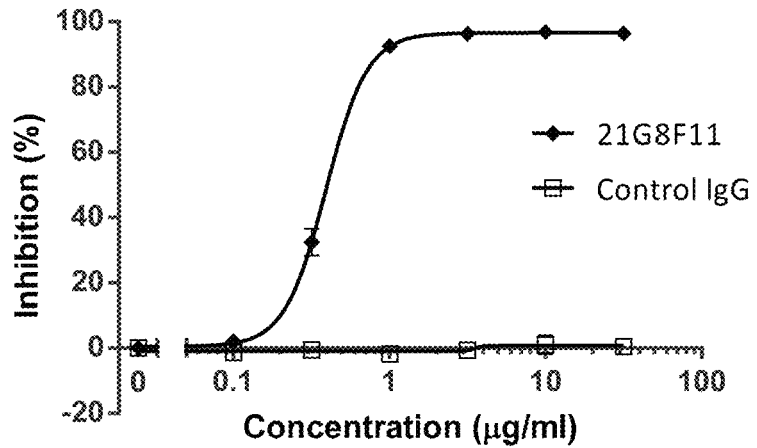
Figure 10A:
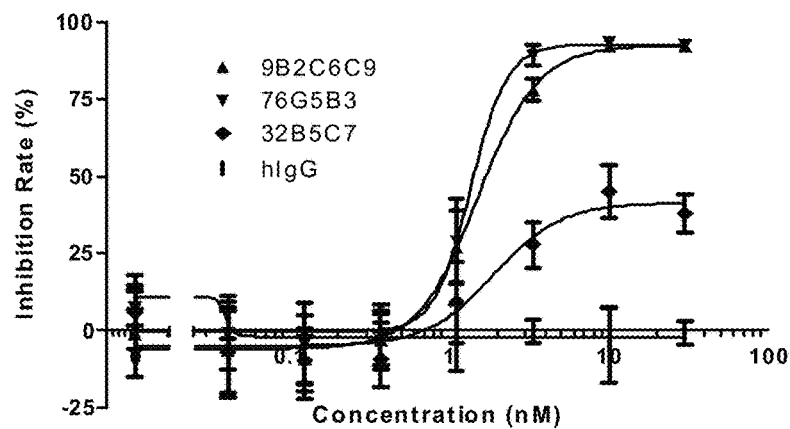
FIGS. 10A-10C show the inhibition of binding of PD-1 protein to its ligand PD-L2 by chimeric anti-PD-1 antibodies according to embodiments of the invention, as measured by a protein-based receptor ligand blocking assay.
Figure 10B:
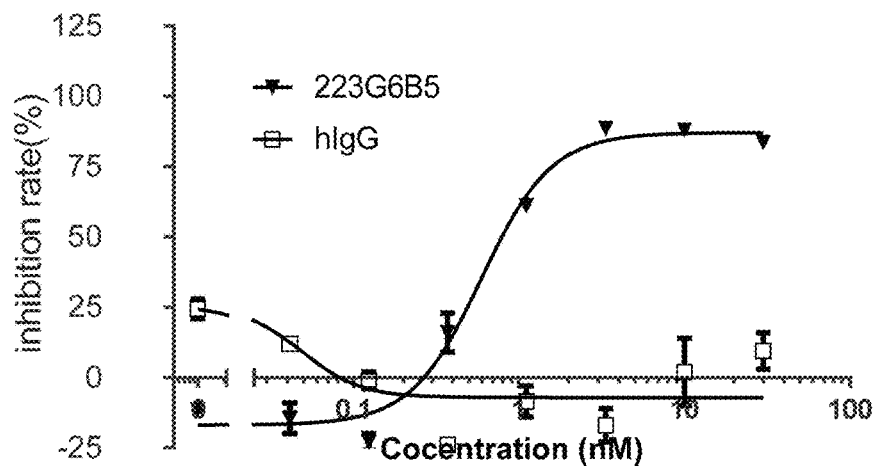
Figure 10C:
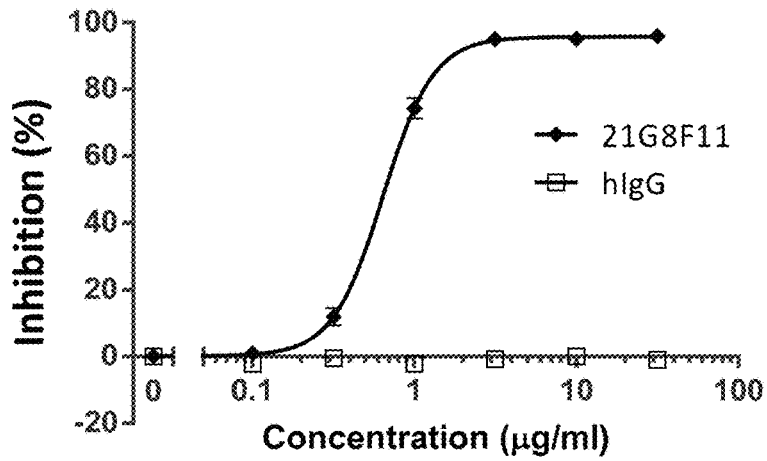

Purified PD-1$^{ECD}$-hFc (Example 2) was diluted with PBS to a final concentration of 1.0 ug/mL, and 100 uL diluted PD-1$^{ECD}$-hFc were added to each well of a 96-well plate that was then sealed with plastic film and incubated at 4° C. overnight. The plate was washed twice with wash buffer (PBS+0.01% (v/v) Tween 20) and incubated with blocking buffer (PBS+0.01% (v/v) BSA+1% Tween 20 (w/w)) at room temperature for 2 hours. The blocking buffer was aspirated, and 50 uL purified anti-PD-1 antibodies from Example 2 were added to each well of 96-well plate. 100 uL of biotinylated recombinant PD-L1$^{ECD}$ or PD-L2$^{ECD}$ protein were added to each well, mixed, and incubated at 37° C. for 2 hours. The plate was washed three times with wash buffer (PBS+0.01% (v/v) Tween 20). 100 uL HRP-conjugated streptavidin (Sigma) were then added to each well and incubated at 37° C. for 2 hours. The plate was then washed three times with wash buffer, and 100 uL TMB substrate were added to each well. After 30 minutes of incubation at room temperature, the reaction was stopped by adding 100 uL stop solution (0.1N HCl). The absorbance at OD450 nm was measured with an ELISA plate reader (384plus SpectraMax, Molecular Devices). The results, shown in FIGS. 9-10, demonstrate that the anti-PD-1 antibodies can block the binding of PD-1 to its ligands, PD-L1 and PD-L2.

Figure 11A:
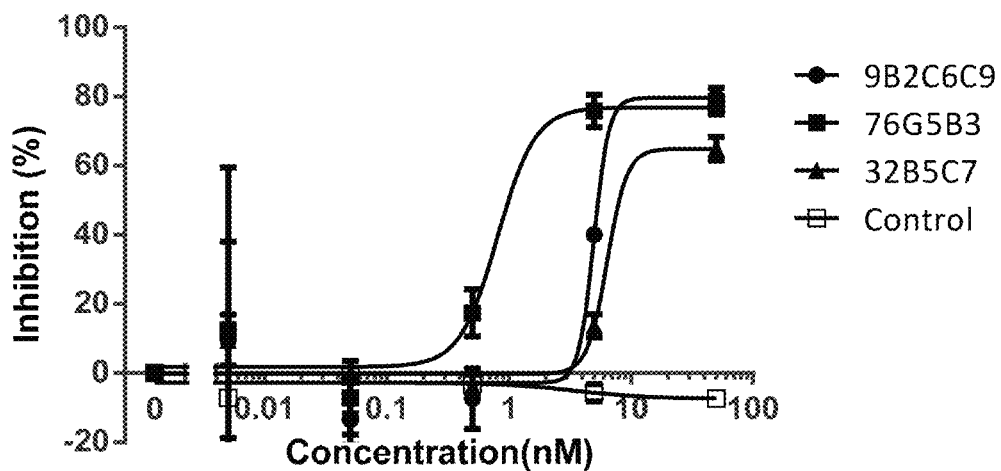
FIGS. 11A&11B show the inhibition of binding of PD-1 protein to its ligand PD-L1 by chimeric anti-PD-1 antibodies according to embodiments of the invention, as measured by a cell-based receptor ligand blocking assay.
Figure 11B:
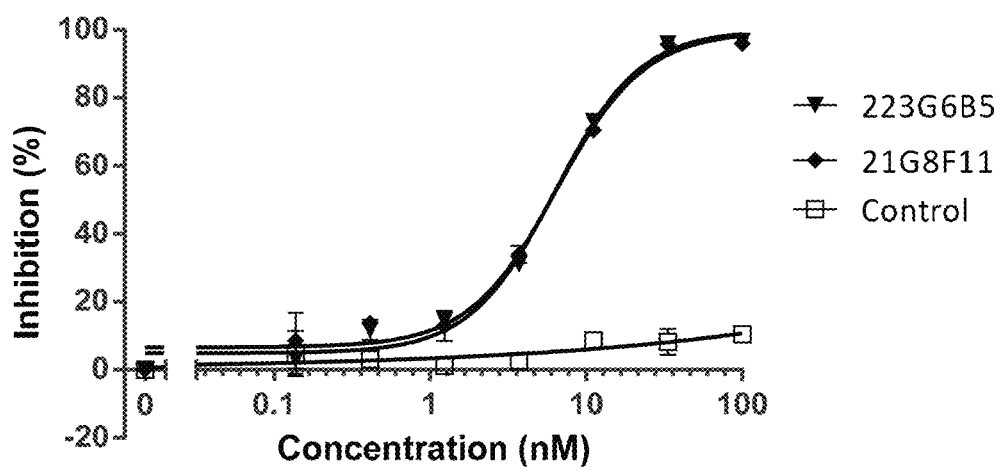
Figure 12A:
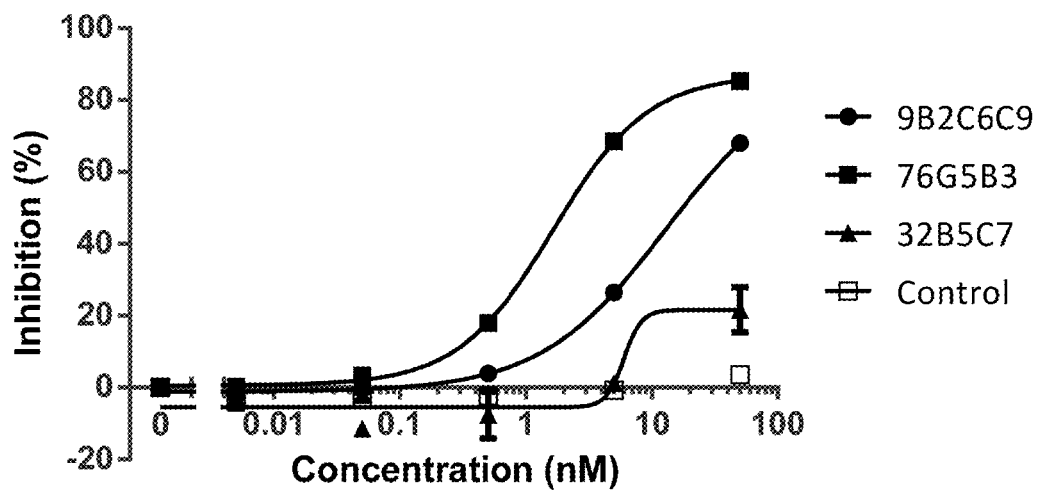
FIGS. 12A&12B show the inhibition of binding of PD-1 protein to its ligand PD-L2 by chimeric anti-PD-1 antibodies according to embodiments of the invention, as measured by a cell-based receptor ligand blocking assay.
Figure 12B:
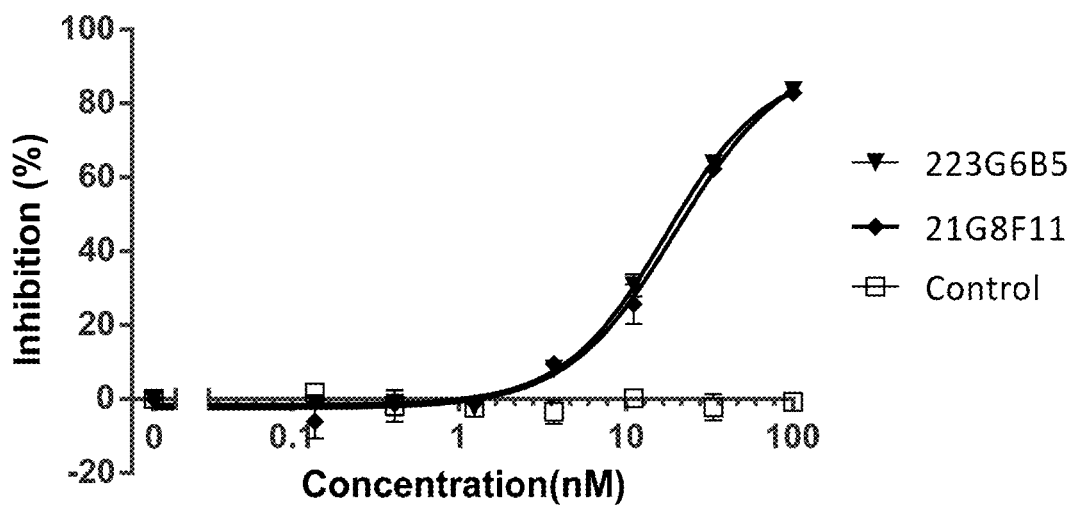

CHO-K1-hPD1 cells were cultured and expanded in T-75 culture flasks to 60-80% confluence. The culture media was aspirated, and the cells were washed twice with PBS. The cells were treated with TrypLE™ Express (Invitrogen) and collected. Trypsin was neutralized by the addition of 8 mL culture medium, and cell counts were determined. Cells were centrifuged at 300 g for 5 minutes and resuspended in blocking buffer at 1×10$^6$ cells/mL. The cells were blocked for 15 minutes at 37° C. Meanwhile, the wells of 96-well round-bottom plates were blocked with 200 uL blocking buffer for 1 hour at 37° C. The blocking buffer was discarded, and 200 uL cells were dispensed to each well of the 96-well plates (2×10$^5$ cells/well). The plates were centrifuged at 500 g for 5 minutes, and the supernatants were discarded. The cells were resuspended in 100 uL antibody prepared in blocking buffer. 100 uL of biotinylated PD-L1-Fc or biotinylated PD-L2-Fc (60 ug/mL in blocking buffer) were added to each well of 96-well plate and mixed by shaking gently. The plates were incubated at 4° C. for 90 minutes and washed twice with 200 uL blocking buffer. The blocking buffer was discarded, and the cells were resuspended in 100 uL streptavidin-Alexa 488 solution (1:500 in blocking buffer, Invitrogen) and incubated at 4° C. for 1 hour. The plates were washed three times with blocking buffer and resuspended in 200 uL blocking buffer. The mean fluorescence intensity (MFI) was determined using FACS Calibur (BD). The results, shown in FIGS. 11-12, demonstrate that the anti-PD-1 antibodies can block the binding of cell-expressed PD-1 to its ligands, PD-L1 and PD-L2.

Example 5—Lymphocyte Stimulation Assay to Examine the Ability of the Anti-PD-1 Antibodies to Block the Binding of PD-1 to its Ligands PD-L1 and PD-L2

(A) A T cell stimulation assay was performed to examine the effect of the anti-PD-1 antibodies on T cell stimulation by their blocking of the binding of PD-1 to its ligands PD-L1 and PD-L2.

(Step 1) Isolation of Peripheral Blood Mononuclear Cells (PBMCs) from Whole Blood by a Ficoll Gradient.

Whole blood was diluted with PBS at a ratio of 1:1 (v/v) and gently added on top of Ficoll solution (GE Healthcare) using a sterile pipette. The volume ratio of Ficoll to diluted whole blood was 3:4. The samples were centrifuged at 400 g at 20° C. for 30 minutes. Three layers of solution were formed after centrifugation, with the upper layer being plasma, and the middle milk white layer being mononuclear cells. A sterile pipette was used to collect the mononuclear cells from the middle layer and transfer them to a new centrifugal tube. Three times the sample volume of PBS was added, and the samples were centrifuged at 100 g at room temperature for 10 minutes. The supernatant was discarded, and the lymphocytes were resuspended with 10 mL PBS buffer. The lymphocytes were washed with PBS three times to remove blood platelets. The lymphocyte suspension was then resuspended with 10 mL RPMI1640 culture medium (Invitrogen) containing 10% FBS.

(Step 2) PBMC Stimulation Test

Constructs encoding full-length PD-L1 protein were generated by subcloning PD-L1 nucleotide sequence into pIRES plasmid (pIRES-puro-PD-L1). To anchor anti-CD3 (OKT3)

(see Kipriyanov et al., 1997, Peds. 10:445-453) into the cell membrane, OKT3 scFv was fused to the C-terminus of mouse CD8a (amino acids 113-220 of NCBI accession No: NP-1074579.1) and subcloned into pIRES-058 (see Sambrook and Russell, Id.). pIRES-puro-PD-L1 and pIRES-058 were co-transfected to CHO-K1 and 293F cells following the preparation method in Example 2 to generate the stable cell lines CHO-K1-PD-L1/OS8 and 293F-PD-L1/OS8. The cells were used to stimulate T lymphocytes. Before the experiments, CHO-K1-PD-L1/OS8 and 293F-PD-L1/OS8 cells were treated with 10 ug/mL mitomycin at 37° C. for 3 hours.

100 uL PBMC (containing $5 \times 10^4$ cells) were added to the wells of a 96-well plate, and the test antibody solution was then added to the 96-well plate and incubated for 15 minutes at room temperature. 50 uL of $5 \times 10^3$ CHO-K1-PD-L1/OS8 or 293F-PD-L1/OS8 were added to each well and cultured at 37° C., 5% $CO_2$ for 72 hours. The supernatants were collected and stored at −20° C. until analysis.

Figure 13:
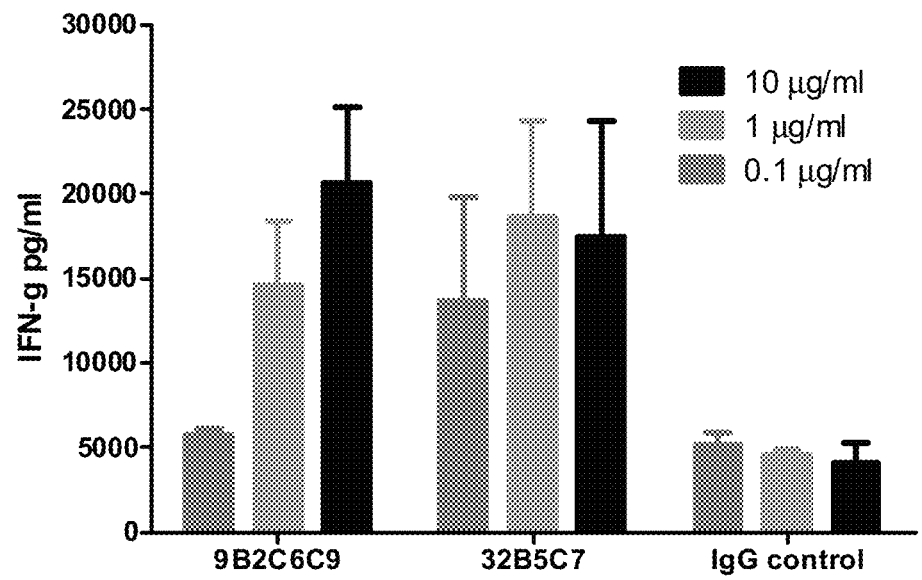
FIG. 13 shows the effect of chimeric anti-PD-1 antibodies according to embodiments of the invention on IFN-γ secretion in a T lymphocyte stimulation assay using PBMC's.

(Step 3) Detection of Interferon Gamma (IFN-γ) or Interleukin IL-2 Secretion by ELISA Quantification of the levels of IFN-γ or IL-2 in culture supernatant was carried out using Human IFN-gamma Quantikine ELISA Kit (R&D Systems SIF50) and Human IL-2 Quantikine ELISA Kit D2050 (R&D Systems S2050), respectively, following the manufacturer-provided operating instructions and kit reagents. Briefly, the IFN-γ and IL-2 polyclonal antibodies were coated onto the ELISA microplates, and 400 uL of culture supernatant as well as the standard were added to each well and incubated at room temperature for 2 hours. The plates were washed 4 times with wash buffer, followed by the addition of HRP-conjugated anti-human IFN-γ and IL-2 antibodies, and incubated at room temperature for 2 hours. After washes, a chromogenic substrate was added and incubated in the dark at room temperature for 30 minutes, and the reaction was terminated by the addition of a stop solution. The absorbance at 450 nm was determined using an ELISA plate reader, and the results, shown in FIG. 13 and in Table 13, demonstrate that the anti-PD-1 antibodies analyzed by the PBMC lymphocyte stimulation test can increase IFN-γ secretion. The IgG control is human IgG, and the values listed in the table are the IFN-γ concentrations in the culture supernatant (pg/mL).

TABLE 13

Chimeric anti-PD-1 mAbs induce IFN-γ release from stimulated PBMCs

| | IFN-γ (pg/mL) Antibody Concentration (ug/mL) | | |
|---|---|---|---|
| Clone ID | 10 | 1 | 0.1 |
| 9B2C6C9 | 20596.6 | 14651.4 | 5805.1 |
| 76G5B3 | 17419.6 | 18640.1 | 13643.3 |
| IgG Control | 4036.6 | 4544.7 | 5193.8 |

(B) A mixed lymphocyte reaction was performed to examine the impact of the anti-PD-1 antibodies on T cell stimulation by their blocking of the binding of PD-1 to its ligands PD-L1 and PD-L2.

(Step 1) Isolation and Culture of Dendritic Cells from Human CD14+ Cells

FicollPaque Plus (GE Healthcare) was used to isolate PBMCs from whole blood, following the manufacturer-provided instructions. The protocol was the same as that described in Example 5A, step 1.

PBMCs were resuspended in RPMI 1640 complete medium containing 10% FBS, and the cell concentration was adjusted to $1 \times 10^5$ cells/mL. The cells were cultured in T-75 culture flasks at 37° C., 5% (v/v) $CO_2$ for 2 hours. The culture supernatant and non-adhered cells were transferred to a new T-75 culture flask, and the original T-75 culture flask was replenished with new RPMI 1640 complete culture medium supplemented with 10% FBS and incubated at 37° C. and 5% (v/v) $CO_2$ for 2 hours. The culture supernatant and non-adhered cells were removed, and the adherent cells were replenished with RPMI1640 culture media containing 10% FBS and incubated at 37° C., 5% (v/v) $CO_2$ for 18 hours. The culture supernatant and non-adhered cells were removed, and the adherent cells were replenished with RPMI1640 complete culture media supplemented with 500 U/mL recombinant human GM-CSF (PEPROTECH) and 500 U/mL recombinant human interleukin IL-4 (PEPROTECH) and cultured for 4 days. After 4 days, the culture media was replenished with complete RPMI 1640 media supplemented with GM-CSF and IL-4, and the cells were cultured for an additional 2 days. The culture medium was then replaced with RPMI 1640 complete media with 1 ug/mL LPS and incubated for 18 hours. Dendritic cells were then collected by adding PBS containing EDTA and centrifuging at 300 g for 5 minutes. The supernatant was aspirated, and the cells were washed once more with PBS. The collected human CD14+ dendritic cells were resuspended in RPMI 1640 complete media, and the cell counts were determined.

(Step 2) Isolation and Purification of Human CD4+ T Cells.

Human CD4+ T cells were isolated and purified from PBMCs using a MagCellect™ human CD4+ T Cell Isolation Kit (R&D Systems), following the manufacturer-provided instructions.

(Step 3) Mixed Lymphocyte Reaction

Purified CD4+ cells from different healthy volunteers were co-cultured with dendritic cells in 96-well plates. The cell densities were adjusted to $10^5$ cells per 80 uL. $10^5$ purified CD4+ T cells and $2 \times 10^4$ dendritic cells were added to each well of a 96-cell plate, purified anti-PD-1 antibodies from Example 2 were added to the appropriate wells in the plate, and the plates were incubated at 37° C. in a 5% $CO_2$ incubator for 6 days. The supernatants were collected, and the cytokine levels were determined.

(Step 4) Measurement of IFN-γ and IL-2 Levels in Supernatant by ELISA

Quantification of the levels of IFN-γ or IL-2 in the supernatants collected in the previous step was carried out using Human IFN-gamma Quantikine ELISA Kit (R&D Systems SIF50) and Human IL-2 Quantikine ELISA Kit D2050 (R&D Systems S2050), respectively, following the manufacturer-provided operating instructions and kit reagents.

Figure 14:
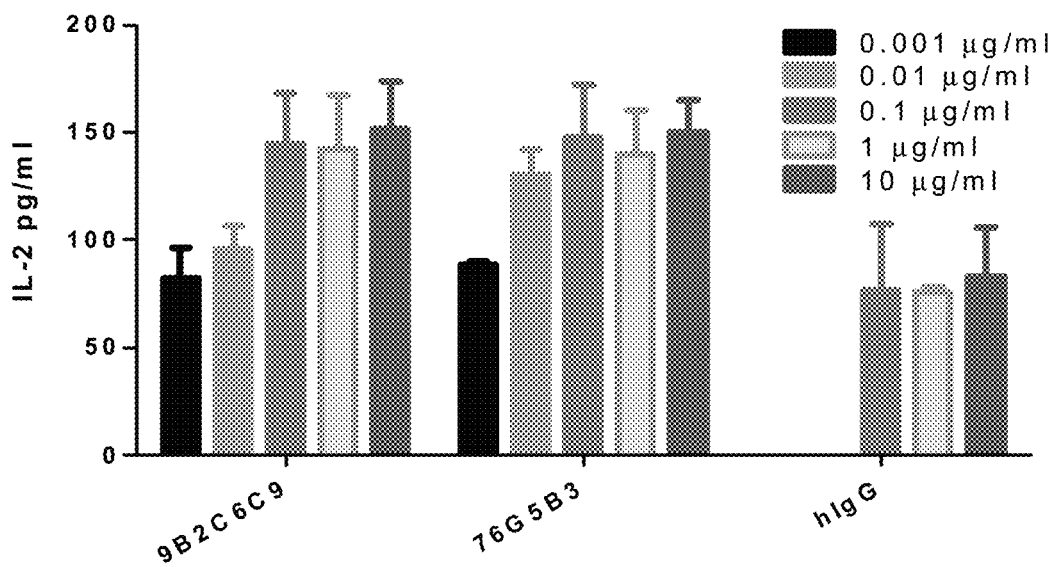
FIG. 14 shows the effect of chimeric anti-PD-1 antibodies according to embodiments of the invention on IL-2 secretion in a mixed lymphocyte reaction using PBMC's from donor 1.
Figure 15:
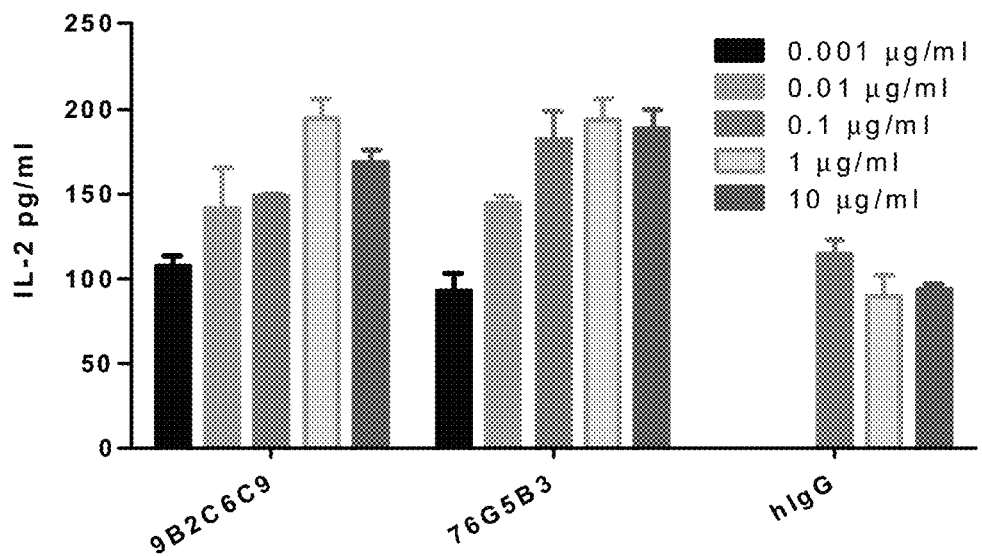
FIG. 15 shows the effect of chimeric anti-PD-1 antibodies according to embodiments of the invention on IL-2 secretion in a mixed lymphocyte reaction using PBMC's from donor 2.
Figure 16:
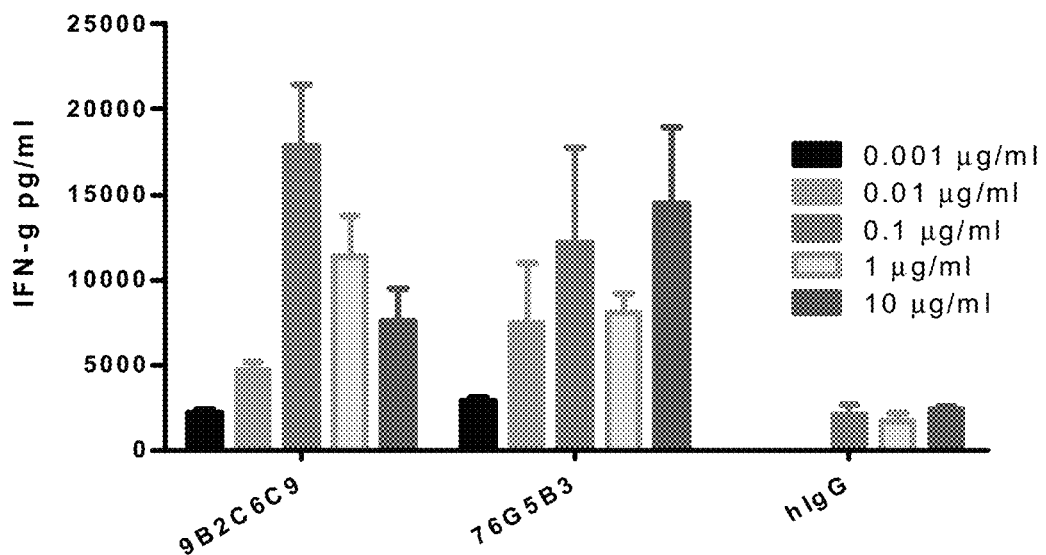
FIG. 16 shows the effect of chimeric anti-PD-1 antibodies according to embodiments of the invention on IFN-γ secretion in a mixed lymphocyte stimulation assay using PBMC's from donor 1.
Figure 17:
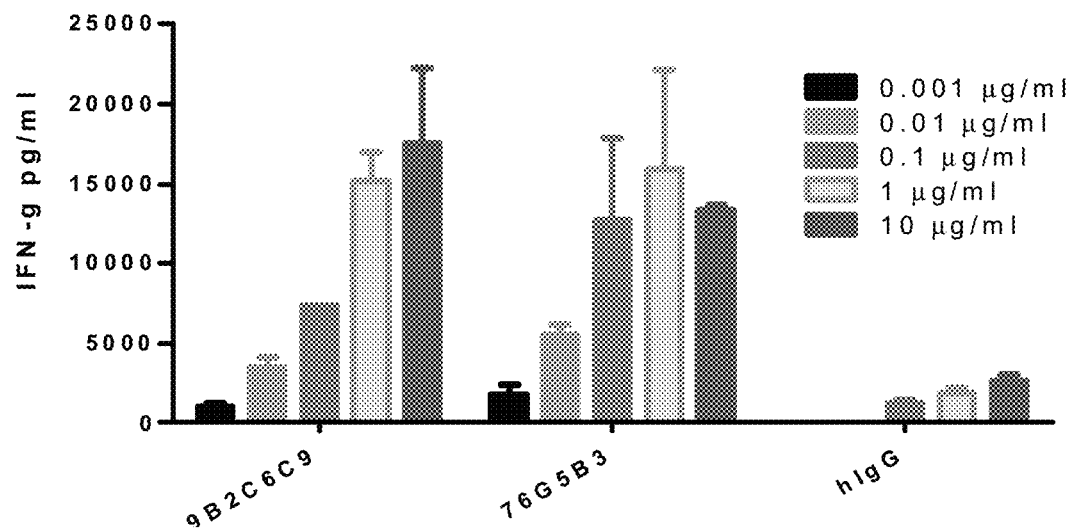
FIG. 17 shows the effect of chimeric anti-PD-1 antibodies according to embodiments of the invention on IFN-γ secretion in a mixed lymphocyte stimulation assay using PBMC's from donor 2.
Figure 18:
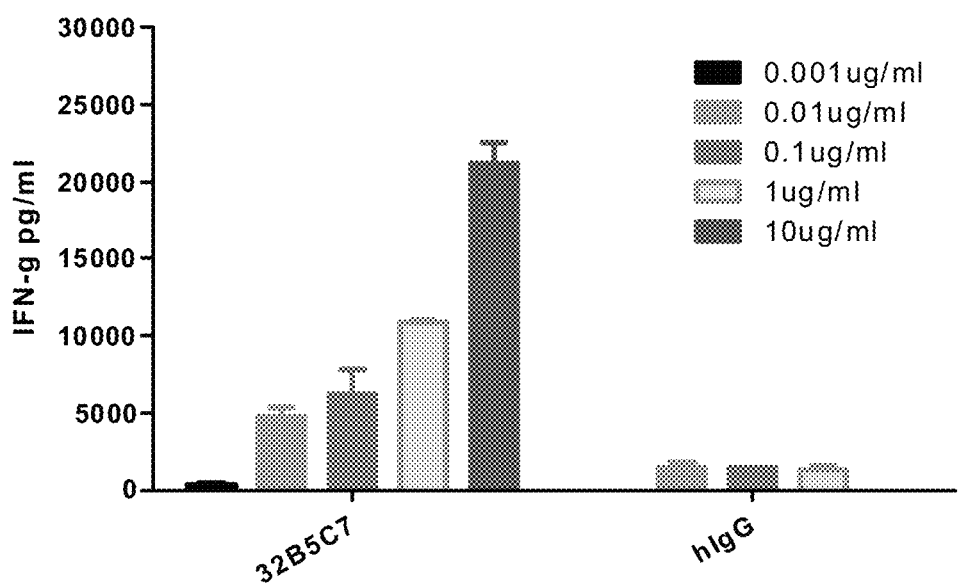
FIG. 18 shows the effect of chimeric anti-PD-1 antibodies according to embodiments of the invention on IFN-γ secretion in a mixed lymphocyte stimulation assay using PBMC's from donor 1.
Figure 19:
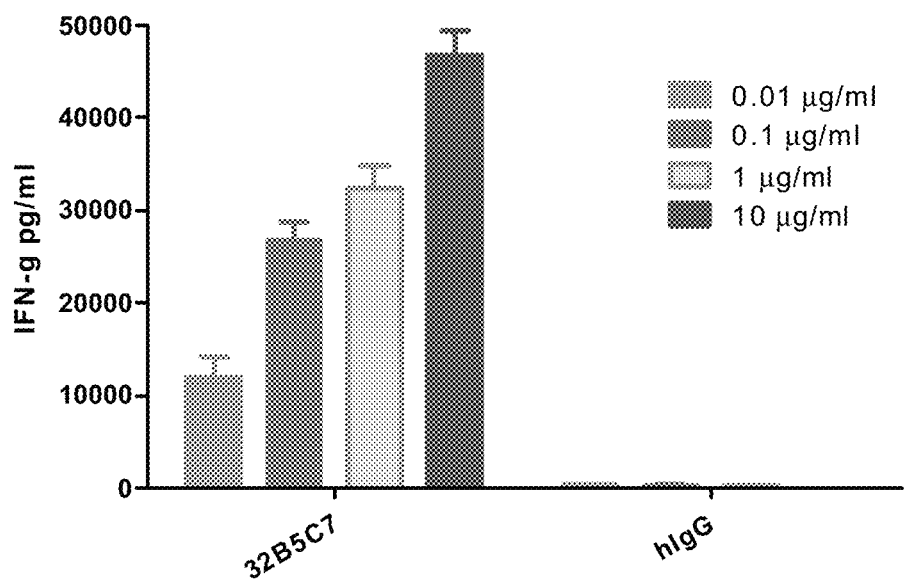
FIG. 19 shows the effect of chimeric anti-PD-1 antibodies according to embodiments of the invention on IFN-γ secretion in a mixed lymphocyte stimulation assay using PBMC's from donor 2.
Figure 20:
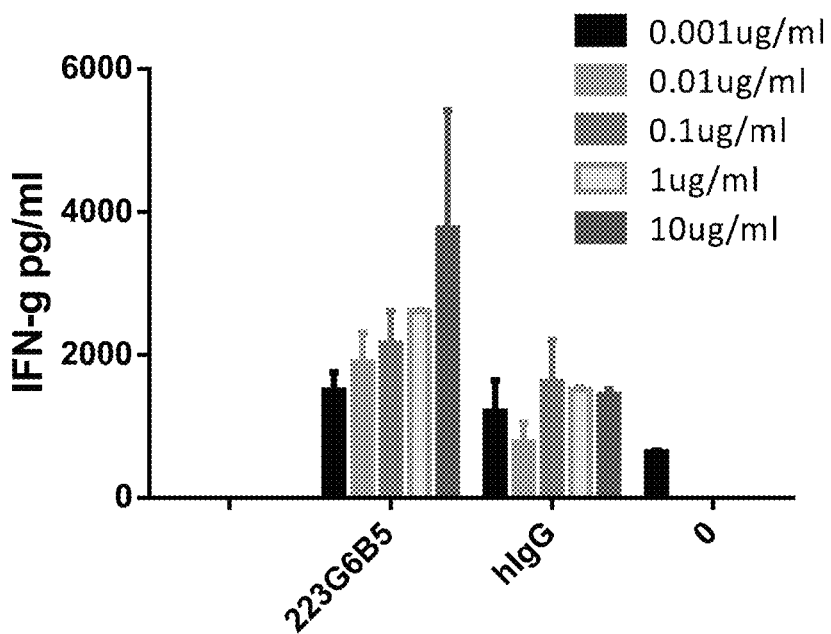
FIG. 20 shows the effect of chimeric anti-PD-1 antibodies according to embodiments of the invention on IFN-γ secretion in a mixed lymphocyte stimulation assay using PBMC's from donor 3.
Figure 21:
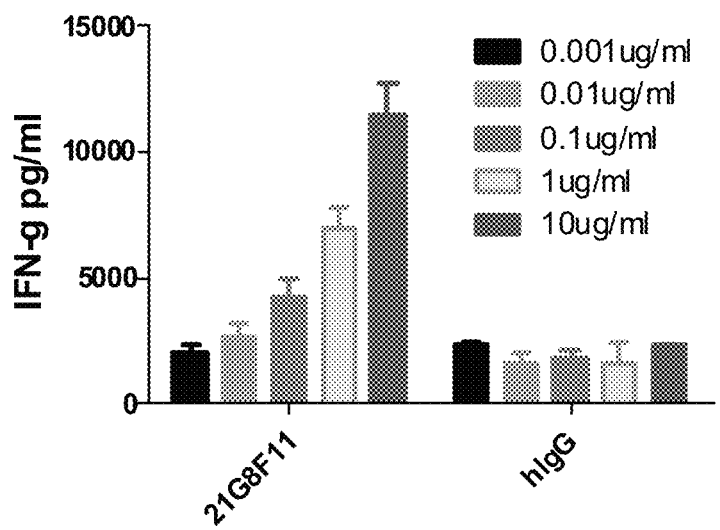
FIG. 21 shows the effect of chimeric anti-PD-1 antibodies according to embodiments of the invention on IFN-γ secretion in a mixed lymphocyte stimulation assay using PBMC's from donor 4.
Figure 22A:
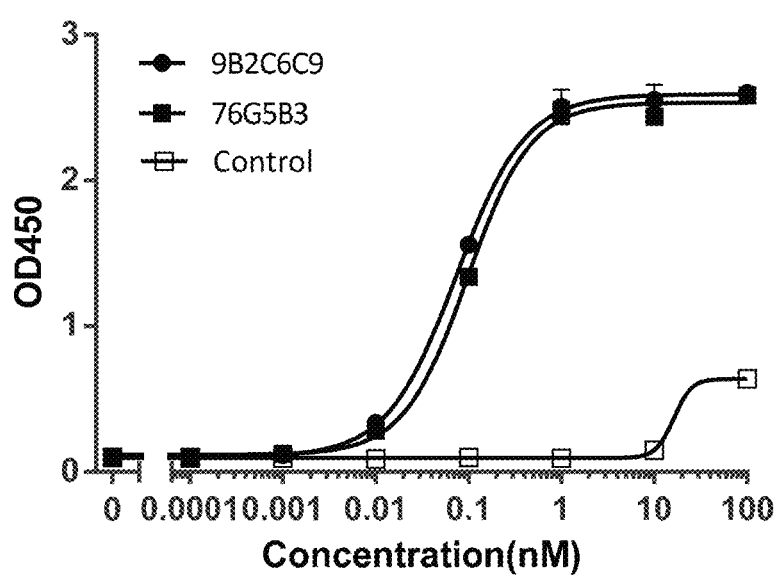
FIGS. 22A-22C show the binding activity of fully human anti-PD-1 antibodies according to embodiments of the invention to human PD-1-hFc protein, as measured by ELISA.
Figure 22B:
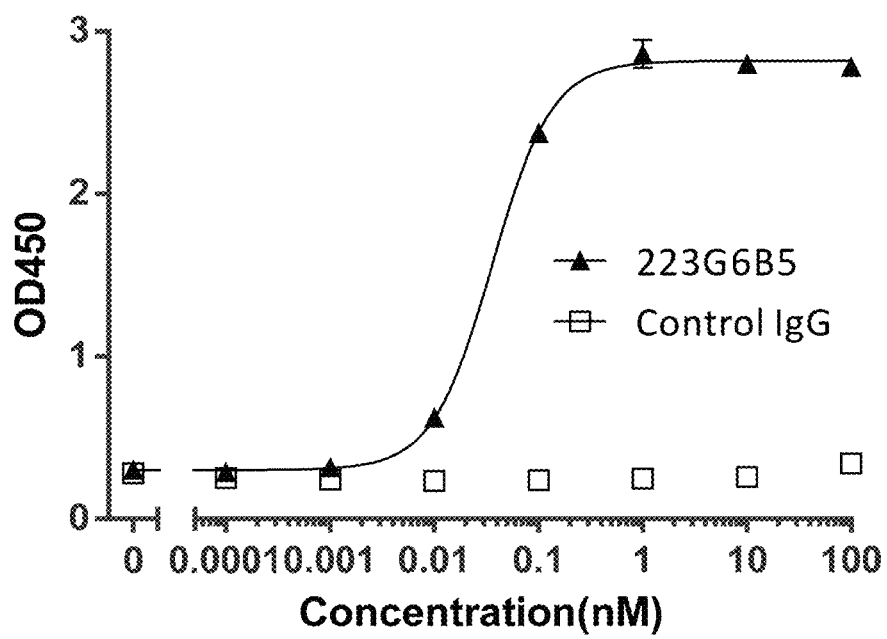
Figure 22C:
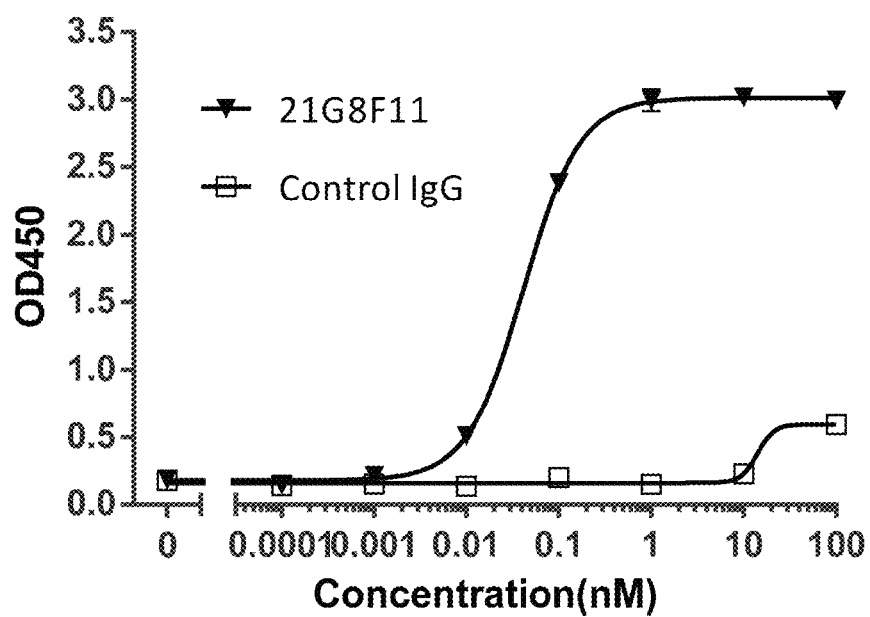
Figure 23A:
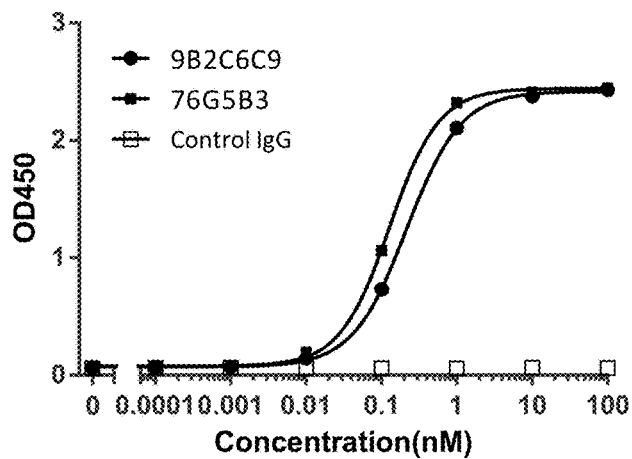
FIGS. 23A-23C show the binding activity of fully human anti-PD-1 antibodies according to embodiments of the invention to cyno monkey PD-1-hFc protein, as measured by ELISA.
Figure 23B:
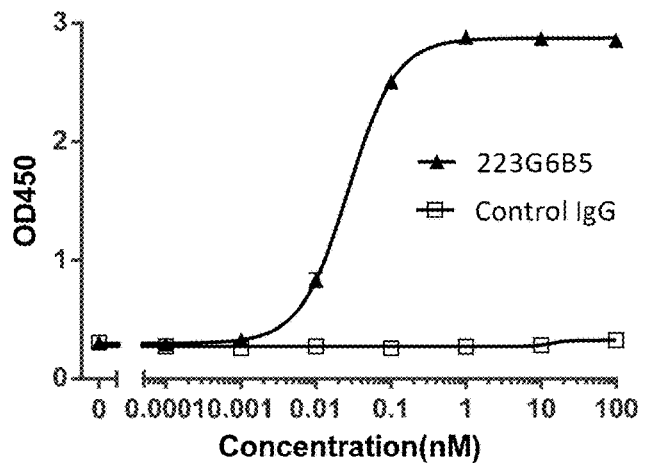
Figure 23C:
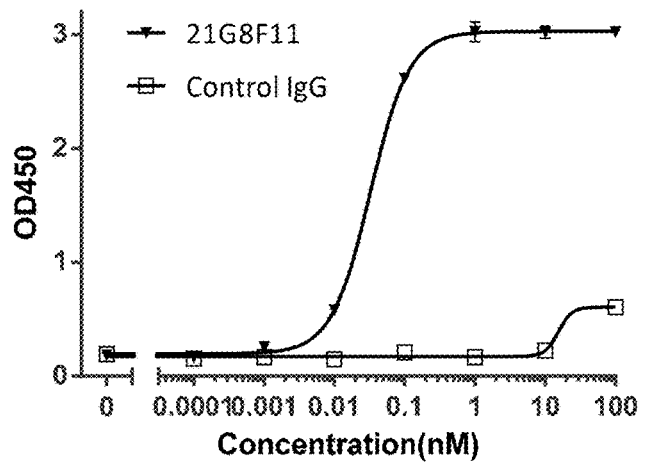
Figure 24A:
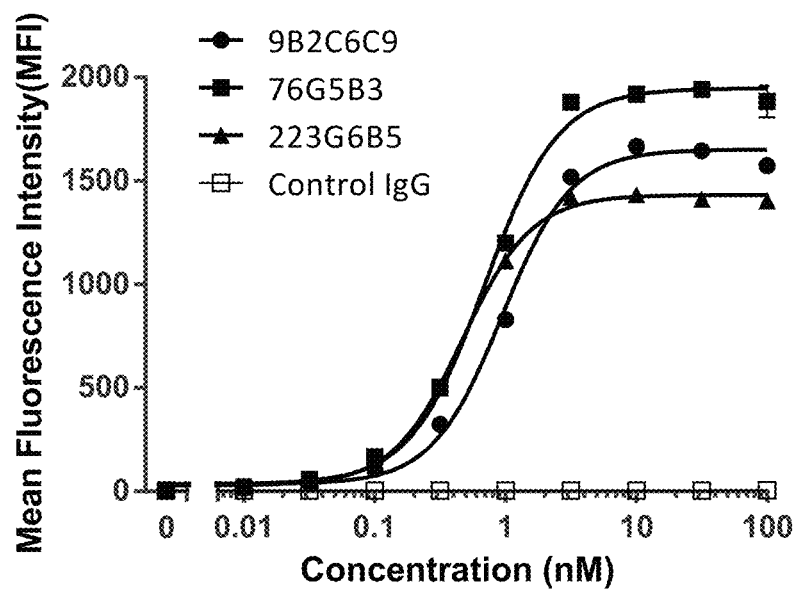
FIGS. 24A&24B show the cell-based binding activity of fully human anti-PD-1 antibodies according to embodiments of the invention to CHO-K1-hPD-1, as measured by flow cytometry.
Figure 24B:
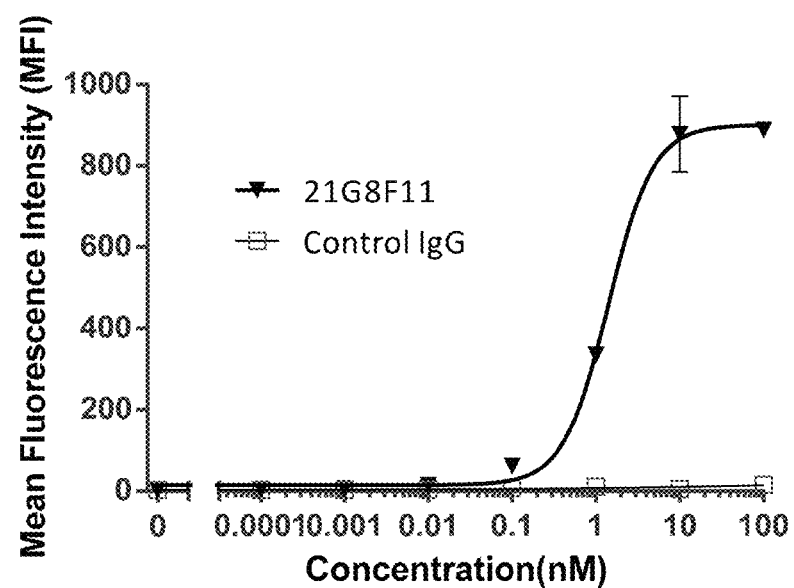
Figure 25A:
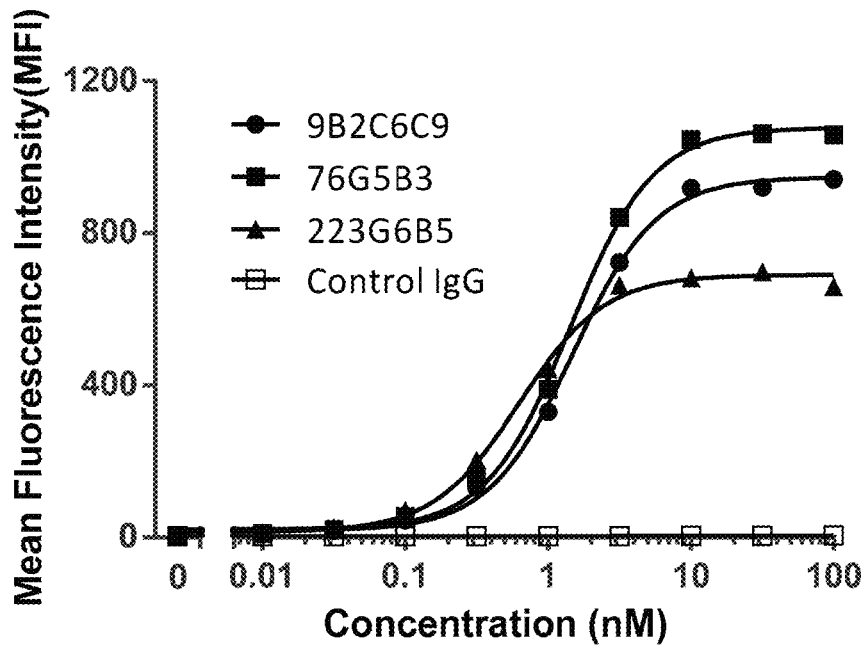
FIGS. 25A&25B show the cell-based binding activity of fully human anti-PD-1 antibodies according to embodiments of the invention to CHO-K1-cPD-1, as measured by flow cytometry.
Figure 25B:
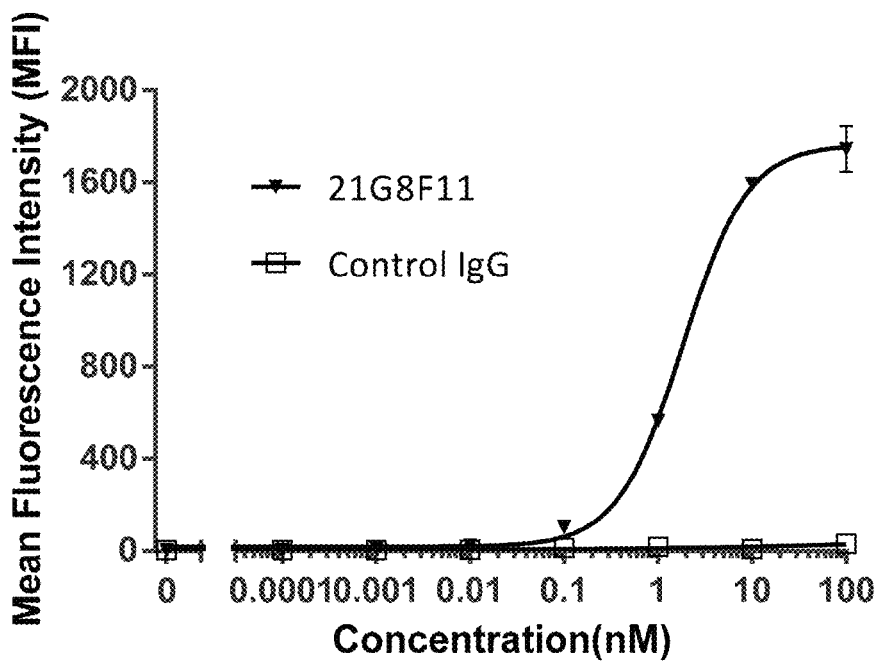
Figure 26:
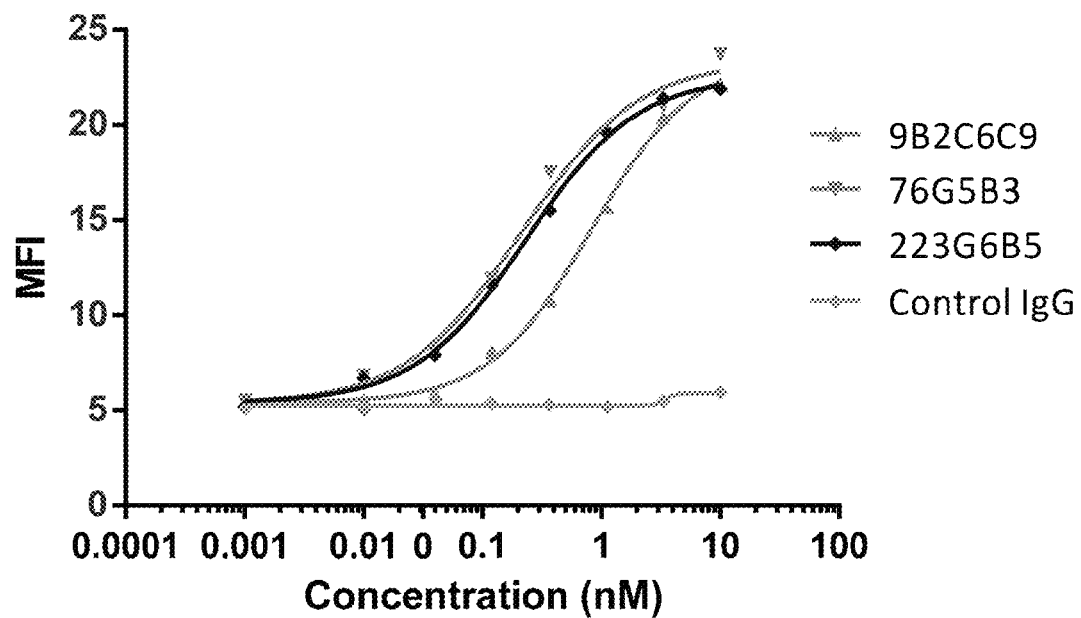
FIG. 26 shows the binding activity of fully human anti-PD-1 antibodies according to embodiments of the invention to activated human PBMCs, as measured by flow cytometry.
Figure 27:
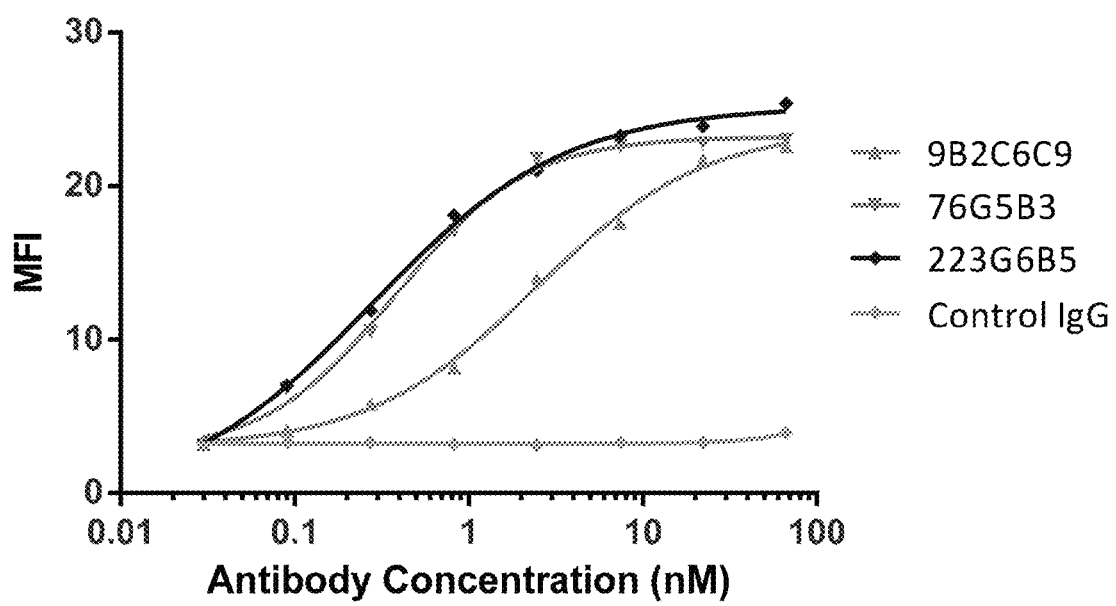
FIG. 27 shows the binding activity of fully human anti-PD-1 antibodies according to embodiments of the invention to activated cyno monkey PBMCs, as measured by flow cytometry.
Figure 28A:
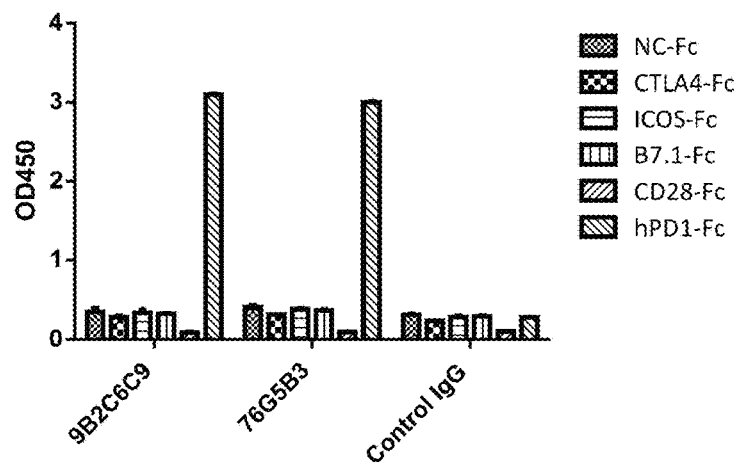
FIGS. 28A-28C show the binding activity of fully human anti-PD-1 antibodies according to embodiments of the invention to other immune checkpoint proteins, as measured by ELISA.
Figure 28B:
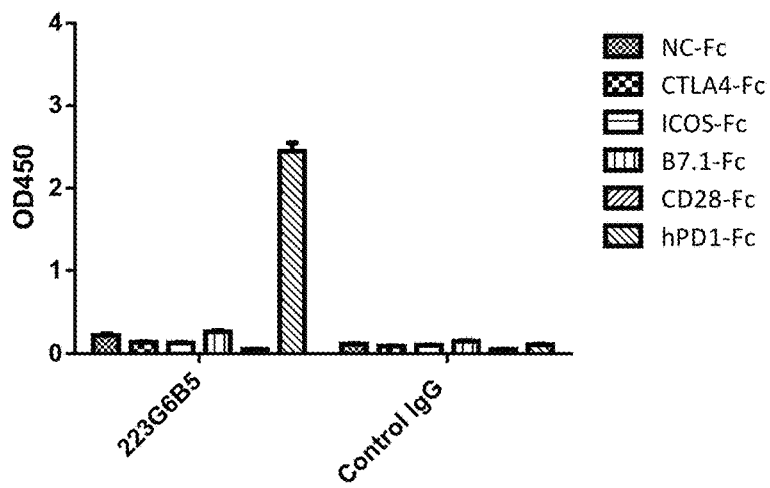
Figure 28C:
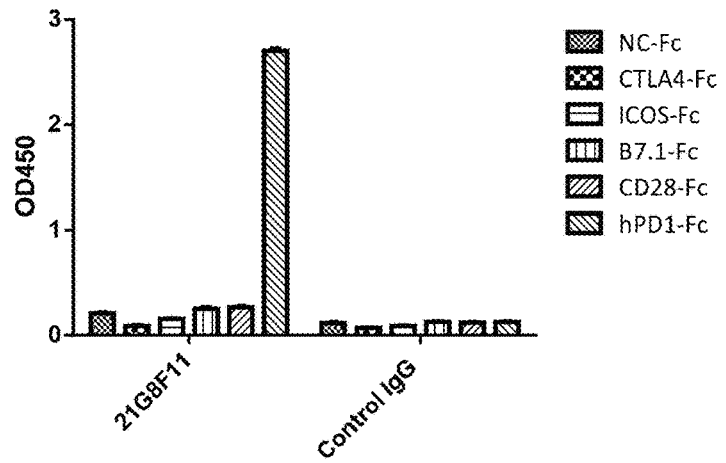
Figure 29A:
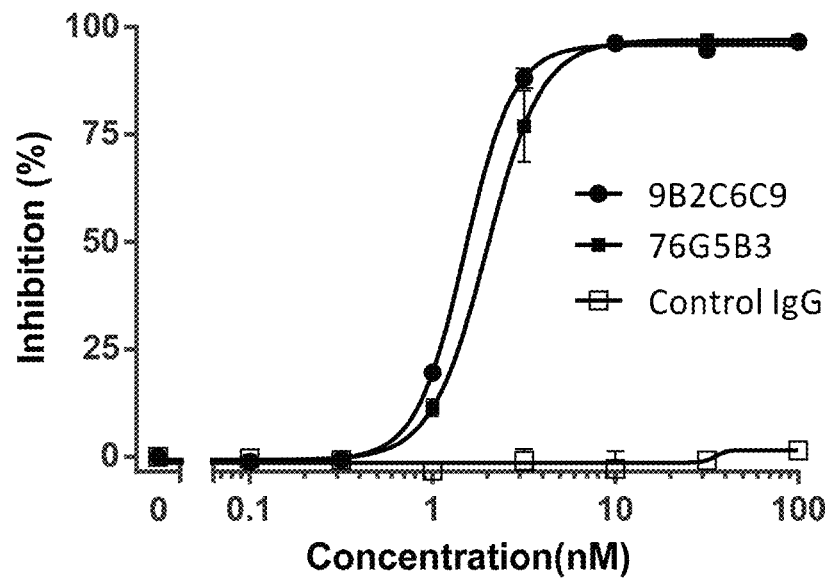
FIGS. 29A&29B show the inhibition of binding of PD-1 protein to its ligand PD-L1 by fully human anti-PD-1 antibodies according to embodiments of the invention, as measured by a protein-based receptor ligand blocking assay.
Figure 29B:
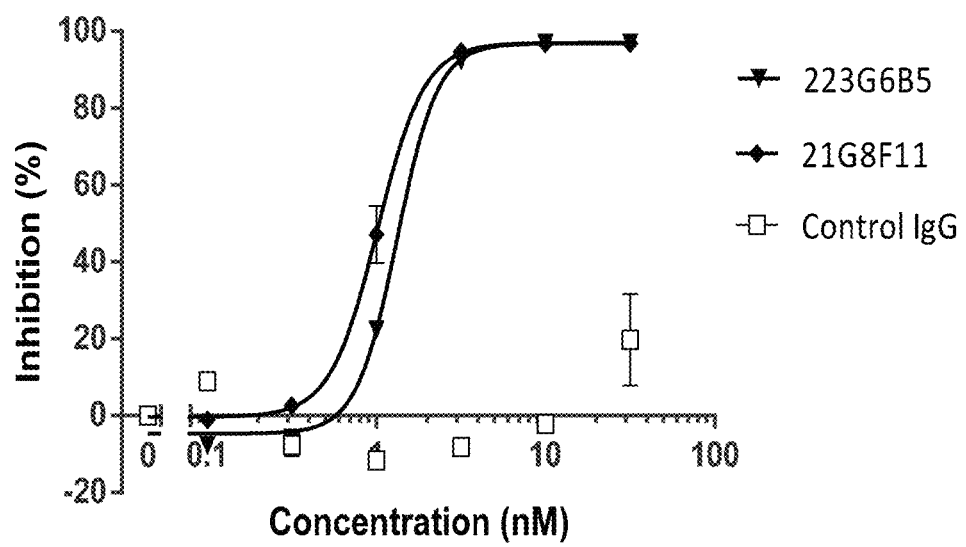
Figure 30A:
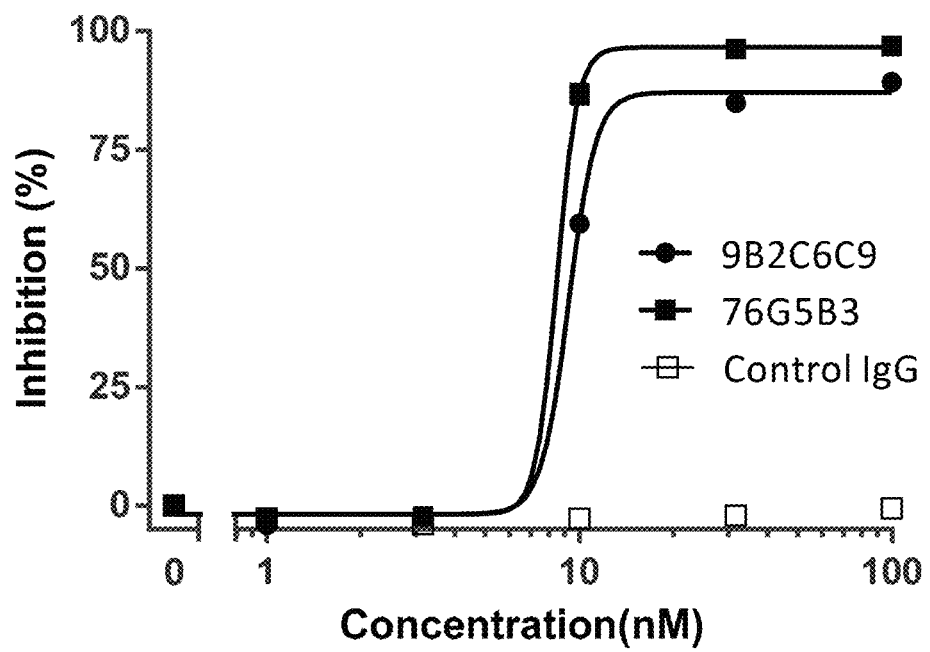
FIGS. 30A&30B show the inhibition of binding of PD-1 protein to its ligand PD-L2 by fully human anti-PD-1 antibodies according to embodiments of the invention, as measured by a protein-based receptor ligand blocking assay.
Figure 30B:
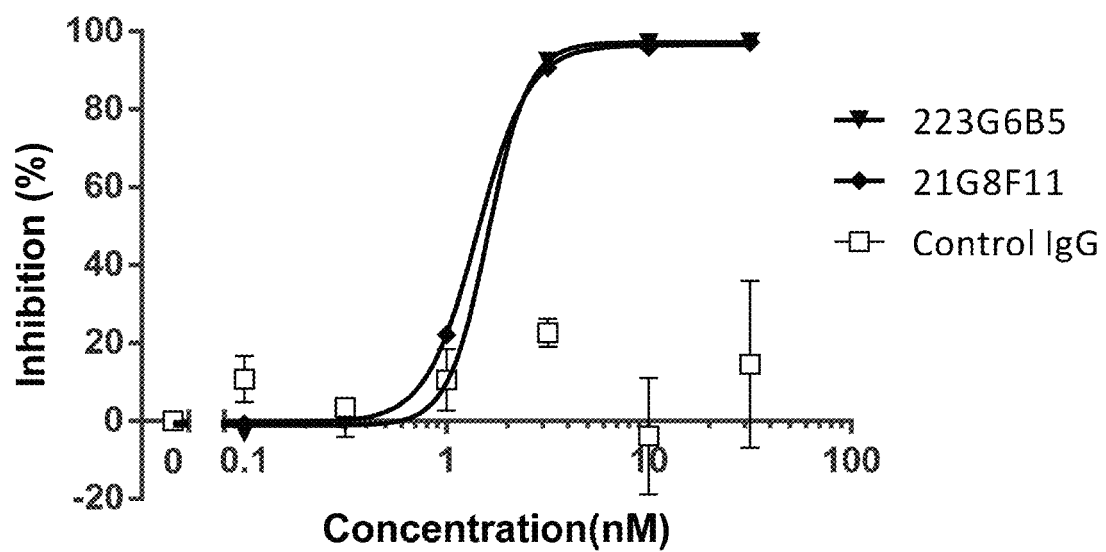
Figure 31A:
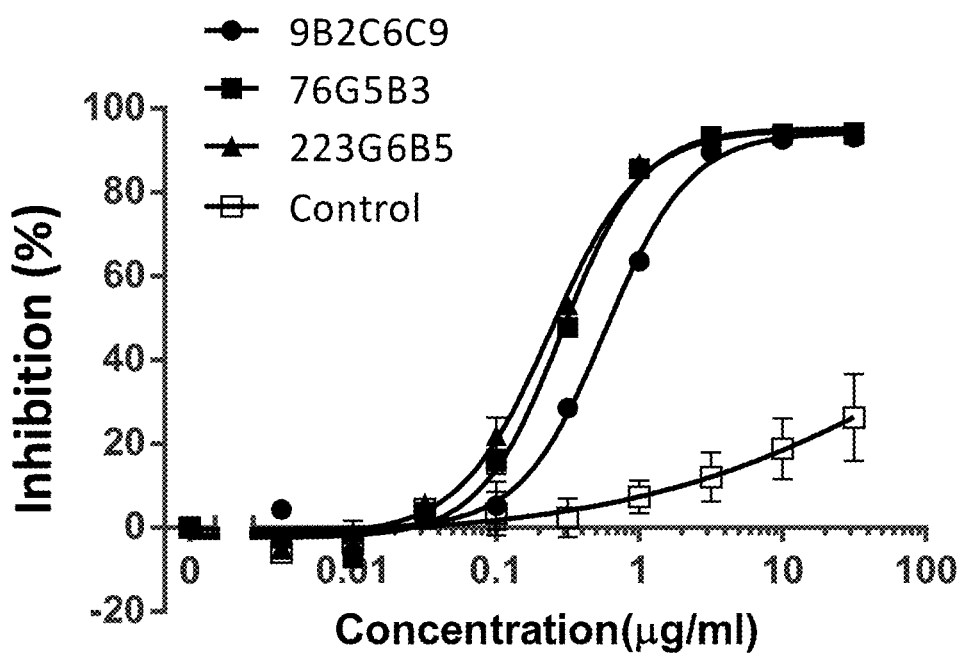
FIGS. 31A&31B show the inhibition of binding of PD-1 protein to its ligand PD-L1 by fully human anti-PD-1 antibodies according to embodiments of the invention, as measured by a cell-based receptor ligand blocking assay.
Figure 31B:
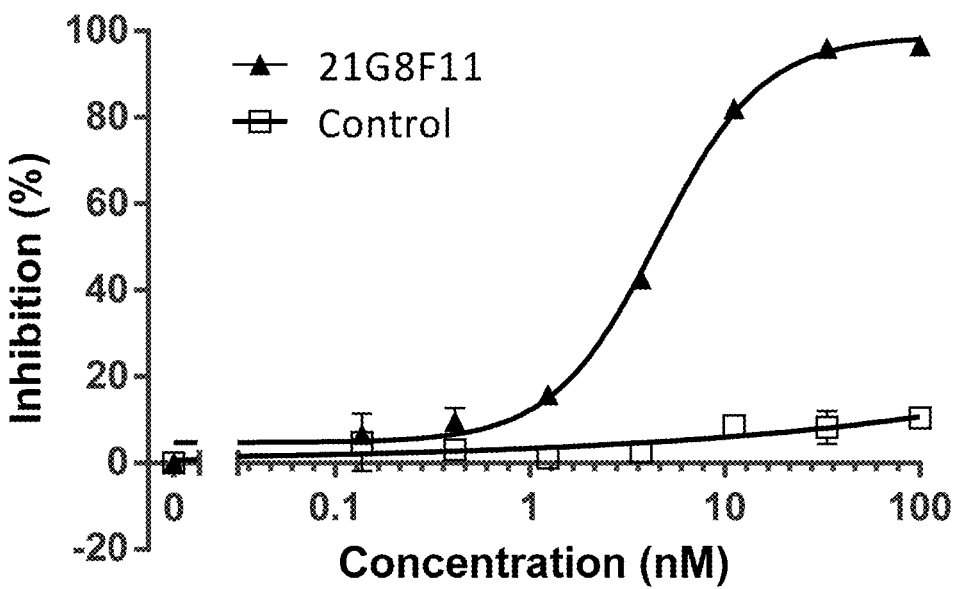
Figure 32A:
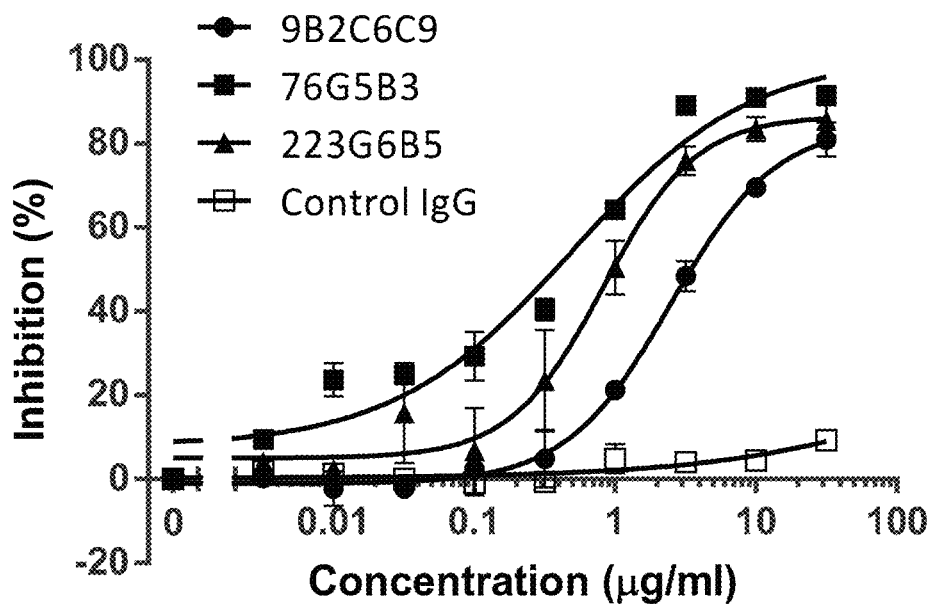
FIGS. 32A&32B show the inhibition of binding of PD-1 protein to its ligand PD-L2 by fully human anti-PD-1 antibodies according to embodiments of the invention, as measured by a cell-based receptor ligand blocking assay.
Figure 32B:
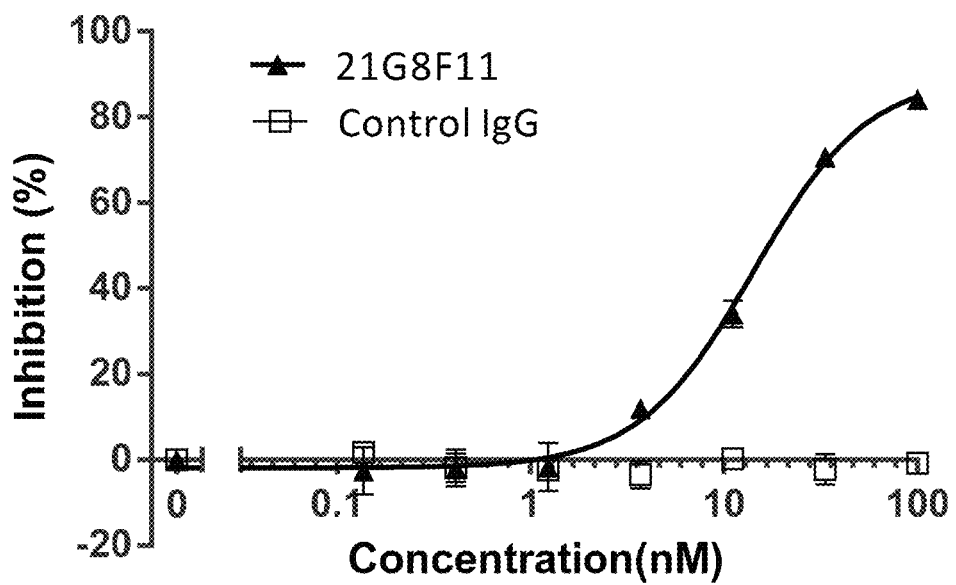
Figure 33:
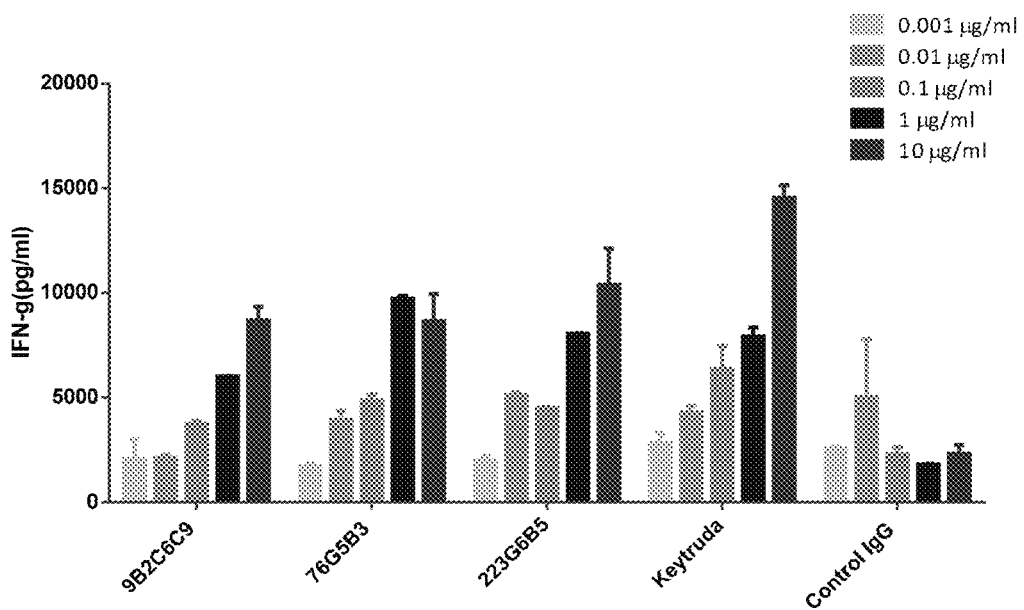
FIG. 33 shows the effect of fully human anti-PD-1 antibodies according to embodiments of the invention on IFN-γ secretion in a T lymphocyte stimulation assay using PBMC's.
Figure 34:
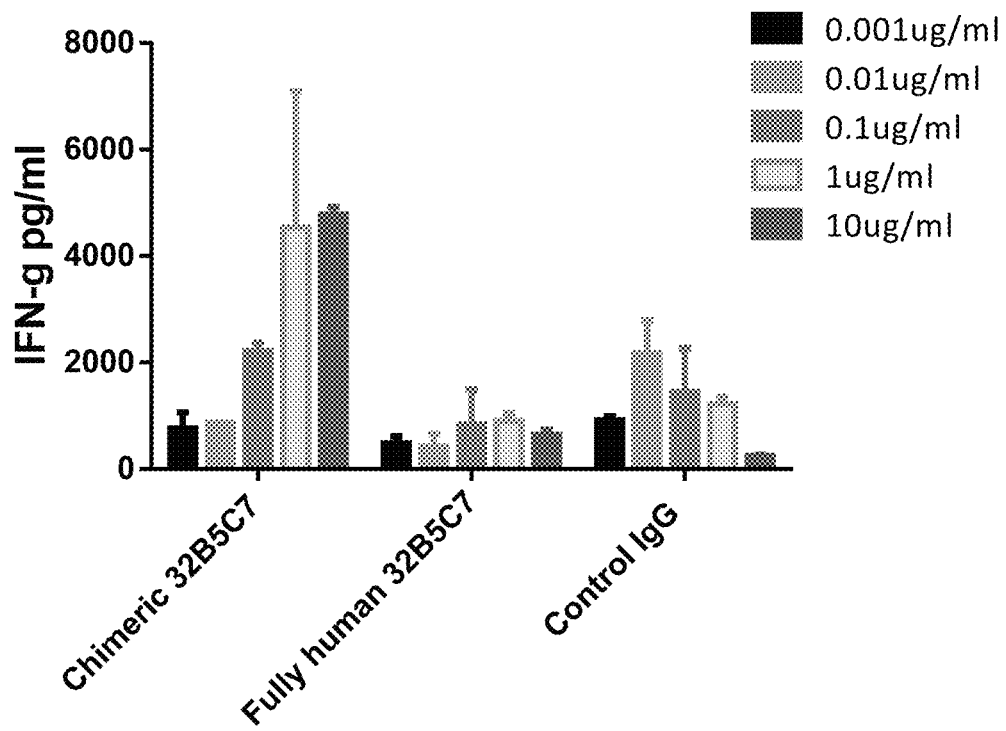
FIG. 34 shows the effect of chimeric and fully human anti-PD-1 antibodies according to embodiments of the invention on IFN-γ secretion in a mixed lymphocyte reaction.
Figure 35:
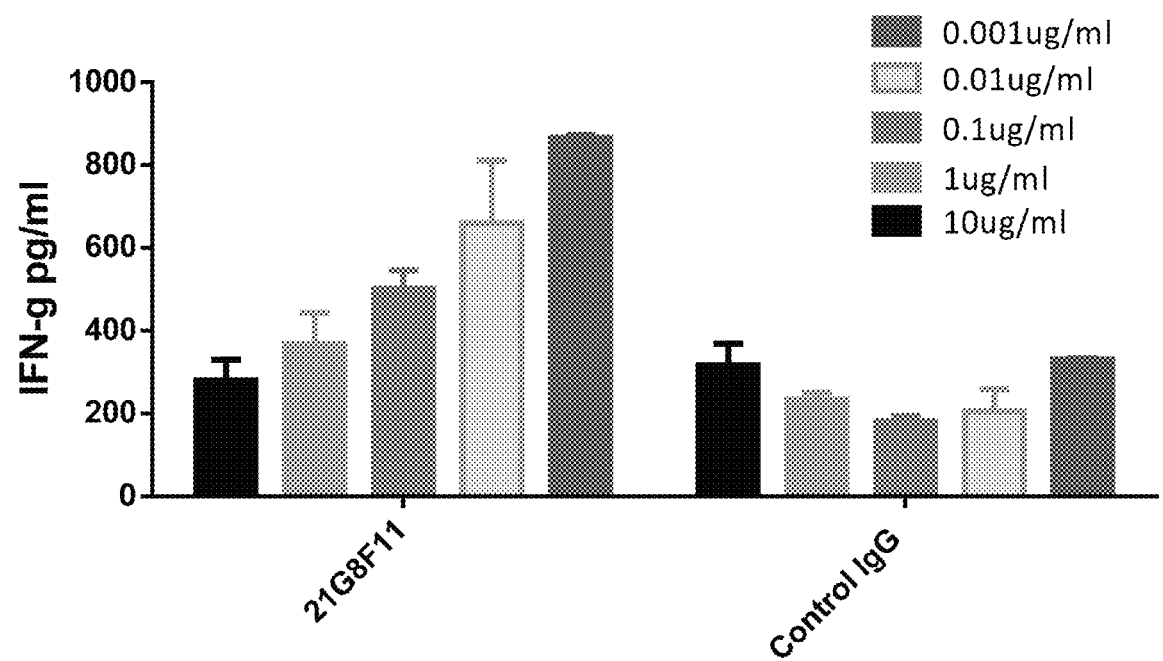
FIG. 35 shows the effect of fully human anti-PD-1 antibodies according to embodiments of the invention on IFN-γ secretion in a T lymphocyte stimulation assay using PBMC's.
Figure 36A:
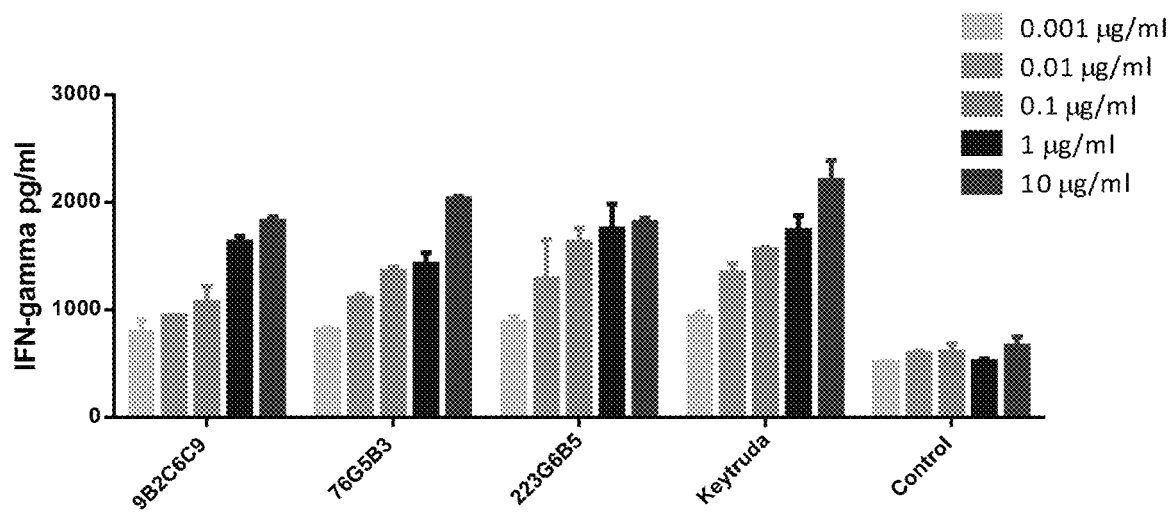
FIGS. 36A&36B shows the effect of fully human anti-PD-1 antibodies according to embodiments of the invention on IFN-γ secretion in a mixed lymphocyte reaction.
Figure 36B:
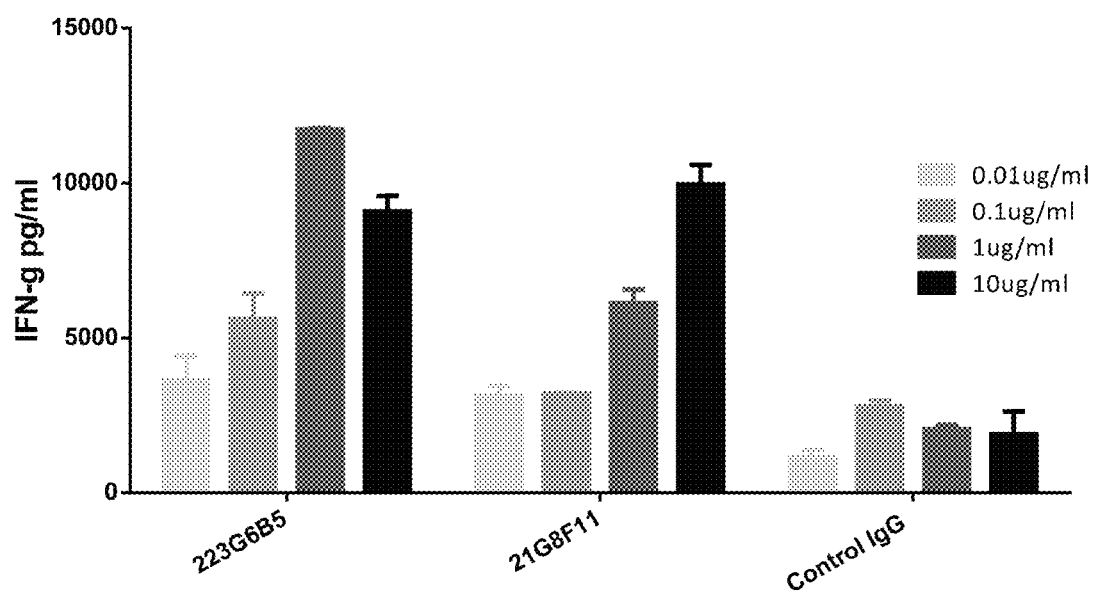

The results for IL-2, shown in FIGS. 14-15 and in Tables 14-15, show that the IL-2 level increased with an increase in anti-PD-1 antibody concentrations. The IgG control is human IgG, and the values listed in Tables 14-15 are the IL-2 concentration (pg/mL) in the culture supernatants. PBMC donor-1 and PBMC donor-2 refer to blood donor ID.

TABLE 14

Chimeric anti-PD-1 mAbs induce IL-2 release, as determined by a mixed lymphocyte reaction assay (PBMC donor-1)

| | IL-2 (pg/mL) Antibody Concentration (µg/mL) | | | | |
|---|---|---|---|---|---|
| Clone ID | 0.001 | 0.01 | 0.1 | 1 | 10 |
| 9B2C6C9 | 82.3 | 96.0 | 144.4 | 142.1 | 151.4 |
| 76G5B3 | 88.8 | 130.7 | 147.7 | 139.7 | 150.1 |
| 223G6B5 | 75.8 | 116.0 | 148.8 | 209.0 | ND |
| 21G8F11 | 33.1 | 48.9 | 106.4 | 65.6 | ND |
| IgG Control | — | — | 76.7 | 76.0 | 83.0 |

TABLE 15

Chimeric anti-PD-1 mAbs induce IL-2 release, as determined by a mixed lymphocyte reaction assay (PBMC donor-2)

| | IL-2 (pg/mL) Antibody Concentration (µg/mL) | | | | |
|---|---|---|---|---|---|
| Clone ID | 0.001 | 0.01 | 0.1 | 1 | 10 |
| 9B2C6C9 | 107.7 | 141.5 | 148.9 | 194.3 | 169.0 |
| 76G5B3 | 93.3 | 145.2 | 182.2 | 193.6 | 188.2 |
| 223G6B5 | 28.7 | 43.7 | 71.1 | 107.0 | ND |
| 21G8F11 | 30.0 | 43.4 | 74.2 | 102.7 | ND |
| IgG Control | — | — | 115.0 | 89.4 | 93.6 |

The results for IFN-γ, shown in FIGS. 16-21 and in Tables 16-19, show that the IFN-γ level increased with an increase in anti-PD-1 antibody concentrations. The IgG control is human IgG, and the values listed in Tables 16-19 are the IFN-γ concentration (pg/mL) in the culture supernatants. PBMC donor-1 and PBMC donor-2 refer to blood donor ID.

TABLE 16

Chimeric PD-1 mAbs induce IFN-γ release, as determined by a mixed lymphocyte reaction assay (PBMC donor-1)

| | IFN-γ (pg/mL) Antibody Concentration (µg/mL) | | | | |
|---|---|---|---|---|---|
| Clone ID | 0.001 | 0.01 | 0.1 | 1 | 10 |
| 9B2C6C9 | 2229.6 | 4687.1 | 17891.3 | 11404.4 | 7591.3 |
| 76G5B3 | 2895.3 | 7526.0 | 12139.7 | 8108.7 | 14490.4 |
| 223G6B5 | 4893.5 | 9376.9 | 27300.3 | 33964.3 | ND |
| 21G8F11 | 3005.3 | 5910.4 | 15299.6 | 15248.1 | ND |
| IgG Control | — | — | 2076.4 | 1720.7 | 2384.1 |

TABLE 17

Chimeric PD-1 mAbs induce IFN-γ release, as determined by a mixed lymphocyte reaction assay (PBMC donor-2)

| | IFN-γ (pg/mL) Antibody Concentration (µg/mL) | | | | |
|---|---|---|---|---|---|
| Clone ID | 0.001 | 0.01 | 0.1 | 1 | 10 |
| 9B2C6C9 | 997.0 | 3496.1 | 7352.7 | 15169.3 | 17565.9 |
| 76G5B3 | 1805.6 | 5518.5 | 12716.3 | 15900.6 | 13348.2 |
| 223G6B5 | 1744.6 | 2573.7 | 4300.4 | 5428.3 | ND |
| 21G8F11 | 2089.3 | 2720.7 | 2626.4 | 2827.1 | ND |
| IgG Control | — | — | 1183.6 | 1871.4 | 2588.0 |

TABLE 18

Chimeric PD-1 mAbs induce IFN-γ release, as determined by a mixed lymphocyte reaction assay (PBMC donor-1)

| | IFN-γ (pg/mL) Antibody Concentration (µg/mL) | | | | |
|---|---|---|---|---|---|
| Clone ID | 0.001 | 0.01 | 0.1 | 1 | 10 |
| 32B5C7 | 339.95 | 4719.75 | 6197.8 | 10864.95 | 21250.1 |
| IgG Control | — | 1458.32 | 1446.08 | 1251.255 | — |

TABLE 19

Chimeric PD-1 mAbs induce IFN-γ release, as determined by a mixed lymphocyte reaction assay (PBMC donor-2)

| | IFN-γ (pg/mL) Antibody Concentration (µg/mL) | | | |
|---|---|---|---|---|
| Clone ID | 0.01 | 0.1 | 1 | 10 |
| 32B5C7 | 11865.3 | 26675.9 | 32325.9 | 46764.8 |
| IgG Control | 352.8 | 281.3 | 127.1 | — |

Example 6—Determination of the Amino Acid Sequences in the Variable Regions of the Anti-PD-1 Antibodies Total RNA isolation: After the supernatants from the hybridoma subclones obtained from Example 2 were characterized (i.e., validation and determination of bioactivity, Examples 3-5), 5×10$^7$ hybridoma cells were collected by centrifugation. 1 mL Trizol was added to the cell pellets, mixed and transferred to 1.5 mL centrifuge tubes, and incubated at room temperature for 5 minutes. 0.2 mL chloroform were added to the samples and vortexed for 15 seconds. After standing for 2 minutes, the mixtures were centrifuged at 12000 g at 4° C. for 5 minutes. The supernatants were collected and transferred to new 1.5 mL centrifuge tubes, 0.5 mL isopropyl alcohol was added and mixed gently, and the samples were incubated at room temperature for 10 minutes. The samples were centrifuged at 12000 g at 4° C. for 15 minutes. The supernatants were aspirated, and the precipitates were washed with 1 mL 75% (v/v) ethanol. The mixtures were centrifuged at 12000 g at 4° C. for 5 minutes, the supernatants were decanted, and the precipitates were air-dried. Total RNA was obtained by adding DEPC-treated water to the precipitates (55° C. water bath for 10 minutes).

Reverse transcription and PCR: 1 ug of RNA and reverse transcriptase were added to a reaction mixture of a final volume of 20 uL, and the mixture was incubated at 42° C. for 60 minutes and then at 70° C. for 10 minutes to terminate the reaction. A 50 uL PCR reaction mixture was prepared, containing 1 uL cDNA, 25 pmol of each primer, 1 uL DNA polymerase, 250 umol dNTPs, and the buffer system. The PCR program settings were as follows: denaturation at 95° C. for 3 minutes, 35 cycles of denaturation (95° C. for 30 seconds), annealing (55° C. for 30 seconds) and elongation (72° C. for 35 seconds), followed by a final extension at 72° C. for 5 minutes to obtain the PCR product. The commercially available reverse transcription kit used was PrimeScript RT Master Mix (Takara, RR036), and the commercially available Q5 ultra-fidelity polymerase PCR kit was from NEB (M0492).

Cloning and sequencing: 5 uL PCR products were examined by agarose gel electrophoresis, and the samples were recovered from the agarose gel using NucleoSpin Gel & PCR Clean-up kit (MACHEREY-NAGEL, 740609). Ligation reaction: To a 50 ng sample, 50 ng T vector, 0.5 uL ligase, and 1 uL buffer were added and brought to a final volume of 10 uL with water. The reaction mixture was incubated at 16° C. for 30 minutes using the T4 DNA Ligase (NEB, M0402). 5 uL ligation product was added to 100 uL competent cells (Ecos 101 competent cells, Yeastern, FYE607), which were incubated on ice for 5 minutes, heat shocked at 42° C. for 1 minute and incubated on ice again for 1 minute. Cells were recovered by adding 650 uL SOC medium without antibiotics and incubating at 37° C. in a shaking incubator for 30 minutes at 200 rpm. 200 uL of each bacterial culture was spread onto an LB agar plate containing antibiotics at 37° C. overnight. The next day, PCR reactions were set up using the T vector primers M13F and M13R. Pipette tips were used to pick bacterial colonies and were dipped into PCR reaction mixture and pipetted up and down. Half of the reaction mixture was transferred to an LB agar plate containing 100 nM ampicillin. After the PCR reactions, 5 uL of the PCR products were removed and examined by agarose gel electrophoresis, and positive samples were sent for sequencing and analysis (Kabat, 1991, "Sequences of proteins of objective interest," the NIH, Bethesda, Md.). The sequencing results are shown in Tables 1-2.

Example 7—Conversion, Expression and Purification of Fully Human Anti-PD-1 Antibody (step 1) Plasmid construction and preparation: Sequences of the anti-PD-1 antibody heavy and light chain variable regions were obtained according to Example 6. The anti-PD-1 antibodies' heavy chain variable region sequences were subcloned into expression vectors containing a signal peptide and a human heavy chain IgG4 constant region with a S228P mutation. The anti-PD-1 antibodies' light chain variable region sequences were subcloned into expression vectors containing a signal peptide and a human antibody light chain kappa constant region. The recombinant plasmids were verified and confirmed by sequencing (the sequencing method was the same as in Example 6). Alkaline lysis was performed using a reagent kit (MACHEREY-NAGEL) to improve the purity and quality of the recombinant plasmids, and the plasmids were filtered through 0.22 uM filters (Millpore). The purified plasmids were used for transfection.

(step 2) Transfection: HEK293E cells (Invitrogen) were cultured in FreeStyle 293 medium (Invitrogen) at 37° C., 130 RPM, 8% $CO_2$ (v/v). HEK293E cells were adjusted to $1$-$1.5 \times 10^6$/mL cell density for transfection. 10% (v/v) F68 (Invitrogen) was added to the FreeStyle 293 medium to a final concentration of 0.1% (v/v), as Medium A. 5 mL of Medium A and 200 ug/mL PEI (Sigma) were mixed to generate Medium B. 5 mL of Medium A and 100 ug/mL recombinant plasmid from step 1 were mixed to generate Medium C. After 5 minutes of incubation, Medium B and Medium C were mixed and incubated for 15 minutes to generate Mixture D. 10 mL of Mixture D were slowly added to 100 mL HEK293E cells with continuous stirring to avoid local accumulation of PEI. HEK293E cells were incubated overnight while shaking. The next day, peptone was added to a final concentration of 0.5% (w/v). On about day 5-7, the antibodies' titers were determined. On about day 6-7, the HEK293E cultures were centrifuged (30 minutes, 3500 RPM), and the supernatants were collected and filtered through 0.22 uM filters for purification.

(step 3) Antibody purification: Protein A columns (GE) were washed with 0.1M NaOH for 30 minutes or with 5 bed volumes of 0.5M NaOH to get rid of endotoxin. Columns that had not been used in a longtime were soaked in 1M NaOH for at least 1 hour, washed with endotoxin-free water to a neutral pH, and washed with 10 bed volumes of 1% Triton X100. The columns were then equilibrated with 5 bed volumes of PBS (PBS phosphate buffer, pH7.2). The filtered supernatants from step 2 were loaded onto the columns, and the flow through was collected, if necessary. The columns were washed with 5 bed volume of PBS and then eluted with 5 bed volumes of 0.1M Glycine-HCl pH3.0. The eluates containing anti-PD-1 antibodies were neutralized with 0.5 bed volumes of 1M Tris-HCl (NaCl 1.5M) pH8.5. The human anti-PD-1 antibodies were dialyzed in 1×PBS for 4 hours, to avoid endotoxin contamination. After dialysis, the anti-PD-1 antibody concentrations were determined by spectrophotometry or a reagent kit, the purities of the antibodies were determined by HPLC-SEC, and the contents of endotoxin were determined by an endotoxin test kit (Lonza). The fully human anti-PD-1 antibodies were characterized, and the results are shown in FIGS. 22-41, and in Tables 20-25.

TABLE 20

Binding activities of fully human anti-PD-1 mAbs to human PD-1$^{ECD}$-hFc, as measured by ELISA

| | $OD_{450\,nm}$ Antibody concentration (nM) | | | | | | | | |
|---|---|---|---|---|---|---|---|---|---|
| Clone ID | 100 | 10 | 1 | 0.1 | 0.01 | 0.001 | 0.0001 | 0.00001 | 0 |
| 9B2C6C9 | 2.60 | 2.55 | 2.51 | 1.56 | 0.34 | 0.12 | 0.10 | 0.10 | 0.09 |
| 76G5B3 | 2.58 | 2.44 | 2.47 | 1.34 | 0.28 | 0.12 | 0.10 | 0.10 | 0.09 |
| 32B5C7 | N/A | N/A | N/A | N/A | N/A | N/A | N/A | N/A | N/A |
| 223G6B5 | 2.78 | 2.80 | 2.86 | 2.38 | 0.62 | 0.32 | 0.29 | N/A | 0.30 |
| 21G8F11 | 3.03 | 3.02 | 3.03 | 2.62 | 0.58 | 0.26 | 0.16 | N/A | 0.18 |
| IgG control | 0.34 | 0.26 | 0.25 | 0.24 | 0.23 | 0.24 | 0.25 | N/A | 0.28 |

TABLE 21

Binding activities of fully human anti-PD-1 mAbs to Cyno Monkey PD-1$^{ECD}$-hFc, as measured by ELISA

| | OD$_{450\ nm}$ Antibody concentration (nM) | | | | | | | | |
|---|---|---|---|---|---|---|---|---|---|
| Clone ID | 100 | 10 | 1 | 0.1 | 0.01 | 0.001 | 0.0001 | 0.00001 | 0 |
| 9B2C6C9 | 2.43 | 2.38 | 2.11 | 0.73 | 0.14 | 0.07 | 0.07 | 0.07 | 0.06 |
| 76G5B3 | 2.45 | 2.41 | 2.32 | 1.06 | 0.20 | 0.08 | 0.06 | 0.06 | 0.06 |
| 32B5C7 | N/A | N/A | N/A | N/A | N/A | N/A | N/A | N/A | N/A |
| 223G6B5 | 2.85 | 2.87 | 2.88 | 2.50 | 0.83 | 0.33 | 0.29 | N/A | 0.31 |
| 21G8F11 | 3.00 | 3.02 | 2.99 | 2.39 | 0.51 | 0.22 | 0.15 | N/A | 0.19 |
| IgG control | 0.33 | 0.28 | 0.27 | 0.26 | 0.27 | 0.26 | 0.27 | N/A | 0.31 |

TABLE 22

Binding activities of fully human anti-PD-1 mAbs to other immune checkpoint proteins, as measured by ELISA

| | OD$_{450\ nm}$ Immune check point proteins | | | | | |
|---|---|---|---|---|---|---|
| Clone ID | hPD 1 | CD28 | B7.1 | ICOS | CTLA4 | NC-Fc |
| 9B2C6C9 | 3.10 | 0.09 | 0.33 | 0.34 | 0.28 | 0.35 |
| 76G5B3 | 3.01 | 0.10 | 0.37 | 0.38 | 0.32 | 0.41 |
| 32B5C7 | N/A | N/A | N/A | N/A | N/A | N/A |
| 223G6B5 | 1.85 | 0.05 | 0.25 | 0.12 | 0.13 | 0.20 |
| 21G8F11 | 2.70 | 0.27 | 0.25 | 0.16 | 0.09 | 0.21 |
| IgG control | 0.28 | 0.10 | 0.29 | 0.28 | 0.23 | 0.31 |

TABLE 23

Binding activities of fully human anti-PD-1 mAbs to CHO-K1-hPD-1, as determined by FACS

| | Mean fluorescence intensity Antibody concentration (nM) | | | | | | | | | |
|---|---|---|---|---|---|---|---|---|---|---|
| Clone ID | 100.0 | 31.6 | 10.0 | 3.2 | 1.0 | 0.32 | 0.10 | 0.03 | 0.01 | 0 |
| 9B2C6C9 | 1574 | 1646 | 1668 | 1519 | 830 | 324.0 | 108.0 | 38.7 | 16.1 | 4.2 |
| 76G5B3 | 1884 | 1943 | 1920 | 1881 | 1200 | 504.9 | 167.5 | 58.9 | 22.9 | 4.1 |
| 223G6B5 | 1404 | 1413 | 1434 | 1421 | 1114 | 501.3 | 168.1 | 58.4 | 22.3 | 4.0 |
| IgG control | 6.0 | 4.8 | 4.4 | 4.2 | 4.0 | 4.0 | 3.9 | 4.0 | 4.0 | 3.9 |

| | Mean fluorescence intensity Antibody concentration (nM) | | | | | | | |
|---|---|---|---|---|---|---|---|---|
| Clone ID | 100 | 10 | 1 | 0.1 | 0.01 | 0.001 | 0.0001 | 0 |
| 21G8F11 | 1729 | 1794 | 1794 | 1700 | 1015 | 414.5 | 137.7 | 48.8 |
| IgG control | 705.2 | 708.7 | 719.0 | 712.6 | 559.0 | 252.6 | 86.0 | 31.2 |

| | Mean fluorescence intensity Antibody concentration (nM) | | | | | | |
|---|---|---|---|---|---|---|---|
| Clone ID | 66.7 | 6.7 | 0.7 | 0.07 | 0.01 | 0.0007 | 0.00 |
| 32B5C7 | 479.9 | 252.1 | 53.6 | 9.0 | 2.8 | 2.6 | 2.4 |

TABLE 24

Binding activities of fully human anti-PD-1 mAbs to CHO-K1-cPD-1, as determined by FACS

| | Mean fluorescence intensity Antibody concentration (nM) | | | | | | | | | |
|---|---|---|---|---|---|---|---|---|---|---|
| Clone ID | 100.0 | 31.6 | 10.0 | 3.2 | 1.0 | 0.3 | 0.1 | 0.03 | 0.01 | 0.0 |
| 9B2C6C9 | 5.0 | 4.4 | 4.2 | 3.9 | 3.9 | 3.9 | 3.9 | 3.9 | 3.9 | 4.0 |
| 76G5B3 | 100.0 | 31.6 | 10.0 | 3.2 | 1.0 | 0.3 | 0.1 | 0.0 | 0.0 | 0.0 |

TABLE 24-continued

Binding activities of fully humananti-PD-1 mAbs to CHO-K1-cPD-1, as determined by FACS

| 223G6B5 | 859.0 | 879.8 | 864.6 | 752.9 | 416.8 | 181.3 | 63.5 | 24.4 | 11.2 | 3.8 |
| --- | --- | --- | --- | --- | --- | --- | --- | --- | --- | --- |
| IgG control | 5.0 | 4.4 | 4.2 | 4.0 | 4.0 | 4.0 | 3.9 | 3.9 | 3.9 | 3.9 |

| | Mean fluorescence intensity Antibody concentration (nM) | | | | | | | |
| --- | --- | --- | --- | --- | --- | --- | --- | --- |
| Clone ID | 100 | 10 | 1 | 0.1 | 0.01 | 0.001 | 0.0001 | 0 |
| 21G8F11 | 1744.7 | 1593.2 | 566.6 | 104.2 | 24.0 | 10.9 | 5.5 | 3.7 |
| IgG control | 33.1 | 8.7 | 19.6 | 13.8 | 5.3 | 3.9 | 3.8 | 3.7 |

TABLE 25

Binding kinetics and affinities of fully human anti-PD-1 mAbs to His-tagged human PD-1 ECD protein, as determined by Biacore

| Clone ID | $K_D$ (M) | $k_a$ (1/Ms) | $k_d$ (1/s) |
| --- | --- | --- | --- |
| 9B2C6C9 | 7.209E-9 | 1.674E+4 | 1.207E-4 |
| 76G5B3 | 9.357E-10 | 9.996E+4 | 9.354E-5 |
| 223G6B5 | 5.496E-9 | 8.650E+4 | 4.754E-4 |
| pembrolizumab | 8.02E-9 | 3.35E+5 | 2.69E-3 |
| nivolumab | 1.08E-8 | 1.30E+5 | 1.40E-3 |

Example 8—Determination of Binding and Dissociation Constants by Biacore

Anti-human Fc IgG was immobilized on flow cells 1 and 2: HBS-EP+ (10 mM HEPES, 150 mM NaCl, 3 mM EDTA, 0.05% P20, pH 7.4) was used as running buffer, and the immobilization of anti-human Fc IgG was carried out using the immobilization wizard template. Flow cells 1 and 2 of a Series S CM5 sensor chip were activated with freshly-mixed 50 mmol/L NHS and 200 mmol/L EDC. 20 ug/mL of anti-human Fc IgG diluted in 10 mM NaAC (pH 4.5) was injected into the activated flow cells 1 and 2. The remaining active coupling sites were blocked with 1M ethanolamine.

Recombinant His-tagged hPD-1 ECD protein was diluted to 50 nM, followed by four 2-fold serial dilutions with HBS-EP+ buffer. The His-tagged hPD-1 ECD protein concentrations were 0 nM, 3.125 nM, 6.25 nM, 12.5 nM, 25 nM and 50 nM. $K_D$ measurements were carried out with HBS-EP+ as the running buffer. Each antibody was injected over the CM5 sensor flow cell 2 with a flow rate of 10 uL/min to reach response 230 RU. Prepared His-tagged hPD-1 ECD protein was then injected over flow cells 1 and 2, at a flow rate of 30 uL/min for 180 sec. Buffer flow was maintained for 400 seconds for dissociation measurements (30 uL/min). To remove the tested antibody from the surface, 10 mM glycine-HCl pH 1.5 was injected for 20 seconds (30 uL/min). Flow cell 1 was used as reference flow cell. The above steps were repeated for each concentration of serially-diluted His-tagged PD-1$^{ECD}$ protein. The $K_D$ value for each antibody was evaluated using Biacore T200 evaluation software 1.0, and the data was fit with a 1:1 binding model. The results are shown in Table 25.

Example 9—ADCC and CDC Effector Function Analysis

To confirm the presumed absence of effector function of fully human anti-PD-1 antibodies, antibody-dependent cell-mediated cytotoxicity (ADCC) and complement-dependent cytotoxicity (CDC) assays were performed.

Figure 37:
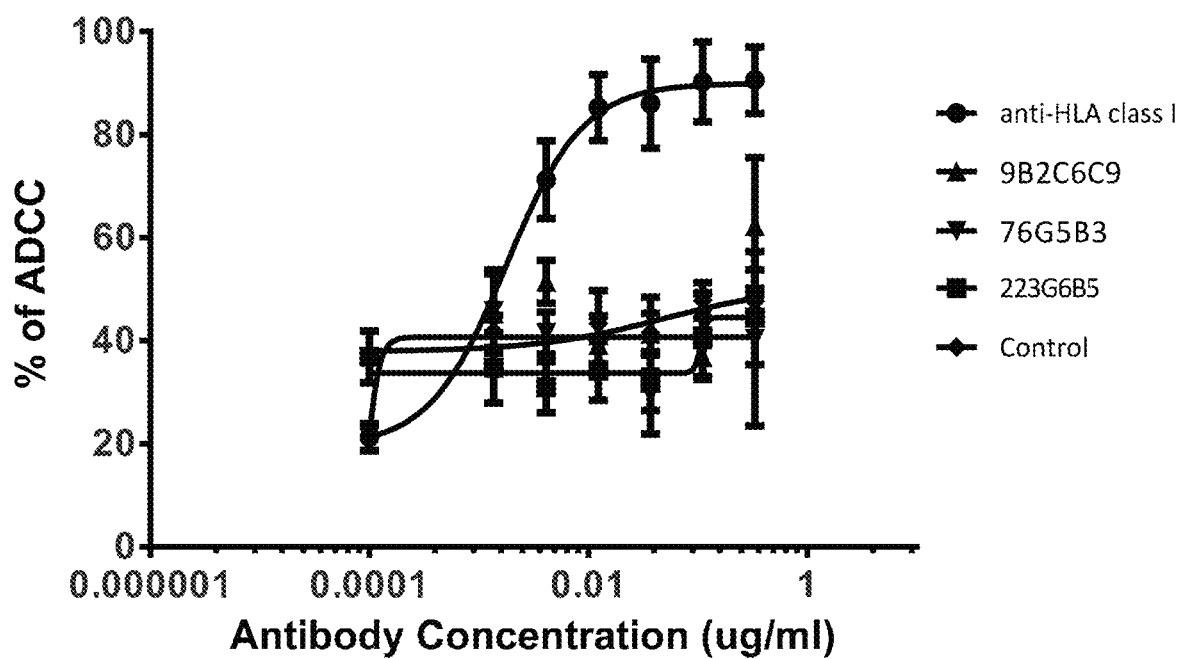
FIG. 37 shows the effect of fully human anti-PD-1 antibodies according to embodiments of the invention on Antibody-Dependent Cellular Cytotoxicity (ADCC)

For the ADCC assay, samples of PD-1-expressing Jurkat T cells were adjusted to a concentration of 12.5×10$^4$ cells/mL with ADCC medium (without phenol red). 40 uL of cell suspensions (1×10$^4$ viable cells) were added to each well of a v-bottom 96-well plate. 20 uL of antibody were serially diluted in ADCC medium (without phenol red) and added to each well in triplicate. The final antibody concentrations were: 1.4 ng/mL, 4.1 ng/mL, 12.3 ng/mL, 0.037 ug/mL, 0.111 ug/mL, 0.333 ug/mL, and 1 ug/mL. The plate was incubated at 22-25° C. for 30 minutes. NK92 cells stably transfected with FcγRIII 158V were adjusted with ADCC medium (without phenol red) so that by adding 40 uL of NK92 cells stably transfected with FcγRIII 158V to the target cells, the ratio of effector to target cells was 1:1. The plate was then incubated at 37° C. for 4 hours. After 4 hours incubation, 100 uL substrate from CytoTox 96 kit (Promega) were added to each well. For maximum cell lysis control, 2 uL of lysis solution (CytoTox-ONE™ kit, Promega) was added 10 minutes before the addition of 100 uL substrate from CytoTox 96 kit. The plate was incubated at room temperature for 10 minutes, and 50 uL of stop solution were then added to each well and mixed for 30 seconds. The absorbance at 560/590 nm was measured, and the 1% lysis values were calculated using GraphPad Prism 5.0. The results, shown in FIG. 37, show that the anti-HLA antibody induced ADCC in PD-1-expressing JurkatT cell cells, but the fully human anti-PD-1 antibodies had no ADCC effect on PD-1-expressing Jurkat T cells.

Figure 38:
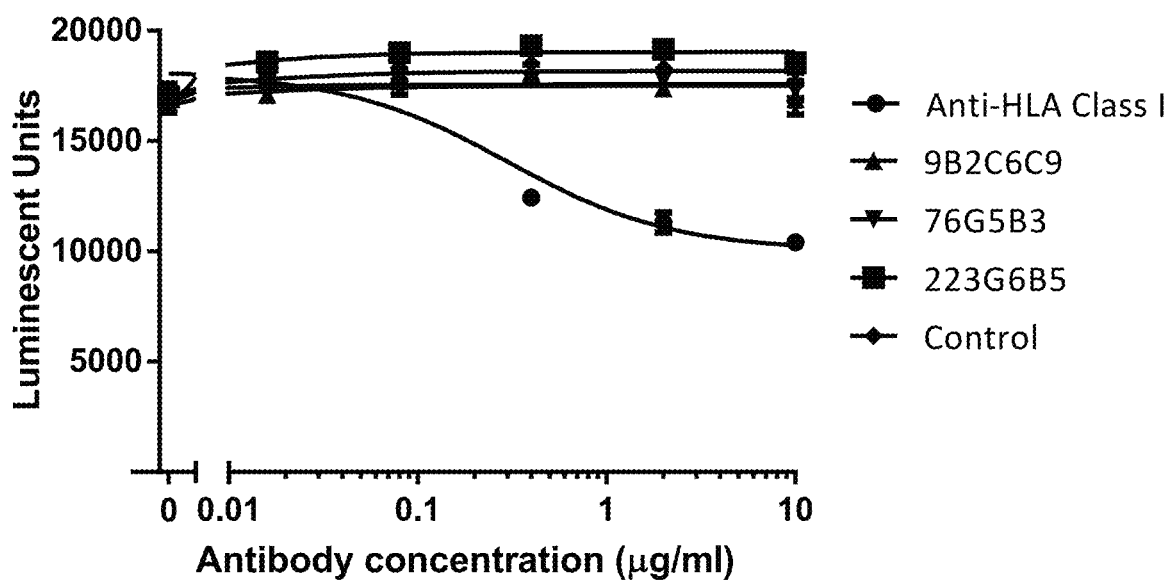
FIG. 38 shows the effect of fully human anti-PD-1 antibodies according to embodiments of the invention on Complement-Dependent Cytotoxicity.

For the CDC assay, PBMCs were harvested and CD4+ T cells were isolated using a CD4+ T cell isolation kit (Stemcell, No. 19052). CD4+ cells were incubated with anti-CD3 antibody (Clone: OKT3) for 48 hours to induce expression of PD-1. Cells were harvested, and the cell concentrations were adjusted to 1.25×10$^6$ cells/mL with cell culture medium. To a flat-bottom 96-well white plate, 40 uL/well of cells were added. 40 uL/well of fully human anti-PD-1 antibody, serially diluted in CDC medium, were added to each well in duplicate. The final antibody concentrations were: 0 ng/mL, 16 ng/mL, 80 ng/mL, 0.4 ug/mL, 2 ug/mL, and 10 ug/mL. The plates were incubated in the hood for 30 minutes. Commercially available purified human complement (Quidel, cat #042637) was added to the plates containing cells at 20 uL/well to a final concentration of 20%. The plates were incubated at 37° C. for 20 hours. The Celltiter-glo luminescent cell viability kit (Promega, No. G7573) was used to test cell viability according to the manufacture-provided protocol. The plates were shaken on a microplate shaker for 2 minutes at a speed of 200 and then incubated at room temperature for 10 minutes. The luminescence signal was read with Envision. For data analysis, the % cytotoxicity was calculated using GraphPad Prism 5.0. The results, shown in FIG. 38, show that the anti-HLA antibody induced CDC in activated CD4+ T cells, but the fully human anti-PD-1 antibodies had no CDC effect on activated CD4+ T cells.

Example 10—Antibody Thermostability, Measured by Differential Scanning Calorimetry (DSC)

Figure 39:
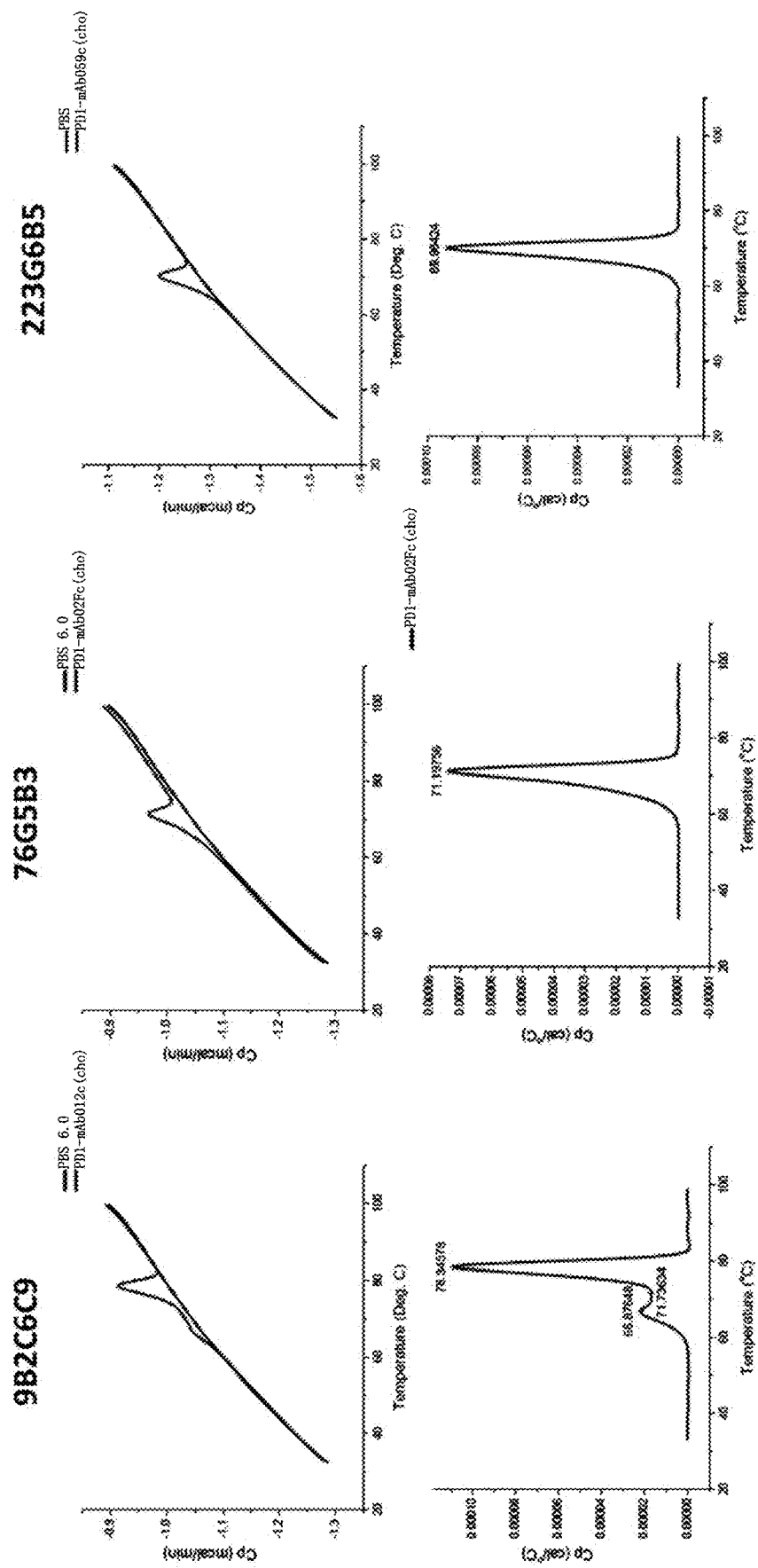
FIG. 39 shows the thermostability of fully human anti-PD-1 antibodies according to embodiments of the invention, as measured by Differential Scanning calorimetry (DSC)
Figure 40:
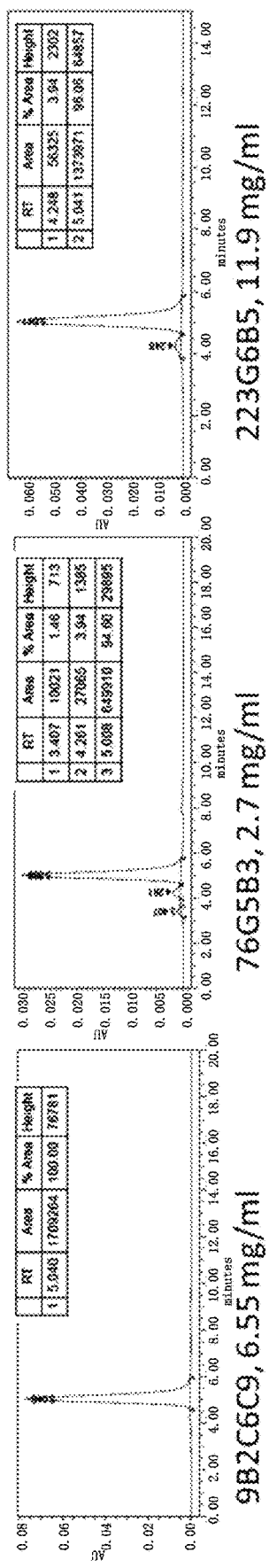
FIG. 40 shows the freeze/thaw stability of fully human anti-PD-1 antibodies according to embodiments of the invention.
Figure 40:
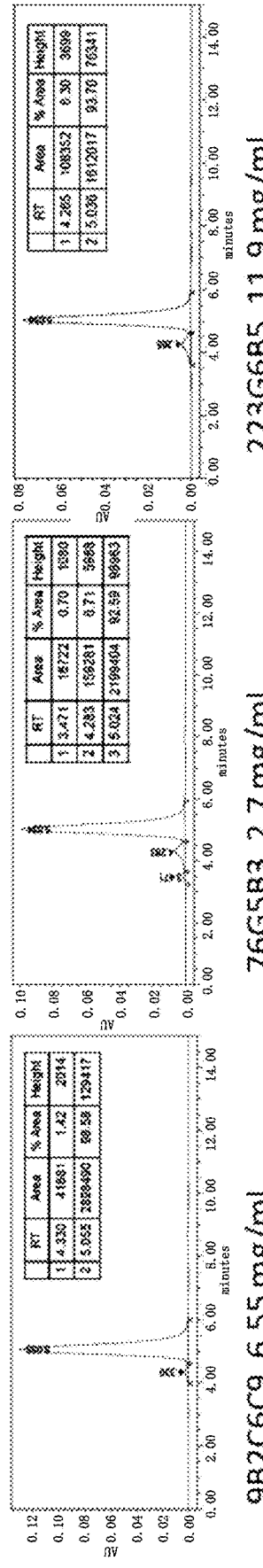
Figure 40:
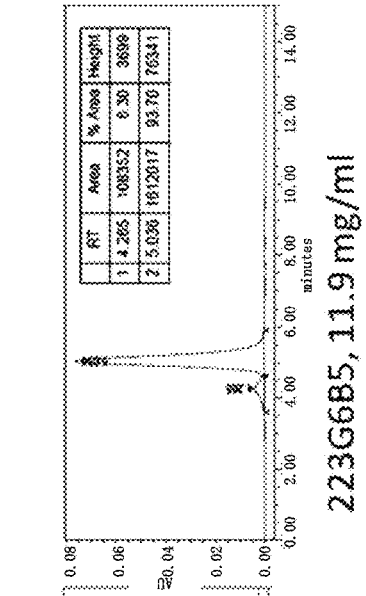
Figure 41:
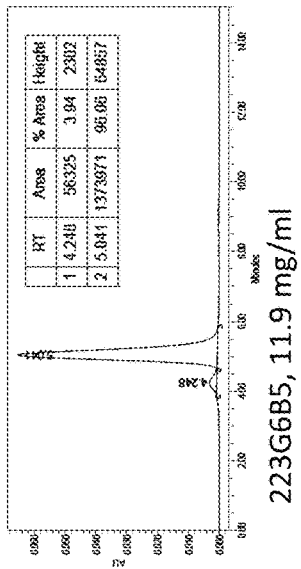
FIG. 41 shows the solubility of fully human anti-PD-1 antibodies according to embodiments of the invention.
Figure 41:
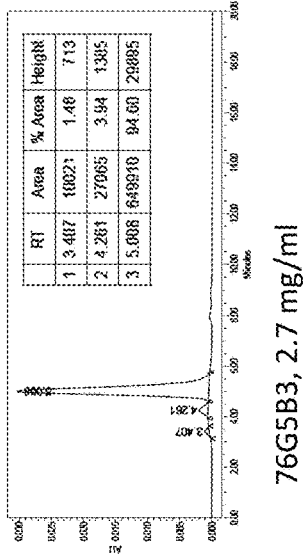
Figure 41:
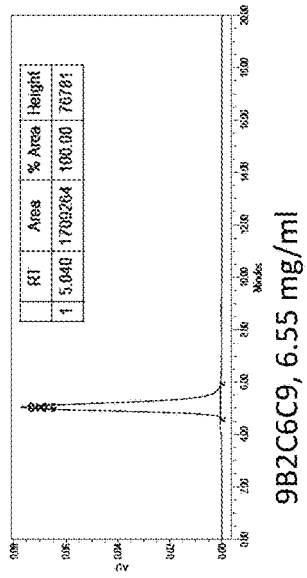
Figure 41:
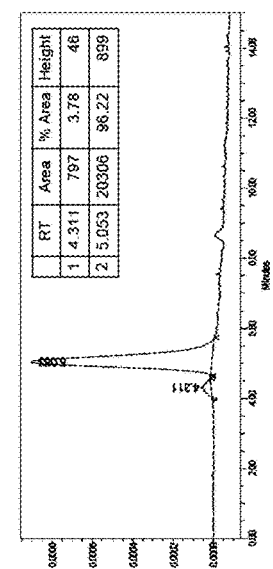
Figure 41:
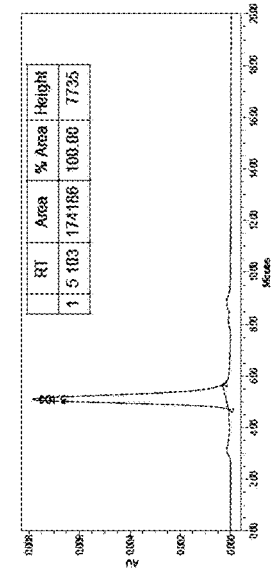
Figure 41:
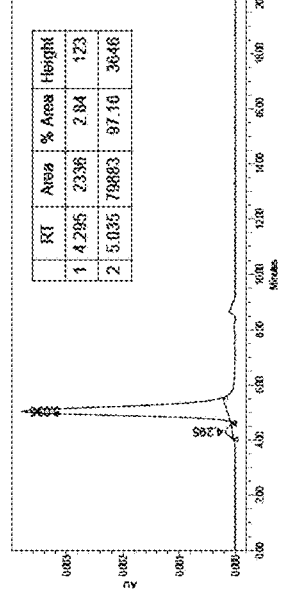

Fully human anti-PD-1 antibodies were adjusted to 1 mg/mL and a final volume of about 700 uL with sample buffer. The parameters were set up as follows (VP-DSC): Starting Temperature 30° C.; Final Temperature 100° C.; Scan rate 50° C./hour; Number of Rescans 0; Pre Scan Thermostat 3 min; PostScan Thermostat 0 min; Post Cycle Thermostat 25° C.; Filtering Period 25 seconds; Feedback Mode/Gain None; Cell Refill Parameters 35° C. The resulting protein-buffer thermograms were processed by subtracting a corresponding buffer-buffer scan and subsequently fitting a baseline to the trace. The Tms were recorded at each peak maxima observed in the thermograms using Origin™ 7.0 software. The results are shown in FIG. 39.

Example 11—Antibody Freeze/Thaw Stability

The freeze/thaw stabilities of the fully human anti-PD-1 antibodies were characterized as follows. A 100 uL aliquot from the frozen stocks of each anti-PD-1 antibody was thawed at room temperature. Once fully thawed, the samples were then rapidly frozen in the −80° C. freezer and kept at −80° C. for at least two hours before being thawed again at room temperature. The samples went through three identical freeze/thaw cycles. Visual inspection was used to check for precipitation. 20 uL aliquots were removed from the samples for size-exclusion chromatography (SEC) analysis after three freeze/thaw cycles. The stability of the fully human anti-PD-1 antibodies before and after the freeze/thaw cycles were analyzed by HPLC-SEC characterization. The results, shown in FIG. 40, demonstrated that after three freeze/thaw cycles, monomer IgGs accounted for more than 95% of each of the anti-PD-1 antibodies tested.

Example 12—Antibody Solubility

The solubility of the fully human anti-PD-1 antibodies was characterized by concentrating 10 mg IgG using centrifugal filters (Amicon Ultra-0.5 mL 30K) at 14000 g at 4° C. down to >100 mg/mL. 2 mL or more of IgG was added into the centrifugal filters and concentrated at 14000 g at 4° C. The setting time of centrifuging was 2 min, 3 min, 5 min, 8 min, 15 min, and 20 min, and each time 20 uL were aliquoted to a collection tube to measure the concentration with a nanodrop at A280. The centrifugation was finished when the concentration reached 100 mg/mL. For HPLC-SEC characterization, 6 uL of concentrated samples were injected into an HPLC-SEC column, and the percentages of monomers and aggregates were determined based on the peak area. The results, shown in FIG. 41, demonstrated that all of the fully human anti-PD-1 antibodies tested had a solubility over 100 mg/mL and that monomer IgGs were higher than 95% for all of the anti-PD-1 antibodies tested.

While the invention has been described in detail, and with reference to specific embodiments thereof, it will be apparent to one of ordinary skill in the art that various changes and modifications can be made therein without departing from the spirit and scope of the invention.

REFERENCES

Blank et al., 2005, Cancer Immunotherapy, 54:307-314
Brahmer et al., 2010, J. Clin. Oncol., 28:3167-75
Freeman et al., 2000, J. Exp. Med., 192:1027-34
Greenwald et al., 2005, Annu. Rev. Immunol. 23:515-48
Harding and Lonberg, 1995, Ann. N.Y. Acad. Sci. 764:536-546
Hirano et al., 2005, Cancer Res., 65:1089-96
Kabat, 1991, "Sequences of proteins of objective interest," the NIH, Bethesda, Md.
Kipriyanov et al., 1997, Peds. 10:445-453
Lonberg and Huszar, 1995, Internal Rev. Immunol. 13:65-93
Lonberg et al., 1994, Nature 368: 856-859
Sambrook and Russell, 1989, Molecular cloning: a laboratory manual, New York: Cold Spring Harbor Laboratory Press, 2nd ed.
Sharpe et al., 2007, Nat. Immunol. 8:239-45
Topalian et al., 2014, J. Clin. Oncol., 32:1020-30
Weinstock and McDermott, 2015, TherAdv Urol., 7(6):365-77
Wherry, 2011, Nat. Immunol., 12:492-99
Zippelius et al., 2015, Cancer Immunol Res.; 3(3):236-44
Zou and Chen L, 2008, Nat Rev Immunol., 8(6):467-77

We claim:

1. An isolated monoclonal antibody or antigen-binding fragment thereof comprising LCDR1, LCDR2, LCDR3, HCDR1, HCDR2 and HCDR3, having the polypeptide sequences of:

SEQ ID NOs: 30, 31, 32, 26, 27, and 28, respectively; wherein the antibody or antigen-binding fragment thereof binds programmed cell death protein-1 (PD-1).

2. The isolated monoclonal antibody or antigen-binding fragment of claim 1, comprising a heavy chain variable region having a polypeptide sequence at least 95% identical to SEQ ID NO: 25 or a light chain variable region having a polypeptide sequence at least 95% identical to SEQ ID NO: 29.

3. The isolated monoclonal antibody or antigen-binding fragment of claim 1, comprising:
   a heavy chain variable region having the polypeptide sequence of SEQ ID NO: 25, and a light chain variable region having the polypeptide sequence of SEQ ID NO: 29.

4. The isolated monoclonal antibody or antigen-binding fragment of claim 1, wherein the antibody or antigen-binding fragment thereof is chimeric.

5. The isolated monoclonal antibody or antigen-binding fragment of claim 1, wherein the antibody or antigen-binding fragment thereof is human.

6. The isolated monoclonal antibody or antigen-binding fragment of claim 5, comprising a human heavy chain IgG4 constant region having a S228P mutation, and a human antibody light chain kappa constant region.

7. An isolated nucleic acid encoding the monoclonal antibody or antigen-binding fragment of claim 1.

8. A vector comprising the isolated nucleic acid of claim 7.

9. A host cell comprising the nucleic acid of claim 7.

10. A pharmaceutical composition, comprising the isolated monoclonal antibody or antigen-binding fragment of claim 1 and a pharmaceutically acceptable carrier.

11. A method of blocking binding of PD-1 to programmed cell death-ligand 1 (PD-L1) or programmed cell death-ligand 2 (PD-L2), or augmenting secretion of IFN-γ and IL-2 in a subject in need thereof, comprising administering to the subject the pharmaceutical composition of claim 10.

12. A method of treating a tumor in a subject in need thereof, comprising administering to the subject the pharmaceutical composition of claim 10, wherein the tumor is selected from the group consisting of a solid tumor, a hematologic cancer, bladder cancer, biliary cancer, brain cancer, breast cancer, colon cancer, esophageal cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer and the tumor cell thereof expresses PD-L1.

13. A method of producing the monoclonal antibody or antigen-binding fragment of claim 1, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or cell culture.

14. A method of producing a pharmaceutical composition comprising the monoclonal antibody or antigen-binding fragment of claim 1, comprising combining the monoclonal antibody or antigen-binding fragment with a pharmaceutically acceptable carrier to obtain the pharmaceutical composition.

15. A method of treating a tumor in a subject in need thereof, comprising administering to the subject the pharmaceutical composition of claim 10, wherein the tumor is selected from the group consisting of a colon cancer, esophageal cancer, gastric cancer, glioma, head cancer, leukemia, liver cancer, lung cancer, lymphoma, myeloma, neck cancer, ovarian cancer, melanoma, pancreatic cancer, renal cancer, salivary cancer and stomach cancer; and the tumor cell thereof expresses PD-L1.

* * * * *